US011154858B2

(12) United States Patent
Gottardi et al.

(10) Patent No.: US 11,154,858 B2
(45) Date of Patent: Oct. 26, 2021

(54) MICROFLUIDIC TISSUE DEVELOPMENT SYSTEMS

(71) Applicant: University of Pittsburgh—Of the Commonwealth System of Higher Education, Pittsburgh, PA (US)

(72) Inventors: Riccardo Gottardi, Pittsburgh, PA (US); Peter Alexander, Wexford, PA (US); Bryan Romell, Pittsburgh, PA (US); Rocky S. Tuan, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 499 days.

(21) Appl. No.: 15/765,567

(22) PCT Filed: Oct. 6, 2016

(86) PCT No.: PCT/US2016/055763
§ 371 (c)(1),
(2) Date: Apr. 3, 2018

(87) PCT Pub. No.: WO2017/062629
PCT Pub. Date: Apr. 13, 2017

(65) Prior Publication Data
US 2019/0076840 A1 Mar. 14, 2019

Related U.S. Application Data

(60) Provisional application No. 62/238,033, filed on Oct. 6, 2015, provisional application No. 62/402,346, filed on Sep. 30, 2016.

(51) Int. Cl.
*B01L 3/00* (2006.01)
*B01L 99/00* (2010.01)
(Continued)

(52) U.S. Cl.
CPC ....... *B01L 3/502715* (2013.01); *C12M 21/08* (2013.01); *C12M 23/12* (2013.01);
(Continued)

(58) Field of Classification Search
CPC ....... B01L 2300/042; B01L 2300/0627; B01L 2300/0829; B01L 2300/0848;
(Continued)

(56) References Cited

U.S. PATENT DOCUMENTS 3,361,839 A    1/1968  Lester
5,081,035 A    1/1992  Halberstadt et al.
(Continued)

FOREIGN PATENT DOCUMENTS

WO    WO 2005/047466    5/2005
WO    WO 2007/008609    1/2007
(Continued)

OTHER PUBLICATIONS

International Search Report and Written Opinion for related International Application No. PCT/US2016/055763, dated Dec. 22, 2016, 16 pages.
(Continued)

*Primary Examiner* — Gautam Prakash
*Assistant Examiner* — Lydia Edwards
(74) *Attorney, Agent, or Firm* — Klarquist Sparkman, LLP

(57) ABSTRACT

Disclosed herein are various bioreactor devices and systems for growing cellular material, and related methods of growing cellular material. In some cases, a system can include a bioreactor system having one or more wells with at least one fluidic passageway coupled to each well to feed fluids to biological material being developed inside the well. In some cases, a bioreactor system can include a main body comprising the perimeter of the well and the fluidic passage-
(Continued)

ways, a cover that forms the top of the well and provides optical access into the well, and a base that forms the bottom surface of the well. The cover and base can be attached and detached from the main body to seal the well closed and to physically access the contents of the well.

30 Claims, 63 Drawing Sheets

(51) Int. Cl.
  *C12M 1/24* (2006.01)
  *C12M 1/32* (2006.01)
  *C12M 1/00* (2006.01)
  *C12M 1/42* (2006.01)
  *C12M 3/00* (2006.01)
  *C12M 1/12* (2006.01)
  *C12M 1/34* (2006.01)

(52) U.S. Cl.
  CPC ............ *C12M 23/38* (2013.01); *C12M 25/14* (2013.01); *C12M 29/10* (2013.01); *C12M 35/08* (2013.01); *C12M 41/36* (2013.01); *B01L 2300/042* (2013.01); *B01L 2300/0627* (2013.01); *B01L 2300/0829* (2013.01); *B01L 2300/0848* (2013.01); *B01L 2300/0867* (2013.01)

(58) Field of Classification Search
  CPC ...... B01L 2300/0867; B01L 3/502715; C12M 21/08; C12M 23/12; C12M 23/38; C12M 25/14; C12M 29/10; C12M 35/08; C12M 41/36
  See application file for complete search history.

(56) References Cited

U.S. PATENT DOCUMENTS

| D658,306 S | 4/2012 | Gevaert et al. |
|---|---|---|
| 2002/0028504 A1 | 3/2002 | MacCaskill et al. |
| 2006/0110822 A1 | 5/2006 | Robbins et al. |
| 2007/0128715 A1 | 6/2007 | Vukasinovic et al. |
| 2008/0032380 A1* | 2/2008 | Kleis ................... C12M 23/24 435/243 |
| 2011/0207175 A1 | 8/2011 | Ei-Sabban et al. |
| 2012/0122208 A1 | 5/2012 | Fisher et al. |
| 2012/0183987 A1 | 7/2012 | Gevaert et al. |
| 2015/0247112 A1 | 9/2015 | Orr et al. |
| 2016/0201037 A1 | 7/2016 | Tuan et al. |

FOREIGN PATENT DOCUMENTS

| WO | WO 2010/048417 | 4/2010 |
|---|---|---|
| WO | WO 2011/014674 | 2/2011 |
| WO | WO 2014/127250 | 8/2014 |
| WO | WO 2015/027186 | 2/2015 |

OTHER PUBLICATIONS

Extended European Search Report for Application No. 16854326.2, dated Apr. 2019, 6 pages.

International Search Report and Written Opinion for related International Application No. PCT/US2014/052348, dated Dec. 15, 2014, 13 pages.

Spitters et al., "A Dual Flow Bioreactor with Controlled Mechanical Stimulation for Cartilage Tissue Engineering," Tissue Engineering: Part C, 19(10), 10 pages (Aug. 2013).

* cited by examiner

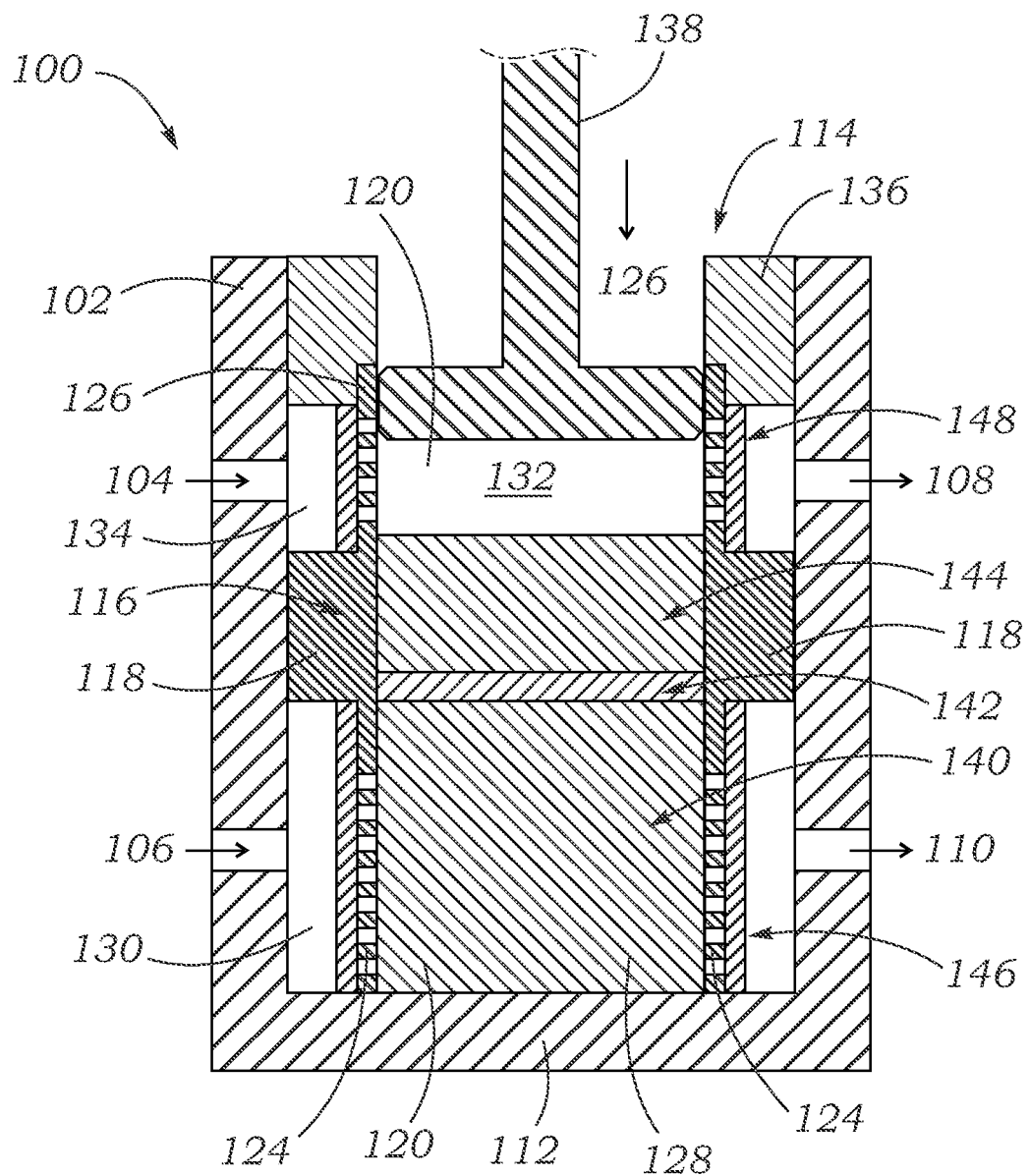

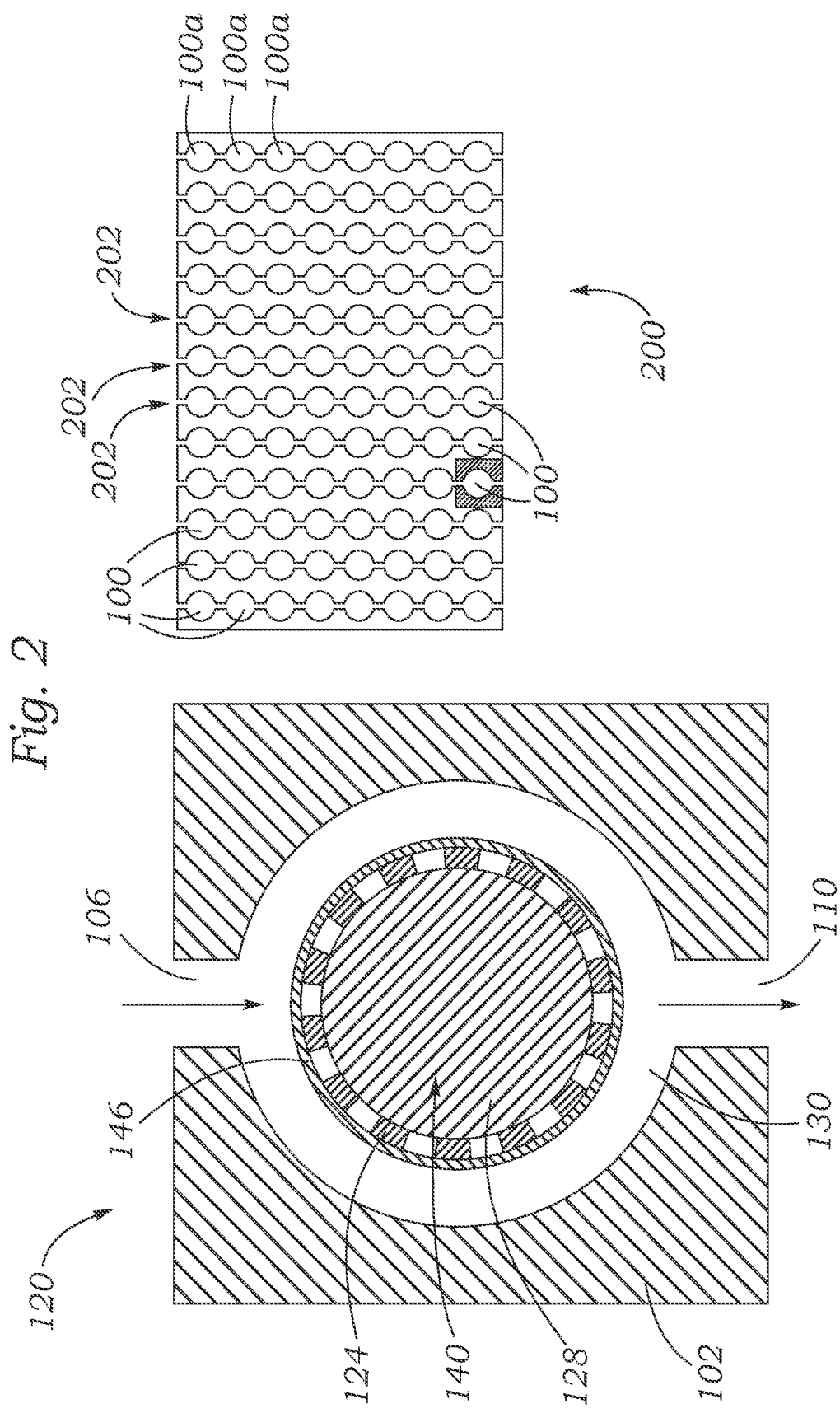

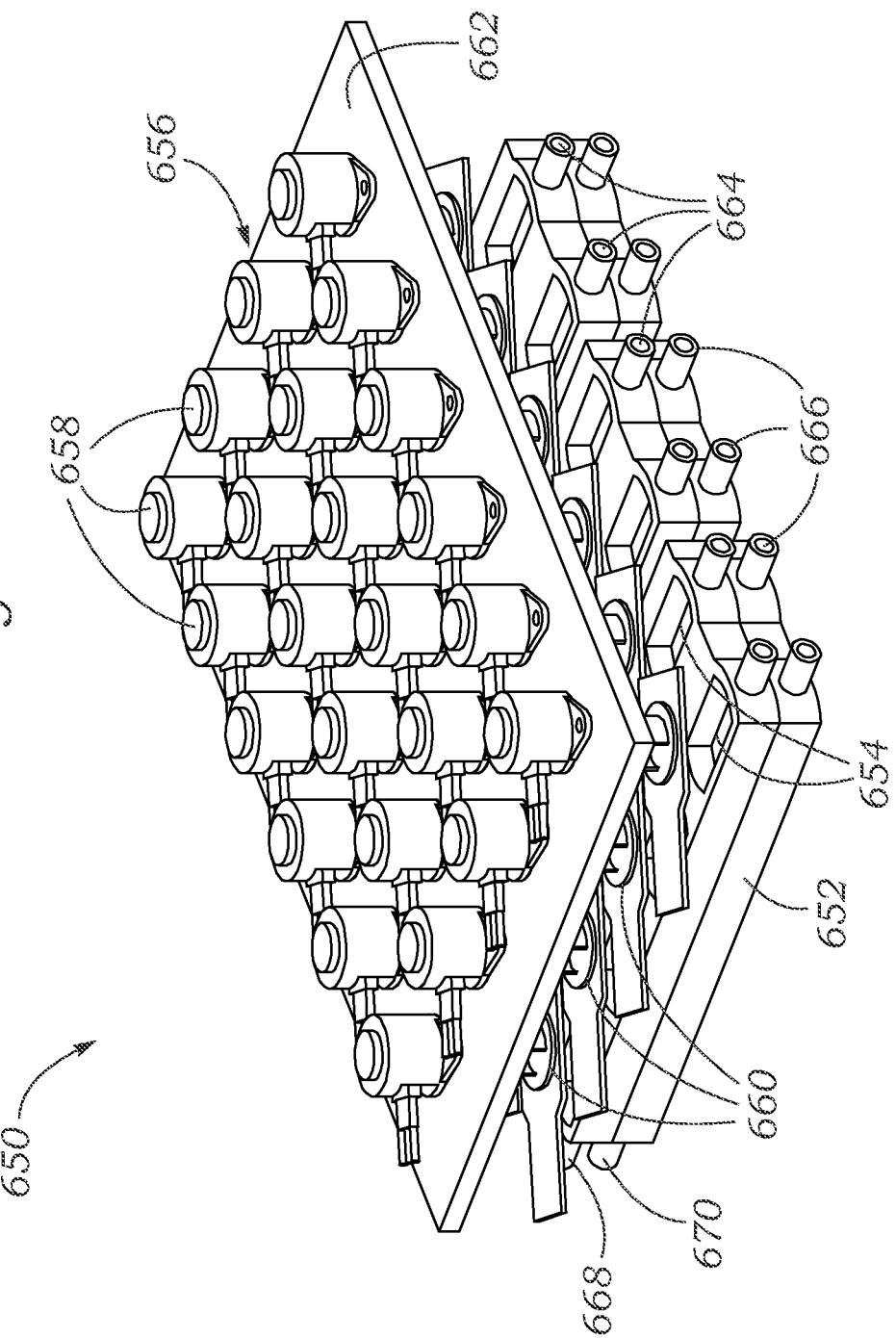

FIG. 12A
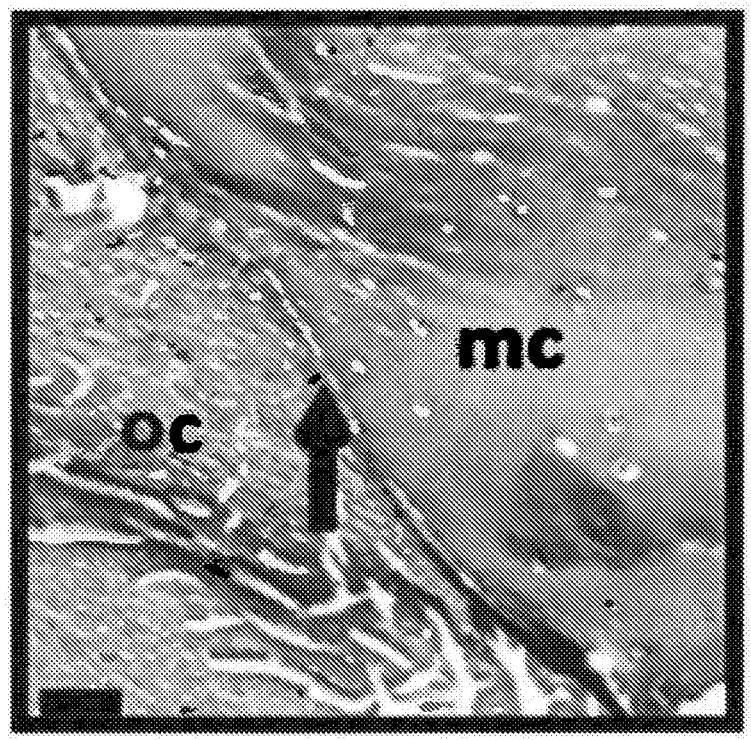
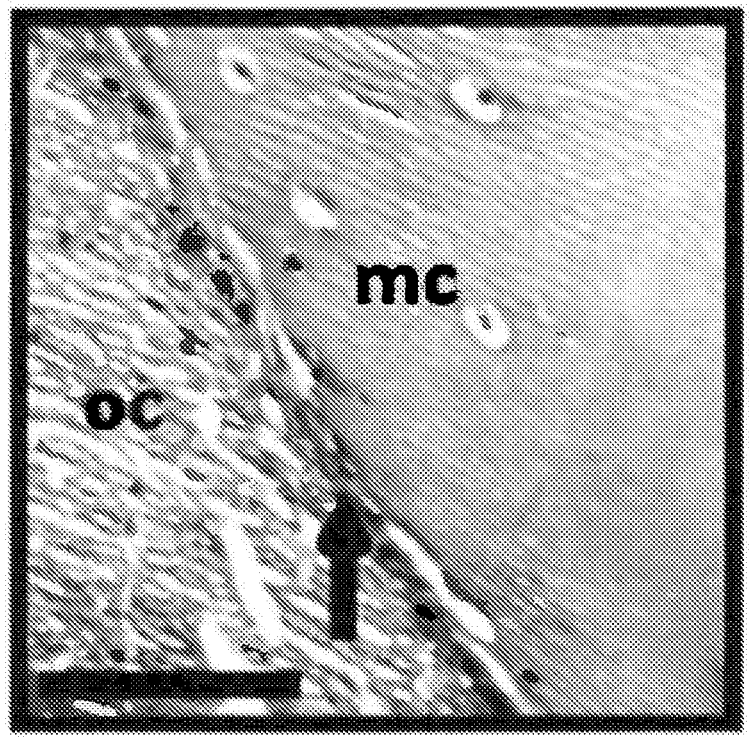
FIG. 12B

FIG. 13A
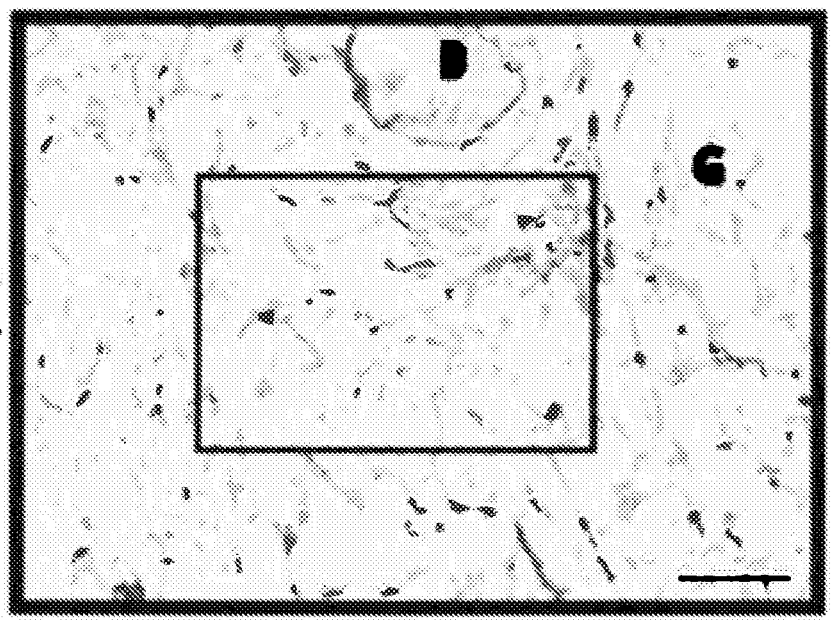
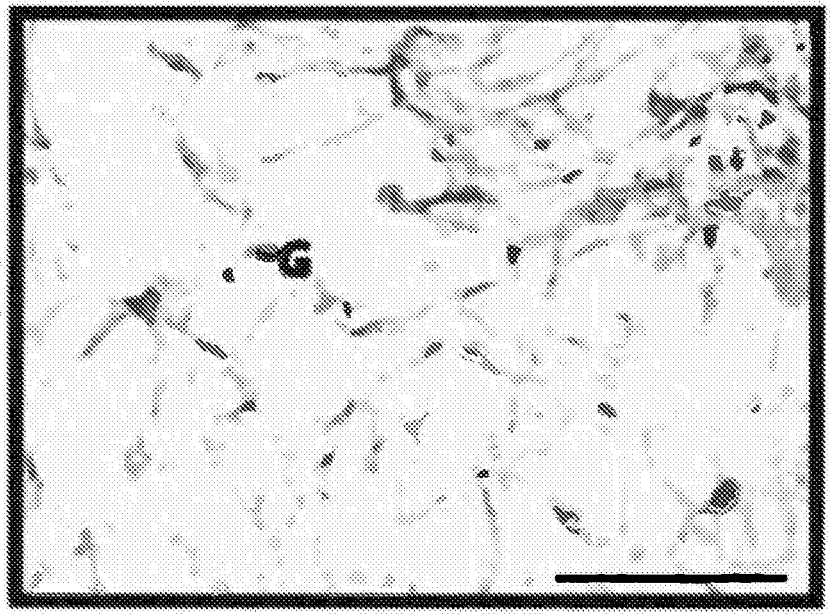
FIG. 13B

FIG. 14A
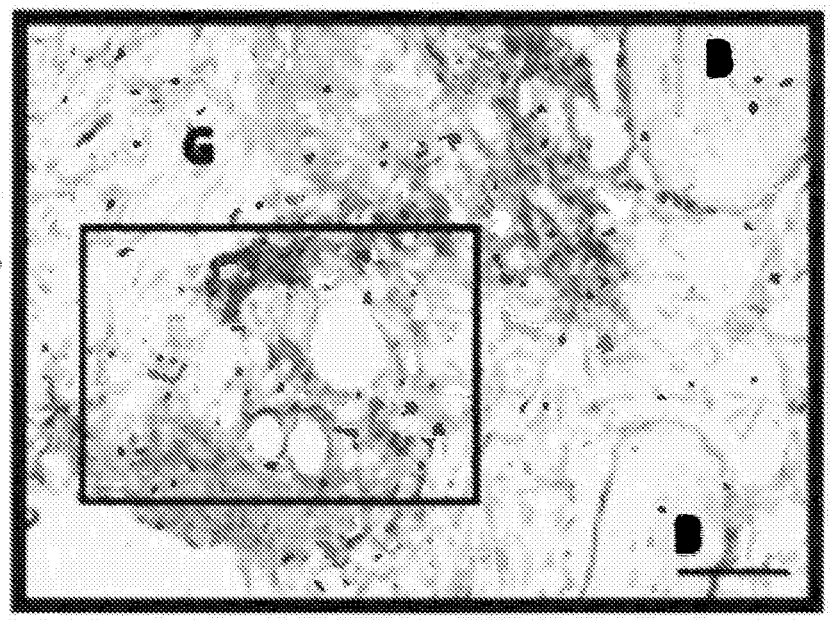
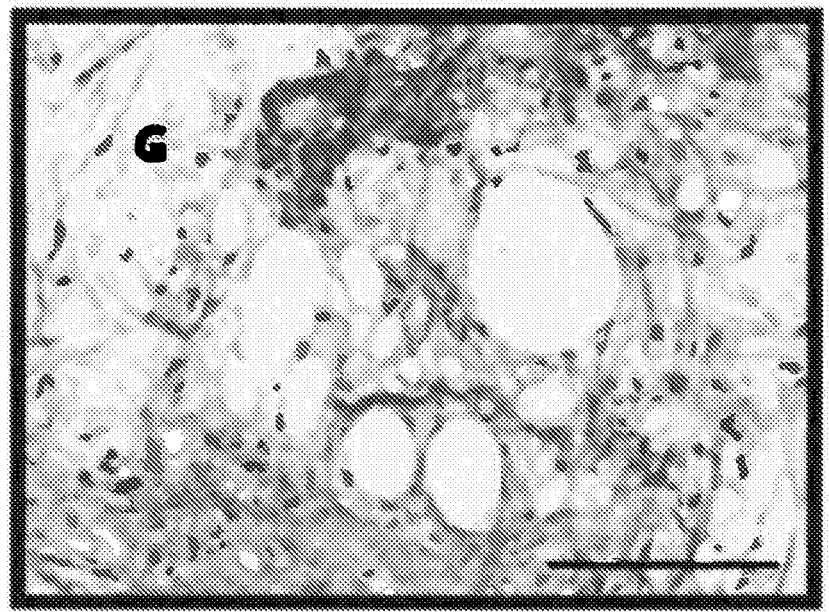
FIG. 14B

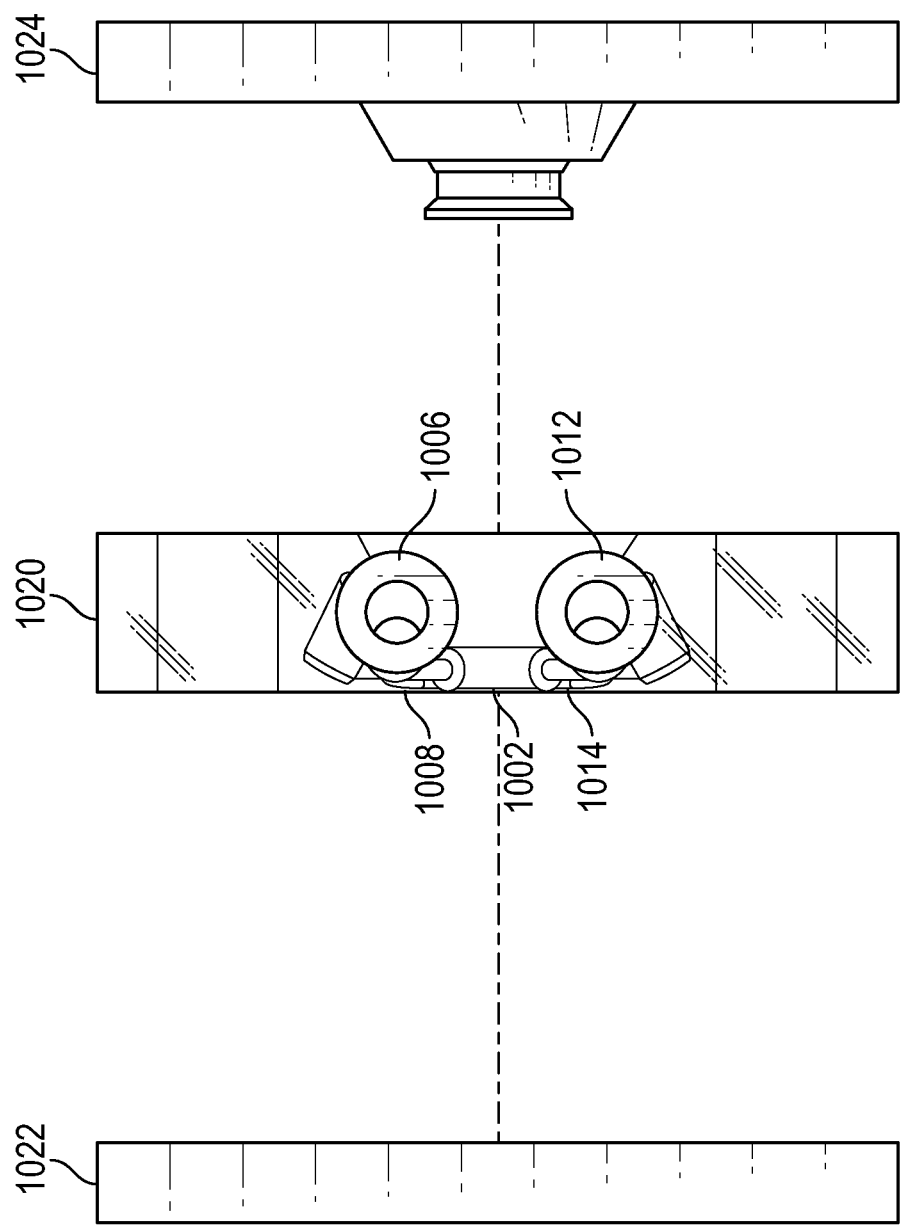

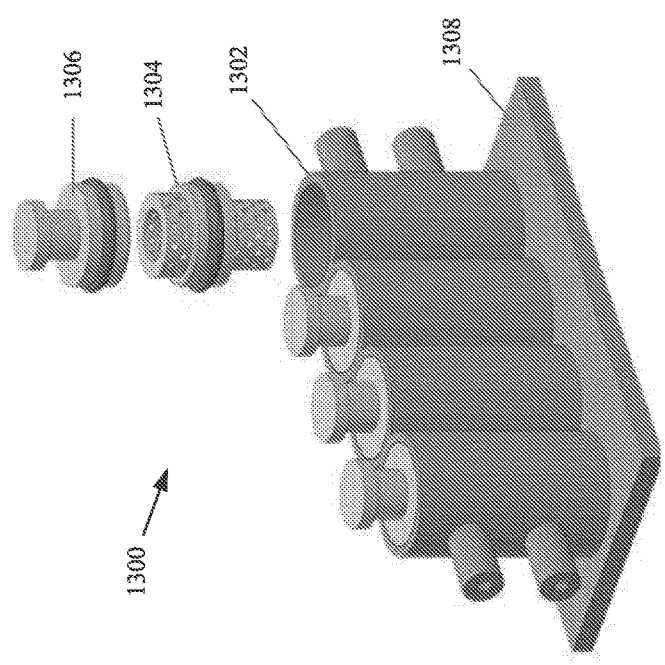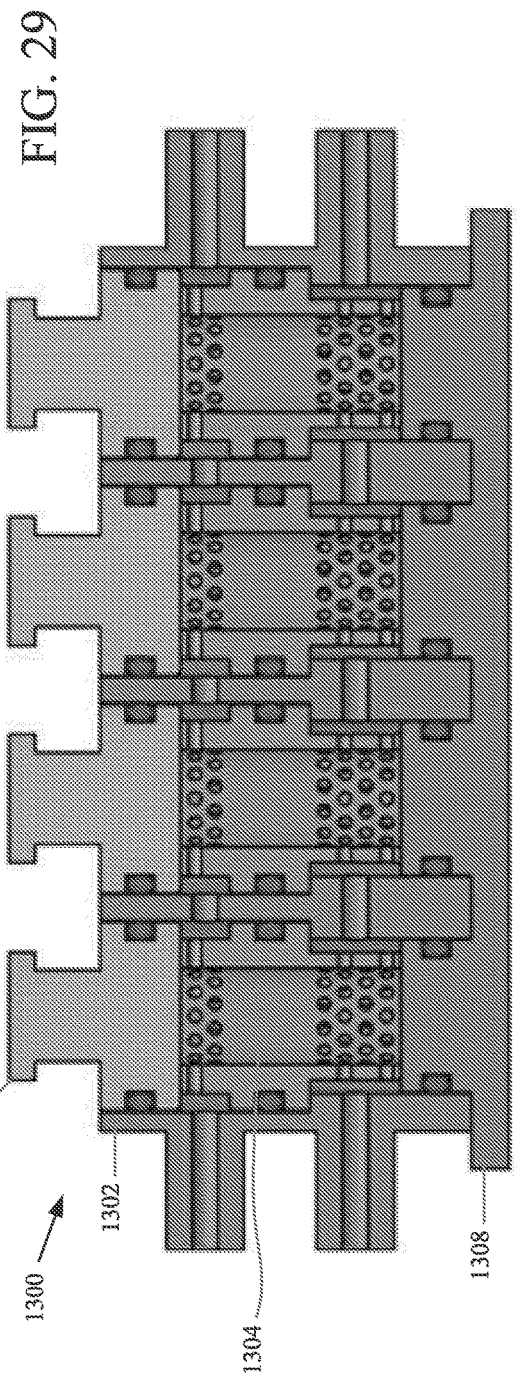
FIG. 28
FIG. 29

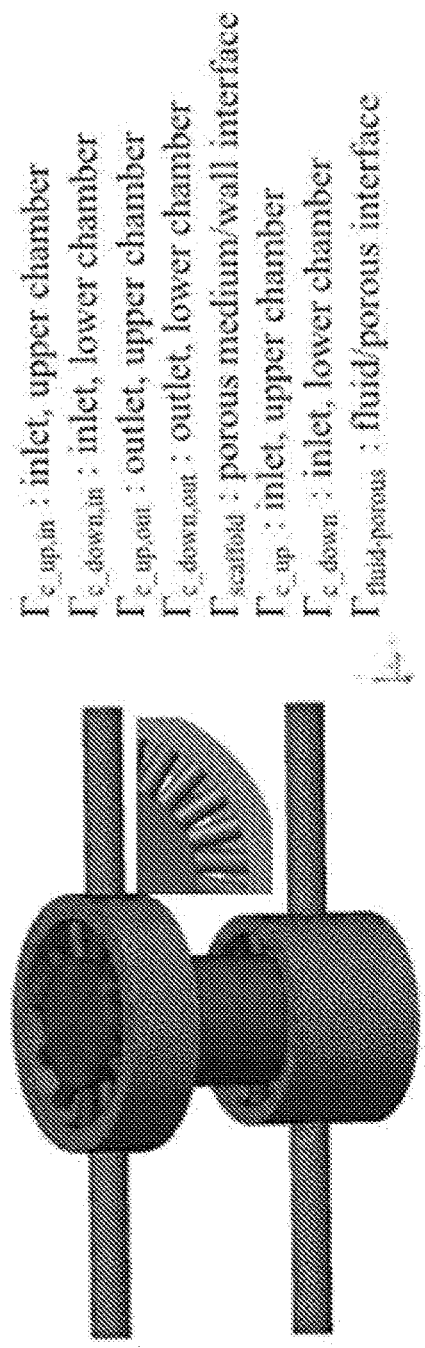
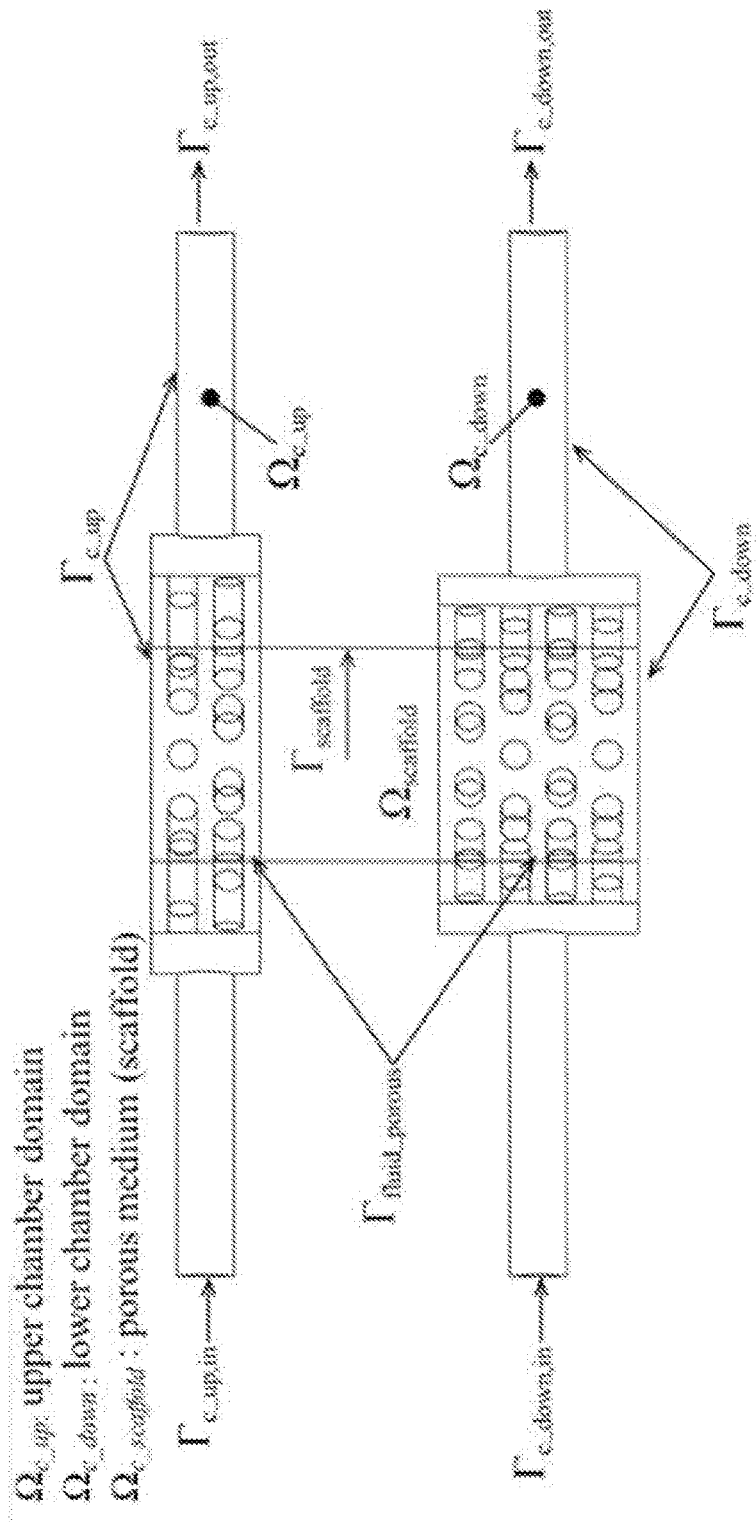
FIG. 33

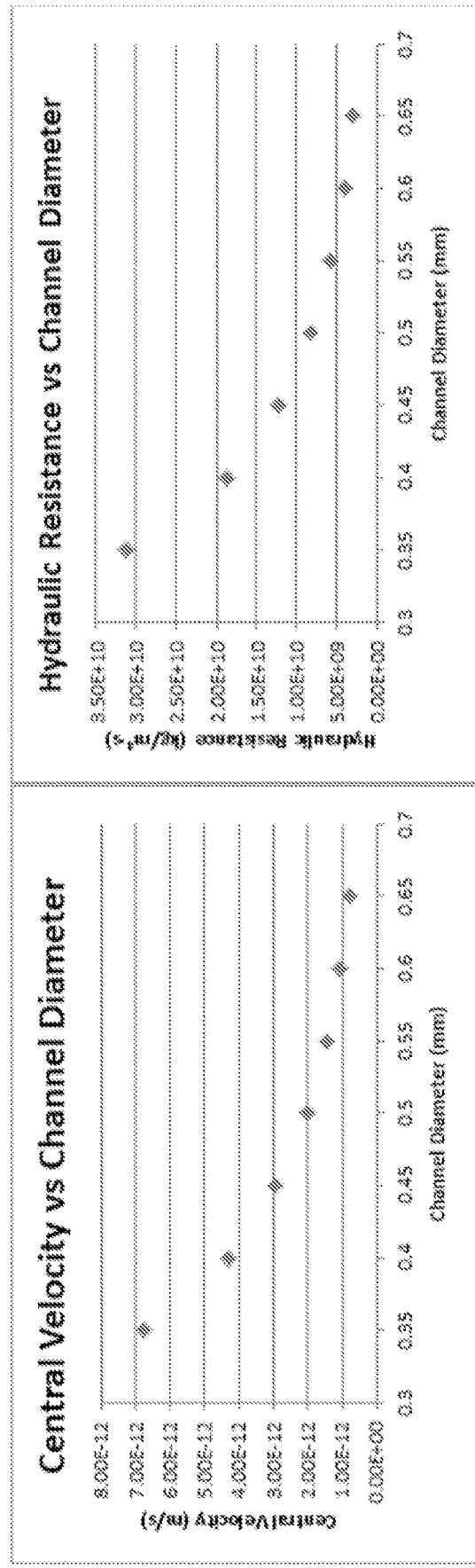
FIG. 60
FIG. 61
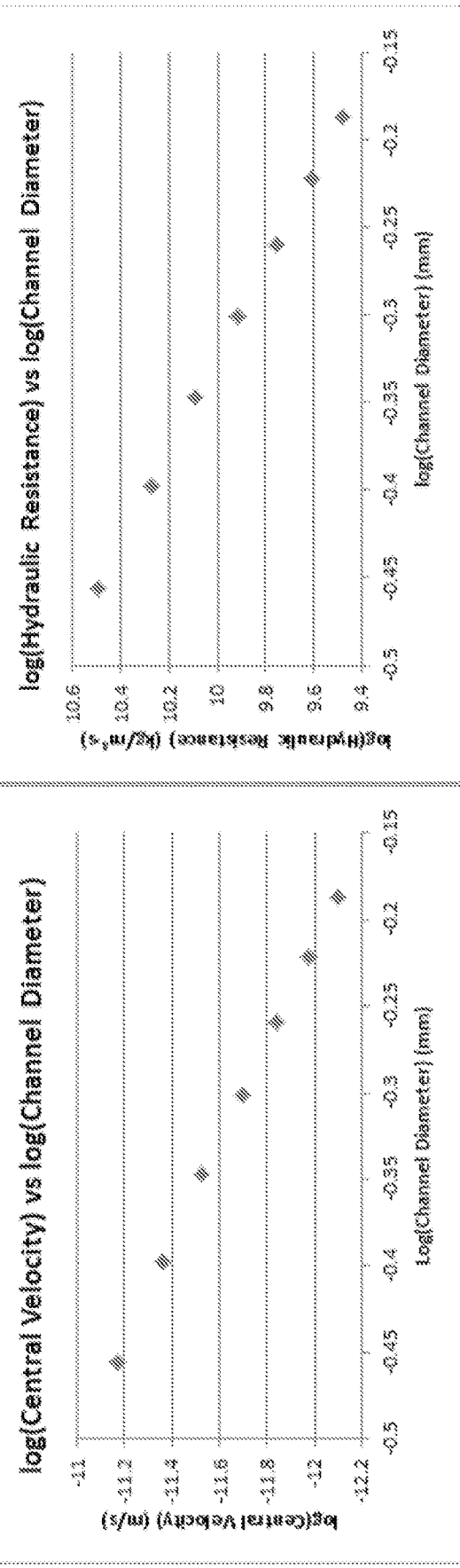
FIG. 62
FIG. 63

MICROFLUIDIC TISSUE DEVELOPMENT SYSTEMS

CROSS-REFERENCE TO RELATED APPLICATIONS

This application is the U.S. National Stage of International Application No. PCT/US2016/055763 filed Oct. 6, 2016, which claims the benefit of U.S. provisional patent application No. 62/238,033 filed Oct. 6, 2015, and U.S. provisional patent application No. 62/402,346 filed Sep. 30, 2016, both of which are incorporated by reference herein in their entirety.

FIELD

The present disclosure relates to bioreactor devices and systems for growing cellular material, and to related methods of growing cellular material.

BACKGROUND

There exist many biological structures comprising multiple layers of different, interacting, tissue types. For example, epithelial layers rest on basement membranes that separate them from different underlying tissue layers, as in the circulatory system (blood vessels), digestive system (esophagus, stomach, intestine), endocrine system (thyroid and other glands), integumentary system (skin), reproductive system (ovaries, fallopian tubes, endometrium, cervix, vagina, testes, and vas deferens), respiratory system (oropharynx, larynx, trachea, bronchioles), sensory system (cornea), and the urinary system (bladder and urethra). Both epithelial and non-epithelial tissues are juxtaposed with different types of biological tissues in the body, and may have cooperative biological effects on one another. It would be helpful to study different tissue types in vitro in an environment that takes into account the interactive nature of biological tissues.

One example of a tissue complex comprising a plurality of different tissues is the osteochondral tissue complex, which can in some cases be affected by osteoarthritis (OA). OA is the most prevalent form of arthritis, affecting up to 15% of the adult population. OA is principally characterized by degeneration of the articular cartilage component of the joint, often with accompanying subchondral bone lesions. Understanding the mechanisms underlying the pathogenesis of OA is important for the rational development of disease modifying OA drugs (DMOADs). Most studies on OA have focused on the investigation of either the cartilage or the bone component of the articular joint.

OA is a chronic degenerative disease of the articular joint which involves cartilage, synovium, ligaments, bone, meniscus, tendon, and peri-articular muscle. Cartilage destruction is one of the common characteristics of OA progression, and results in malfunction of the affected joint. Normal articular cartilage is comprised of large amounts of extracellular matrix (mainly collagen type II), produced and maintained by chondrocytes, the sole cell type in the cartilage. During disease progression, net loss of cartilage matrix results from an imbalance between cartilage matrix degradation and synthesis by chondrocytes in the cartilage. Due to absence of vascularization in the articular cartilage, the capacity of self-repair in cartilage is limited, and currently, there is no effective therapy for the treatment of OA except relieving the symptoms of the diseases until the joints need to be replaced by surgery.

OA involves more than simply degeneration of the articular cartilage—it is in fact a disease of the osteochondral tissue complex. The osteochondral junction is highly structured; the uppermost superficial zone is characterized by elongated chondrocytes with collagen fibrils aligning parallel to the articular surface. In the middle/intermediate zone, rounded chondrocytes and collagen fibrils are less organized relative to the surface. In the deep zone, vertical columns of chondrocytes and fibers are organized perpendicular to the articular surface. The highest concentration of proteoglycans is found in the deep zone. Adjacent to deep cartilage is the calcified cartilage zone, which is characterized by larger and more dispersed hypertrophic chondrocytes. A wavy basophilic matrix, known as the tidemark, highlights the boundary between the deep and calcified cartilage zones. Vertically oriented collagen fibers pass through the tidemark from the deep zone to the calcified cartilage and are important for transferring mechanical forces. Overall, the calcified zone marks the transition from soft cartilage to stiff subchondral bones and is important for attaching the noncalcified cartilage to bone. The subchondral bone is interdigitated with calcified cartilage, but, interestingly, the collagen fibers do not extend from the calcified zone to the bone. This physical linkage between cartilage and bone is a critical component in the pathogenesis of degenerative diseases such as OA.

There exists some debate as to whether OA begins in the cartilage or the bone and whether subchondral bone or articular cartilage is the more appropriate target for disease modifying OA drug (DMOAD) development. Supporters of the "bone first" side of the debate maintain that, as the "substrate" for articular cartilage, subchondral bone plays a support role in cartilage health, and that any perturbations to subchondral bone are amplified as pathological conditions and are transferred from bone to cartilage. For example, studies have shown that osteophyte formation and changes in subchondral bones appear before measurable changes in articular cartilage thickness as well as related joint space narrowing. Another group of studies suggest that healthy subchondral bone is essential for healthy cartilage. In tissue plugs cultured in vitro, bone tissue preserves chondrocyte survival. To some extent, the conventional wisdom has been that healthy subchondral bone presents an impenetrable, impermeable barrier. However, it is possible that cartilage receives nutrients, cytokines, hormones, and other biological signals from bone in vivo, and vice versa.

Proponents of the "cartilage first theory" argue that, while early changes to cartilage during OA are clearly coupled to bone alterations via mechanical and soluble factors, changes to the bone seem to be secondary to alterations in articular cartilage. Supporting evidence suggests that OA changes to cartilage alter the mechanical environment of the bone cells and induce them, in turn, to modulate tissue structure. Several studies report that thickening of calcified cartilage along with tidemark advancement contributes to thinning of articular cartilage. This leads to increased mechanical stresses in the matrix of the deep zone of cartilage and contributes to OA cartilage deterioration.

SUMMARY

The present disclosure describes small-scale, three-dimensional (3D) bioreactor systems that can be used to model the anatomy, biology, and physiology of native tissues, including different tissues that are adjacent or contiguous in the body such as the osteochondral complex of the articular joint. In certain embodiments, two or more different tissues can be grown adjacent to one another in a bioreactor. A bioreactor can be configured with one chamber, or with two or more chambers that are each provided with the same or different nutrients and/or other fluids, such that different tissues grown or tested in the bioreactor can be fed with the same or different nutrients or fluids. Thus, two or more tissues can be grown adjacent to one another and their interaction(s) can be studied.

In certain embodiments, a bioreactor can include an upper chamber having inlet and outlet ports and a lower chamber having inlet and outlet ports. The inlet ports can be fed by the same or independent sources of biological nutrients, such as liquid cell growth medium, that is perfused through each chamber from the inlet port to the outlet port. A first tissue can be situated in the upper chamber so as to be exposed to the biological nutrients fed through the upper inlet port, and a second tissue can be situated in the lower chamber so as to be exposed to the biological nutrients fed through the lower inlet port. In certain embodiments, one or more additional tissue layers can be situated at an interface that extends partially or completely between the first and second tissues. For example, the additional tissue layer may be a stem cell layer that can differentiate into the first tissue and/or the second layer, and/or that mediates biochemical communication between those layers. In particular examples, the additional layer is a stem cell layer of ectoderm, mesenchyme, or endoderm. In some embodiments, the upper chamber and second chamber can establish substantially separate microenvironments for the first and second tissue by supplying separate media or nutrient flow through the upper and lower inlet ports. Biochemical communication between the separate microenvironments can occur via biochemical signals produced by the additional intermediate layer at the interface instead of via the nutrient media flow.

One exemplary application of the devices, systems and methods described herein is in improved studies of the osteochondral complex and OA. While previous OA studies have focused on the investigation of either the cartilage or the bone component of the articular joint, the osteochondral complex represents a more physiologically relevant target as OA ultimately is a disorder of osteochondral integrity and function. Thus, interactions between both bone and cartilage are central to OA progression, and in studying OA, bone and cartilage are capable of being studied together instead of separately. Thus, the present disclosure describes 3D microtissue constructs including both cartilage and bone, in order to appropriately study the osteochondral environment and OA in vitro.

Different osteogenic and chondrogenic tissue components can be produced using adult human mesenchymal stem cells (MSCs) derived from bone marrow and adipose seeded within biomaterial scaffolds photostereolithographically fabricated with a well-defined internal architecture. A 3D perfusion-ready container platform, such as a 3D printed platform, can house and maintain an osteochondral microsystem having any combination or all of the following features: (1) an anatomic cartilage/bone biphasic structure with a functional interface; (2) all tissue components derived from a single stem cell, such as an adult mesenchymal stem cell source to eliminate possible age/tissue type incompatibility; (3) individual compartments to constitute separate microenvironments, for example for the "synovial" and "osseous" components; (4) accessible individual compartments which can be controlled and regulated via the introduction of bioactive agents or candidate effector cells, and tissue/medium sampling and compositional assays; and (5) compatibility with the application of mechanical load or other perturbations, such as chemical, toxicological and other physical perturbations. In certain embodiments, the container platform is dimensioned to fit within the wells of multiwell tissue culture plates, such as 24, 48, or 96 well plates, to perform high-throughput assays. The bioreactor can also have remote imaging capability to allow non-invasive functional monitoring of the bioreactor tissues.

The consequences of external perturbations, such as mechanical injury, exposure to drugs or inflammatory cytokines, and compromised bone quality, on degenerative changes in the cartilage component can be examined in the osteochondral microsystem as a first step towards its eventual application as an improved and high-throughput in vitro model for prediction of efficacy, safety, bioavailability, and toxicology outcomes for candidate DMOADs. For example, the effect of corticosteroids or osteoactive agents on the different tissue types, such as bone and cartilage tissue, can be assessed. In addition, drug screening can be performed to identify potential therapeutic agents to treat OA.

In some embodiments, a bioreactor can include a fluidic well plate having dimensions equivalent to those of standard laboratory multi-well plates. The fluidic well plate can have various numbers of wells, such as one well, six wells, twelve wells, twenty-four wells, or ninety-six wells. The wells of the well plates can be arranged in a grid having rows and columns, and a row or a column of wells can be fluidically connected by a first conduit feeding upper portions of each of the wells in the row or column and by a second conduit feeding lower portions of each of the wells in the row or column. Each conduit can begin and terminate at the end of the plate at an inlet or an outlet port.

In some embodiments, a bioreactor can include a fluidic well insert configured to fit tightly within one of the wells of the fluidic well plate and to support biological tissues at an interior of the insert. The insert can include a circumferential flange which seals the insert against the inside surface of one of the wells of the fluidic well plate, thereby separating the respective well into the upper and lower portions fed by the first and second conduits, respectively. The insert can be hollow and thus biological tissues can be housed inside the insert. The circumferential flange can separate an upper portion of the insert from a lower portion of the insert, and each of the upper and lower portions of the insert can include pores through which fluids can flow. The insert can be configured to be situated within a standardized, commercially available well plate.

In some embodiments, a bioreactor can include a lid and an associated support system which is configured to seal the fluidic well plate. The lid can include a micro-mechanical actuator and a force sensor to provide controllable deformation or load to tissue constructs in the well plate. The micromechanical actuator can be associated with and aligned on center with a well of the well plate. The lid can be used with a commercially available well plate with or without an insert situated in a well thereof.

Some embodiments include a modular, microfluidic, multi-tissue, mechano-active 3D bioreactor. A bioreactor can include a microfluidic base, a bioreactor insert, and a mechanoactivating lid assembly. In various embodiments, a base, insert, and lid assembly can be used in various combinations, sub-combinations, or individually. In some embodiments, a base permits direct or indirect interaction of two or more native or engineered tissue types while simultaneously providing separate fluid types to the various tissue types via microfluidic conduits which feed the tissue directly or via biological or physical intermediates within the geometry of standard multi-well plates.

A bioreactor can be amenable and adaptable to common tissue culture practices and devices (e.g., multi-channel pipettes, etc.) and high-throughput formats, depending on the scale of the wells. The insert can divide a single well into upper and lower compartments which do not communicate directly. They may interact indirectly only through the intervening tissue/construct disposed within an inner chamber. Two or more tissues in the inner chamber can interact with each other directly or indirectly while being exposed to two different environments. The dimensions of the inserts can be adapted to fit tissue culture containers of any size and shape. Tissues grown in a bioreactor can be exposed to mechano-activating or other damaging forces. A mechano-activating lid assembly can load and test tissue along a vertical axis while maintaining sterility of the system.

Some embodiments allow growth of an anatomic biphasic structure with a functional interface, and allow growth of each tissue type from a single cell source to eliminate possible age/tissue type incompatibility. Some embodiments include individual compartments to constitute separate microenvironments for the different tissue types, such as for the "synovial" and "osseous" components of a microtissue, each being independently accessible to allow introduction of bioactive agents or candidate effector cells. Some embodiments are compatible with the application of mechanical load and perturbation, as well as with imaging capability to allow for non-invasive functional monitoring.

The devices, systems, and methods described herein can be used to study bone-cartilage interaction to investigate OA, although their applicability is not so limited. The devices, systems, and methods disclosed herein can be used to study bone-cartilage interaction to investigate other biological processes or effects, or can be used to study the interaction between other types of tissues.

Also disclosed herein are various microfluidic bioreactor systems that comprise a main body, a base, and cover, with a well being formed within the main body between the base and the cover when the base and the cover are secured to the main body, such that the well configured to contain a biological material. The main body comprises fluidic passageways including a fluid inlet coupled to the well and a fluid outlet coupled to the well, and the fluidic passageways are configured to conduct a fluid flow through the bioreactor such that the fluid flow interacts with a biological material in the well. The cover can provide a viewing aperture that provides external optical access to the biological material in the well when the base and the cover are secured to the main body. In some embodiments, the cover comprises a non-optically transparent plate (e.g., metal or similar material to the main body) having an aperture over the well, and an optically transparent component positioned in, below, or over the aperture in the plate to provide optical access into the well. In some embodiments, the cover comprises an adhesive film that adhesively secures to the main body around an upper end of the well, which can in some cases allow for no additional upper plate needing to be secured to the main body. In some embodiments, the base comprises a mechanical locking feature that enables the base to be secured to the main body (such as via a rotating engagement with mating surfaces in the body of the main body), without screws, bolts, or other additional fasteners.

The foregoing and other objects, features, and advantages of the disclosed technology will become more apparent from the following detailed description, which proceeds with reference to the accompanying figures.

BRIEF DESCRIPTION OF THE DRAWINGS

FIG. 1 shows a schematic, cross-sectional side view of an exemplary bioreactor having a microsystem of plural different tissue types growing therein.

FIG. 2 shows a schematic, cross-sectional plan view of an exemplary bioreactor, a plan view of an exemplary array of bioreactors, and a location of the exemplary bioreactor in the exemplary array of bioreactors.

FIG. 11 shows a schematic drawing of another exemplary system having a plurality of mechanical actuators capable of mechanically activating/stressing tissues within bioreactors and measuring their mechanical properties.

FIGS. 12A and 12B show histology images of exemplary tissues grown according to the techniques described herein, at 10× and 20× magnification, respectively.

FIGS. 13A and 13B show osteoprotegerin IHC images of tissues grown in the absence of endothelial cells, at 10× and 20× magnification, respectively.

FIGS. 14A and 14B show osteoprotegerin IHC images of tissues grown in the presence of endothelial cells, at 10× and 20× magnification, respectively.

FIG. 24B is an exploded side view of the bioreactor of FIG. 24A.

FIG. 28 is a partially exploded perspective view of an exemplary bioreactor system including removable lids and a removable base.

FIG. 29 is a cross-sectional side view of the system of FIG. 28.

FIG. 33 shows a representation of an exemplary bioreactor. Free fluid regions are visualized in grey, the porous medium is red (top). For the localization of boundary surfaces, $\Omega$ and $\Gamma$ indicate volume and surface, respectively (bottom).

FIGS. 60-63 are plots of central fluid flow velocity and hydraulic resistance as a function of channel diameter in the outer ring.

DETAILED DESCRIPTION

Explanation of Terms

Figure 4:
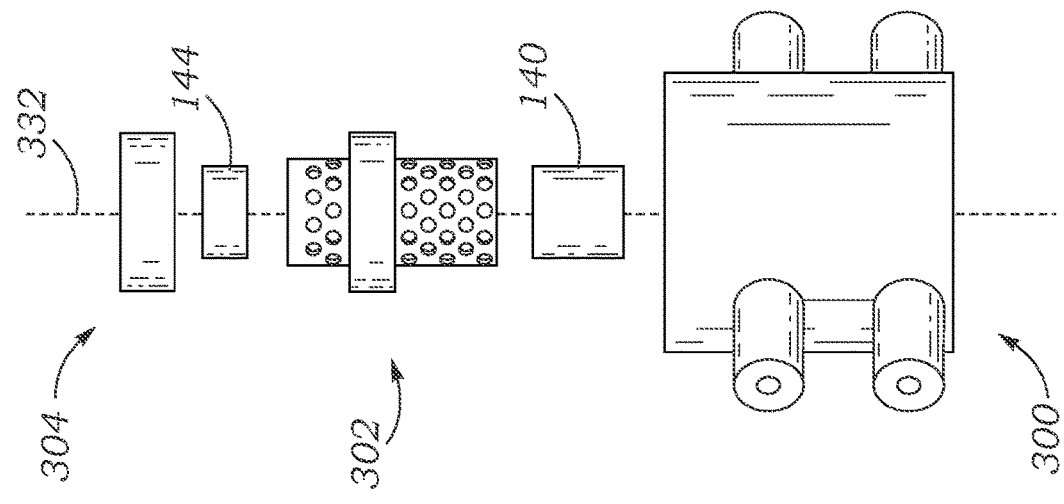
FIG. 4 shows a three-dimensional rendering of the components of an exemplary bioreactor, in an exploded view.

As used herein, "tissue" refers to an aggregation of one or more types of specialized cells united in the performance of a particular function. Organs are formed by the functional groupings of multiple component tissues, hence the tissue may be different types of cells from a particular organ, such as bone. Different tissues can be divided into different categories in several ways, such as based on the embryonic origin of the tissue from ectoderm, mesoderm, or endoderm. Alternatively, the tissue may be a subunit of a physiological system, for example, bone and cartilage in the skeletal system, or an organ, such as dermis and epidermis in the skin, parenchyma and capsule in the liver, sinusoids and parenchyma in the liver, intestinal epithelium and underlying mucosa in the intestine, neurons and myelin in a peripheral nerve, corneal endothelium and epithelium in the eye, renal cortex and medulla in the kidney, and a variety of other distinct but anatomically adjacent tissues that may be found in the body. However, the different tissue types are not confined to normal anatomic tissues but can also include different types of specialized cells found in pathological conditions, such as tumor and adjacent non-tumor tissue of the same or different type, such as adenocarcinoma of the breast and adjacent normal (non-malignant) breast tissue.

As used herein, "chondrocyte" refers to cells found in healthy cartilage, which help to produce and maintain the cartilaginous matrix. As used herein, "osteoblast" refers to the cells responsible for bone formation, which produce and mineralize a matrix of osteoid. A tissue that comprises chondrocytes or osteoblasts is a tissue that contains them, but need not exclusively consist of them. Examples of a tissue that comprises chondrocytes are native cartilage or a culture of chondrocytes as in an artificial cartilage construct. Examples of a tissue that comprises osteoblasts is native bone or a culture of osteoblasts as in an artificial osteoblast construct. As used herein, "matrix" refers to any material disposed between cells. A "matrix" can include any of various suitable biological or synthetic materials. As used herein, "gel" refers to a solid, jelly-like material having a substantially dilute cross-linked structure exhibiting no flow when in the steady state. As used herein, "nutrient" refers to a biological substrate (such as a chemical, vitamin, blood serum, salt, yeast extract, etc.) that a cell requires to live, grow, and/or function, which must be or is advantageously taken from its environment. Examples of other types of nutrients are various carbohydrates, fats, proteins, amino acids, minerals, water, oxygen, and various signaling molecules such as cytokines, growth factors, hormones, and metabolites. A "nutrient fluid" is a liquid that supplies nutrients to living cells, such as a culture medium. Some such media are specialized to support the growth of a particular type of tissue, such as cartilage (cartilage media) or bone (bone media) or the cells contained in such tissue.

As used herein, "OA" refers to osteoarthritis. As used herein, "DMOAD" refers to a disease modifying osteoarthritis drug, which is a subset of a disease modifying drug (DMD).

Tissues that are in "functional contact" with each other need not be in physical contact, but can be separated by an intermediate layer that mediates biochemical communication between the tissues. For example, a layer of mesenchymal stem cells between a layer of chondrocytes and osteoblasts can physically separate them but still permit biochemical communication between the chondrocyte and osteoblast layers.

Exemplary Devices, Systems, and Methods

Engineered tissue constructs which properly incorporate plural tissue layers into an interactive microtissue unit can help in accurately studying biological tissues and their interactions, and can help in elucidating the pathogenesis of various diseases and assessing the efficacy of potential therapeutics against those diseases. Some of the devices, systems, and methods described herein facilitate the growth of physiologically accurate microsystems having distinct biological tissue layers, such as those found within an organ (e.g., the liver) or other physiological system (e.g., the skeletal system). Portions of the current disclosure refer to the osteochondral complex and OA, which are of particular interest herein, although the devices, systems, and methods disclosed should be understood to be applicable to multi-tissue cultures generally.

FIG. 1 shows a cross-sectional view of an exemplary bioreactor 100. Bioreactor 100 includes a shell 102 having a generally cylindrical inner space, as well as an upper inlet 104, lower inlet 106, upper outlet 108, and lower outlet 110. The shell 102 has a closed bottom end 112 and an open top end 114. Several components are situated within the shell 102 in order to facilitate desirable cellular growth therein. For example, the shell 102 encloses an inner body 116 which has a hollow interior 120 and includes a central protruding ring 118 having an outer diameter approximating the inner diameter of the shell 102. The inner body 116 also includes a lower porous screen 124, such as having lateral perforations, and an upper porous screen 126, such as having lateral perforations, each of which can have an outside diameter which is smaller than the inside diameter of the shell 102. Together, the protruding ring 118 and porous screens 124, 126 divide the interior of the shell 102 into an inner lower chamber 128, an outer lower chamber 130, an inner upper chamber 132, and an outer upper chamber 134. Fluids can flow laterally through the upper porous screen 126 between the inner upper chamber 132 and the outer upper chamber 134, and fluids can flow laterally through the lower porous screen 124 between the inner lower chamber 128 and the outer lower chamber 130.

As shown in FIG. 1, the bioreactor 100 can further include an upper ring 136 and a piston 138. The piston 138 can be used to impart a compressive force on materials situated within the bioreactor 100, and the upper ring 136 can form a sealing element between the piston 138 and the shell 102. The upper ring 136 seals the open top end 114 of the bioreactor 100 while allowing the piston 138 to move into and out of the shell 102. Various substances (e.g., nutrients) can flow into the bioreactor 100 through the inlets 104, 106, around or through the inner body 116, and out of the bioreactor 100 through the outlets 108, 110.

Some of the substances entering the bioreactor 100 through inlet 104, for example, can flow around the upper porous screen 126 and out the outlet 108. Some of the media entering the bioreactor 100 through inlet 104 (the amount depending on the characteristics of the components of the system) can also flow laterally through the upper porous screen 126, through cellular tissues growing inside the inner body 116, flow laterally through the opposing side of the upper porous screen 126, and out through outlet 108. Finally, some of the media entering the bioreactor 100 through inlet 104 (again, the amount depending on the characteristics of the components of the system) can also flow through the upper porous screen 126, through cellular tissues growing inside the inner body 116, through the lower porous screen 124, and out through outlet 110. Corresponding flow paths are available for media entering the bioreactor through inlet 106.

This design allows for the provision of different fluids, compounds, and nutrients (e.g., a tissue culture medium or nutrient broth such as serum, or various other growth factors, steroids, growth hormones, etc.), or different concentrations of such materials, to the upper and lower chambers, and thus to different biological tissue layers disposed within the bioreactor 100. In some cases, the specific fluids and nutrients used can be tailored to the particular cell types grown in the bioreactor. For example, in bioreactor 100, hypoxic fluids can be fed through the upper chamber while normoxic fluids are fed through the lower chamber.

FIG. 1 shows that cellular material can be grown in at least 5 separate regions within the bioreactor 100. As shown, an osteoblast construct 140 can grow in the inner lower chamber 128, a mesenchymal construct 142 can grow on top of the osteoblast construct 140, and a chondrocyte construct 144 can grow on top of the mesenchymal construct 142. The chondrocyte construct 144 can be exposed to the piston 138 or a layer of synovial fluid can separate the chondrocyte construct 144 from the piston 138, and in either case, the piston 138 can be actuated to impart forces through the chondrocyte construct 144, the mesenchymal construct 142, and the osteoblast construct 140 to the bottom end 112 of the shell 102. Further, a layer of endothelial cells 146 can grow on the exterior of the lower porous screen 124, and a layer of human fibroblast cells 148 can grow on the exterior of the upper porous screen 126.

FIG. 2 shows a cross sectional plan view of the bioreactor 100 and its location within an exemplary array 200 of ninety six bioreactors 100. FIG. 2 shows that plural bioreactors 100 can be arranged in an array 200 such that the outlets of some bioreactors are fluidly coupled to the inlets of other bioreactors. For example, the outlets 108, 110 of bioreactor 100a are coupled to the inlets 104, 106 of bioreactor 100b, respectively, and the outlets 108, 110 of bioreactor 100b are coupled to the inlets 104, 106 of bioreactor 100c, respectively. Thus, a plurality of bioreactors 100 can be coupled in series to facilitate distribution of substances through them. Additionally, a plurality of series 202 of multiple bioreactors 100 can be arranged adjacent one another to form the array 200. The plurality of series 202 can be fluidly coupled either in series or in parallel with one another.

Figure 3:
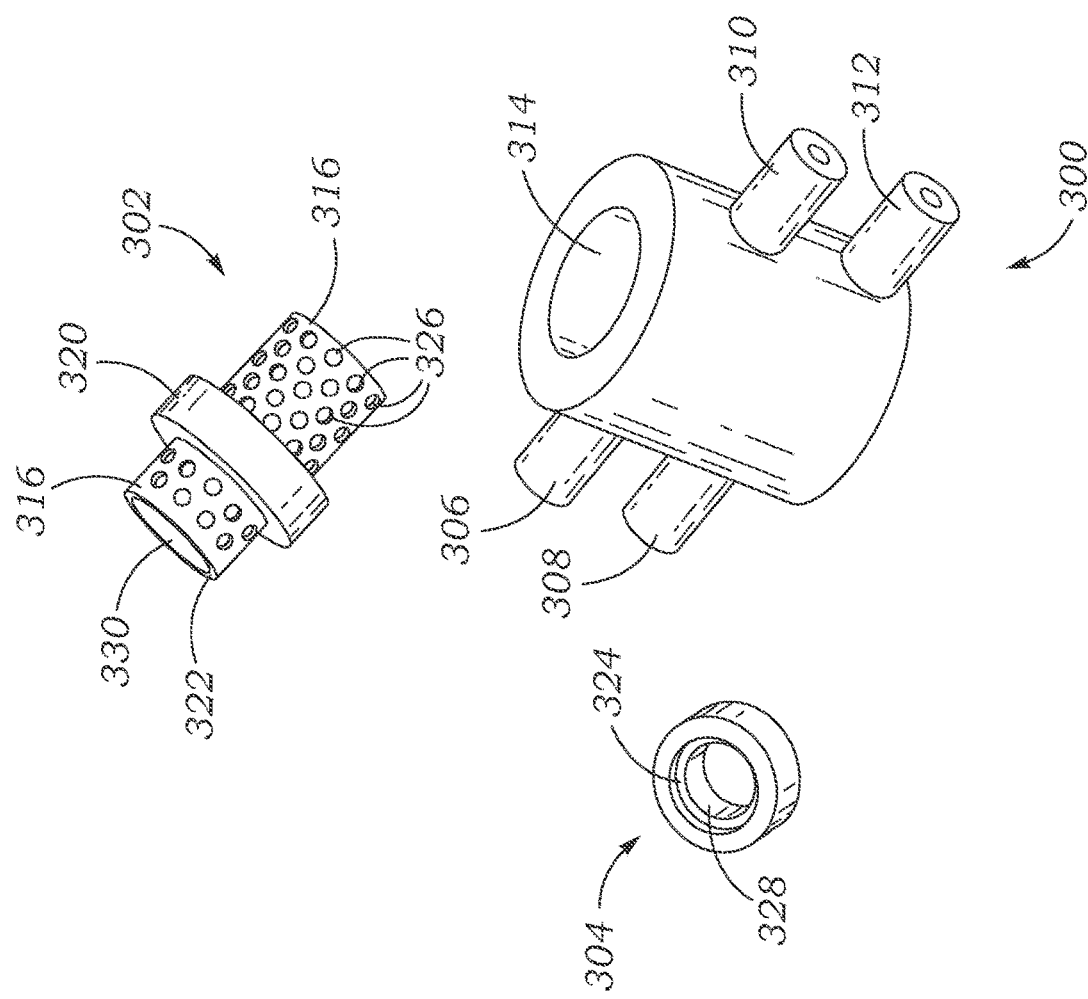
FIG. 3 shows three-dimensional renderings of an exemplary shell of a bioreactor, inner body of a bioreactor, and upper ring of a bioreactor, in perspective views.

FIG. 3 shows an exemplary shell 300, exemplary inner body 302, and an exemplary upper ring 304. The shell 300 has an overall hollow cylindrical shape, and comprises an upper inlet 306, a lower inlet 308, an upper outlet 310, and a lower outlet 312, each of which comprises a hollow, generally cylindrical extension extending radially outwardly from the shell 300. The shell 300 also includes a hollow, generally cylindrical inner space 314 within which the inner body 302, upper ring 304, and cellular material can be situated. The inner body 302 includes a lower porous screen 318 and an upper porous screen 316, both of which include a plurality of pores, or small openings, 326. The inner body 302 also includes a protruding ring 320 which protrudes radially outwardly from the rest of the inner body 302, and which has an outside diameter approximating the inner diameter of the inner space 314. Thus, when the inner body 302 is situated within the shell 300, several distinct chambers can be formed, as described herein with regard to bioreactor 100.

FIG. 3 also shows that upper ring 304 has a groove 324 extending around the circumference of the inner surface of one end of the upper ring 304. The upper ring also has a main inner surface 328 having a generally cylindrical shape and an inner diameter approximating an inner diameter of the inner cylindrical space 330 in the inner body 302. FIG. 4 shows the exemplary shell 300, inner body 302, upper ring 304, chondrocyte construct 144, and osteoblast construct 140, aligned along axis 332 in an exploded view. These elements can be combined, together with a mesenchymal construct (not shown) to form a bioreactor similar to bioreactor 100. When these components are assembled to form a bioreactor in this manner, the osteoblast construct 140, mesenchymal construct, and chondrocyte construct 144 are situated within the inner space 330 within the inner body 302. Further, a top end portion 322 of the inner body 302 can be situated within the groove 324 of the upper ring 304 to facilitate sealing of the system (note a similar structural configuration in FIG. 1—a top end of the upper porous screen 126 is situated within a similar groove at the bottom end portion of the upper sealing ring 136).

Figure 5A:
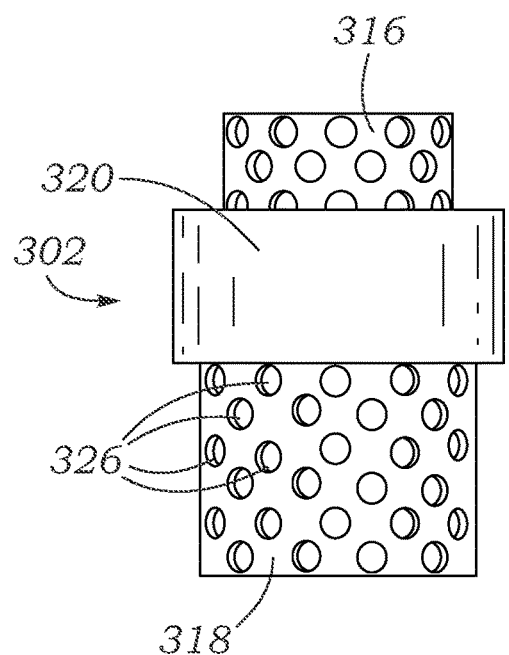
FIGS. 5A-5B show three-dimensional renderings of exemplary inner bodies for use in bioreactor systems, from two different views.
Figure 5B:
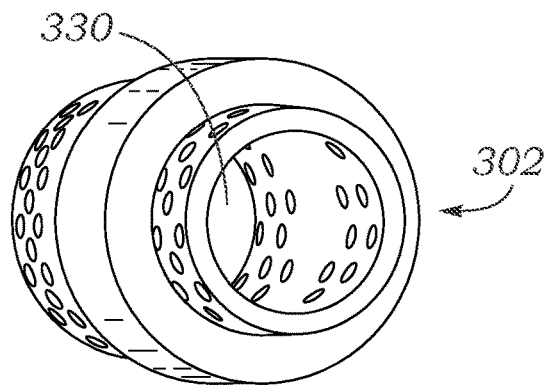
Figure 5C:
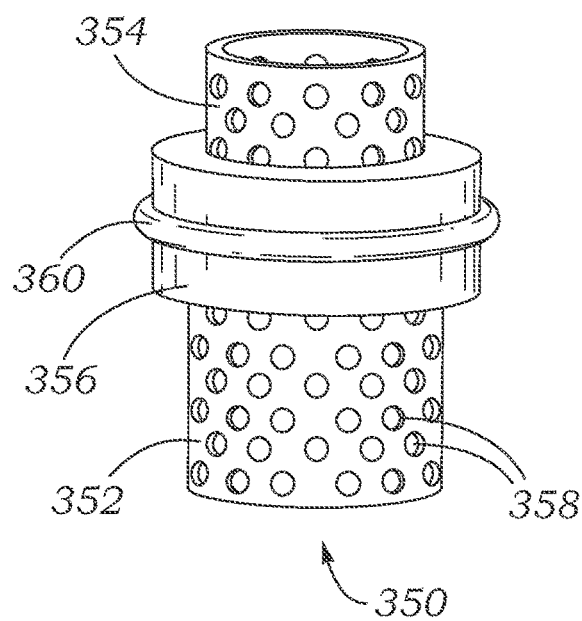
FIGS. 5C-5D show photographs of exemplary inner bodies for use in bioreactor systems, from two different views.
Figure 5D:
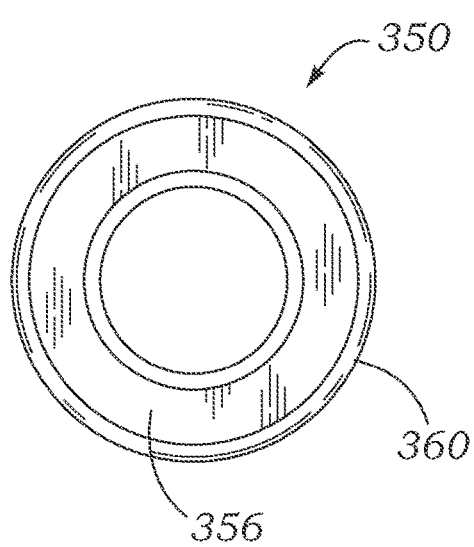

FIGS. 5A-5B show alternate views of the inner body 302 shown in FIGS. 3-4. FIG. 5B shows that the inner body 302 has a cylindrical inner open space 330 which spans through the entire body 302 to accommodate the positioning of cellular material therein. FIGS. 5C-D illustrate an inner body 350 comprising a lower porous screen 352, an upper porous screen 354, and a protruding ring 356. The lower and upper porous screens have a plurality of pores 358. The inner body 350 also includes a sealing o-ring 360 disposed around the outside of the central protruding ring 356. The o-ring 360 helps seal the inner body 350 against the inner surface of a shell (e.g., shell 102) to more effectively maintain distinct chambers within the shell. The inner body 350 can be fabricated, for example, photolithographically using a biocompatible plastic-polymer. In some embodiments, the shell, body and/or ring of an inner body, or other parts of a bioreactor, can be fabricated with commercially available E SHELL 300™ polymer resin using photo-stereolithography (PSL).

Figure 5E:
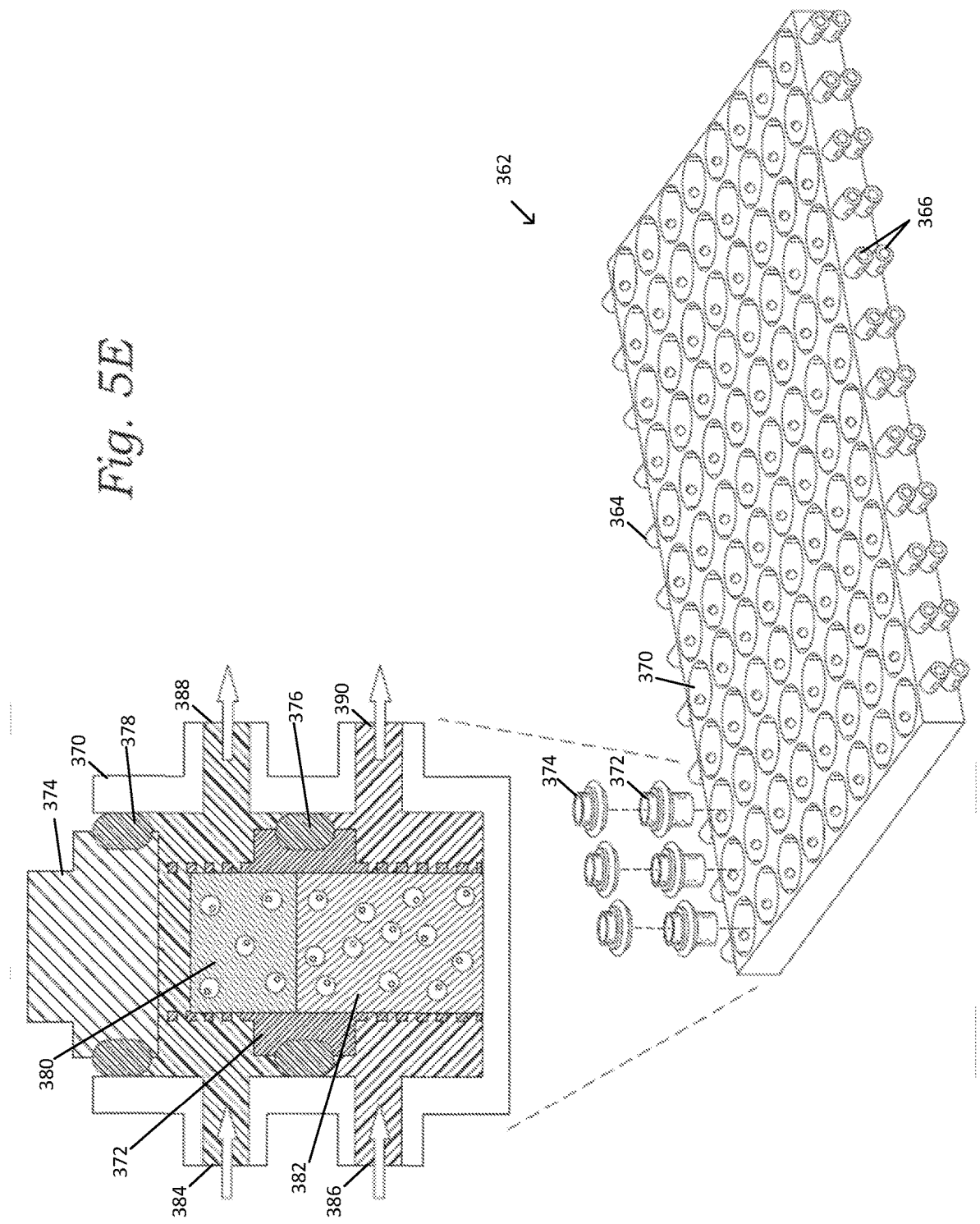
FIG. 5E is a schematic representation of a multiwell, dual chamber bioreactor system, with a 96 well bioreactor platform shown on the right, and a cross-sectional view of a single bioreactor on the left.

FIG. 5E is a schematic representation of a multiwell, dual chamber bioreactor system, with a 96 well bioreactor platform 362 shown at the lower right, and a cross-sectional view of a single bioreactor shown at the upper left. The multi-well platform 362 includes a plurality or rows of eight wells 370 that are in fluid communication from one inlet/outlet pair 364 across the row of wells 370 to an opposite inlet/outlet pair 366. Each well 370 is configured to receive a bioreactor insert 372 and a sealing lid 374 (the lid can be replaced with and/or incorporated into a mechanical actuator or piston that applies a mechanical loading pattern downward on the tissue/fluid in the bioreactor). The insert 372 is sealingly engaged with the inner surfaces of the well 370 via an o-ring 376 to form separate upper and lower fluid flow chambers. The lid 374 is also sealingly engaged with the inner surfaces of the well 370 via another o-ring 378 to prevent fluid escaping from the well. The insert 372 can contain at least two layers of biological material, such an upper layer 380 and a lower layer 382 as shown. The upper layer 380 can comprise a chondral construct and/or the lower layer 382 can comprise an osseous construct, for example. One or more additional layers, such as an intermediate layer, can also be included. An intermediate mesenchymal layer can be included, for example. Each well has two opposing upper inlet/outlets 384 and 388, which allow a first fluid to flow through the upper chamber to interact with the upper layer 380, and two opposing lower inlets/ outlets 386, 390, which allow a second fluid to flow through the lower chamber to interact with the lower layer 382. The first fluid can comprise a chondrogenic medium and/or the second fluid can comprise an osteogenic medium, for example.

As illustrated in FIG. 5E, the first fluid can enter at 384 and then pass laterally through perforations in the insert 372 to enter the upper layer 380 laterally. The first fluid can then exit the upper layer 380 laterally through the perforations in the insert 372 before exiting the bioreactor at 388. The perforations can extend circumferentially around the insert 372 such that the first fluid can flow around the upper layer and can interact laterally with the upper layer from all lateral sides. Some of the first fluid can also flow over the top of the upper layer and perfuse into and out of the upper layer from its upper surface. Similarly, the second fluid can enter at 386 and then pass laterally through perforations in the lower portion of insert 372 to enter the lower layer 382 laterally. The second fluid can then exit the lower layer 382 laterally through the perforations in the insert 372 before exiting the bioreactor at 390. The perforations can extend circumferentially around the lower portion of the insert 372 such that the second fluid can flow around the lower layer and can interact laterally with the lower layer from all lateral sides.

Figure 6A:
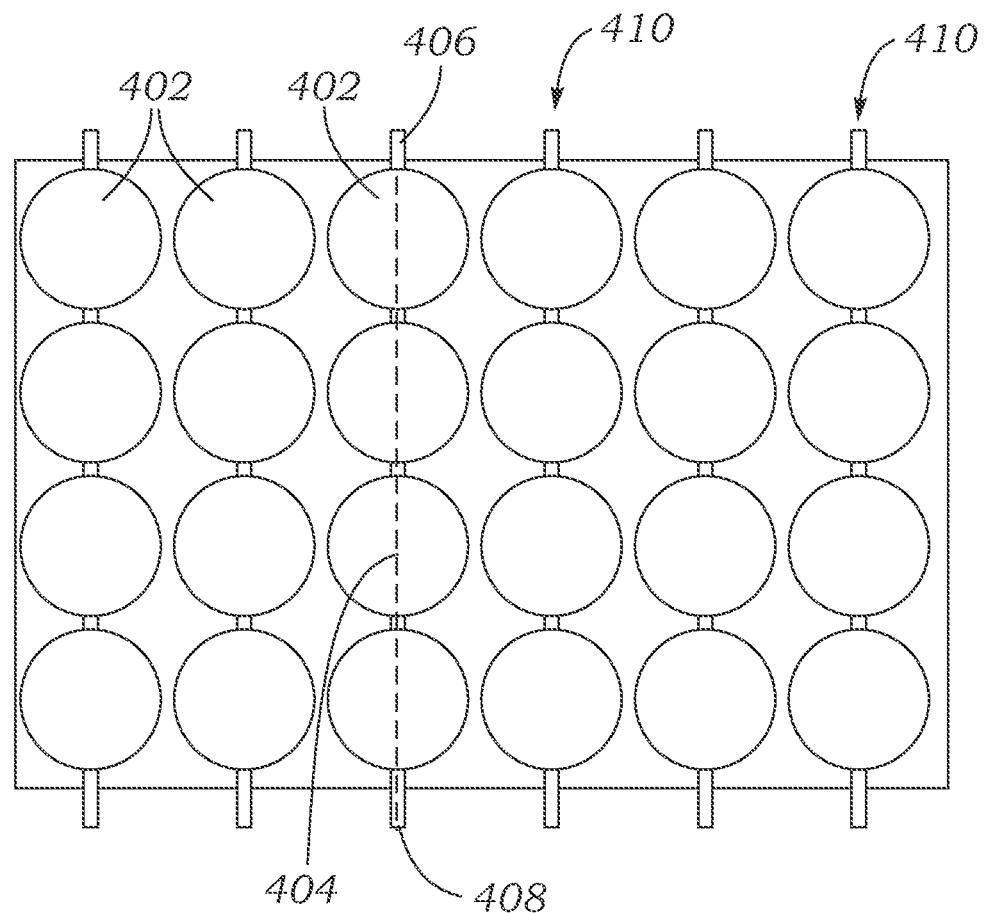
FIG. 6A shows a schematic plan view of an exemplary well plate having an array of wells therein, within each of which a bioreactor inner body can be situated, as well as a plurality of flow paths through the well plate.
Figure 6B:
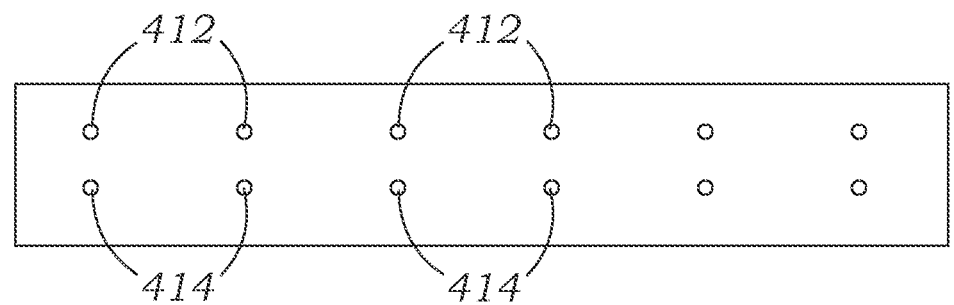
FIG. 6B shows a schematic side view of the well plate of FIG. 6A, including a plurality of upper ports and a plurality of lower ports.

FIG. 6A illustrates in plan view an exemplary array 400 of wells 402, within each of which an insert such as insert 350 can be situated. The array 400 of wells 402 includes six sets 410 of four wells 402 fluidly coupled in series. Thus, a flow path through four wells 402 is illustrated as conduit path 404, along which fluids can flow either from a first end 406 to a second end 408 or from the second end 408 to the first end 406. Thus, the first end 406 can be either an inlet or and outlet, and the second end 408 can be either an inlet or an outlet, depending on the direction of flow along the conduit path 404. FIG. 6B illustrates the array 400 from a side view, showing that each set 410 of wells 402 can have both an upper port 412 and a lower port 414 for carrying fluids into or out of the set 410 of wells 402, depending on the direction of flow along the conduit path 404.

Figure 7:
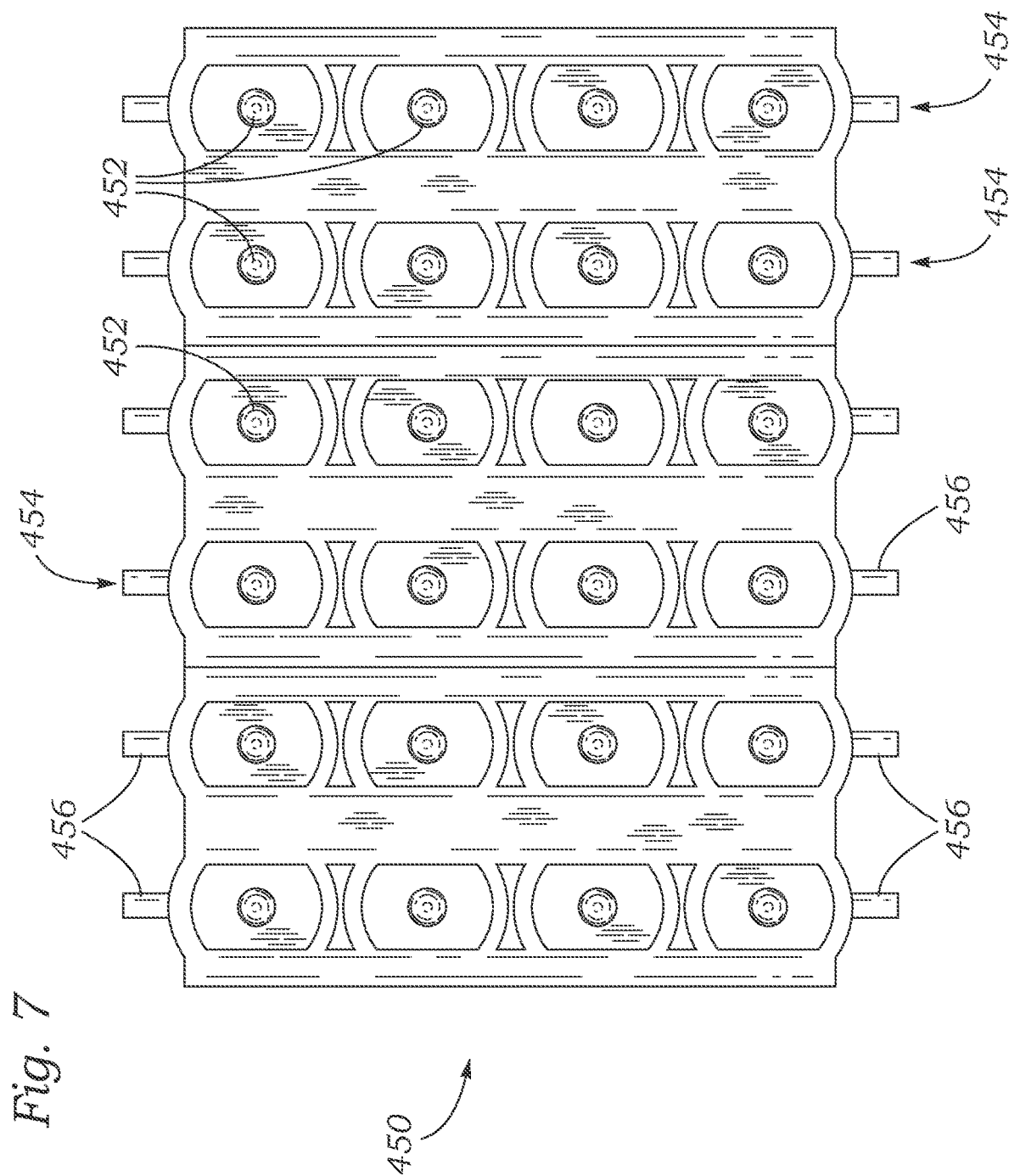
FIG. 7 shows an image of an exemplary array of 24 bioreactors, from a top plan view.

FIG. 7 shows an array 450 of wells 452 similar to the array 400, with twenty-four wells 452 each having an integrated well insert. The wells 452 are arranged in six sets 454 of four wells 452 fluidly coupled in series. Each of the six sets of wells 452 is provided with a port 456 at each end, through which fluid can either enter or exit, depending on the flow path through the set 454 of wells 452.

In some embodiments, systems capable of mechanically stressing the cellular material grown in a bioreactor are desirable. Natural bone and cartilage growth is known to be affected by mechanical stresses encountered by those tissues as they grow, thus systems allowing the introduction of such stresses can facilitate tissue growth which more accurately resembles native tissue growth. Accordingly, FIGS. 8-11 illustrate several systems capable of mechanically stressing tissues as they grow in a bioreactor such as the bioreactor 100 described herein.

Figure 8A:
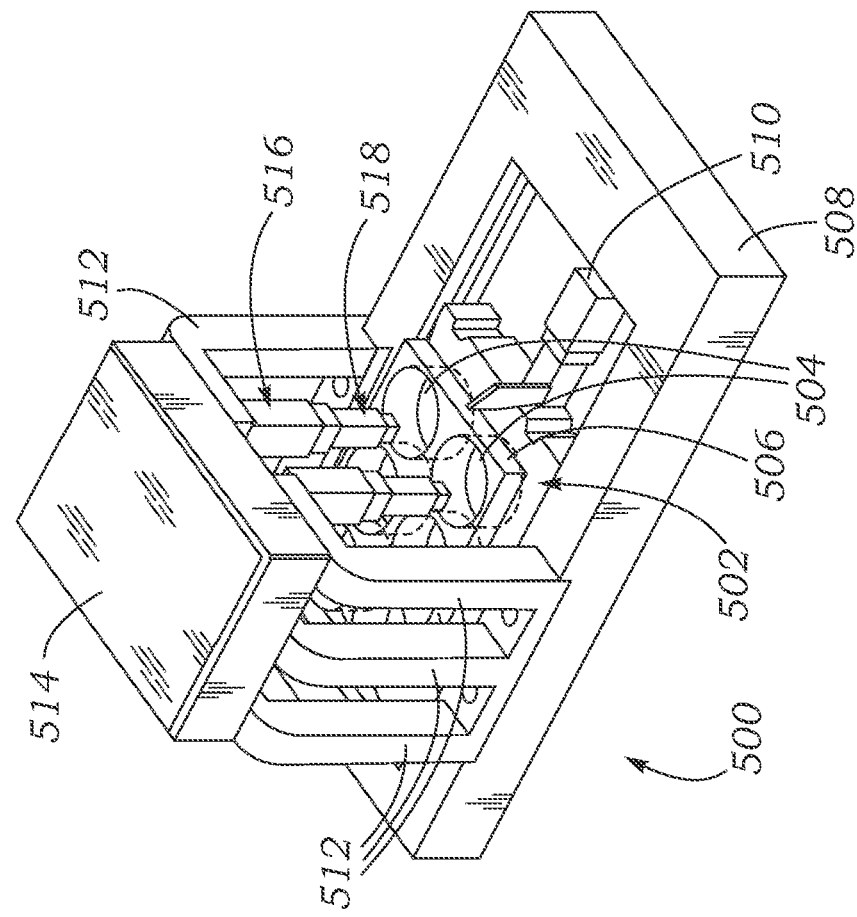
FIG. 8A shows a schematic drawing of an exemplary system having a plurality of mechanical actuators capable of mechanically stressing tissues within bioreactors or laboratory plates.
Figure 8B:
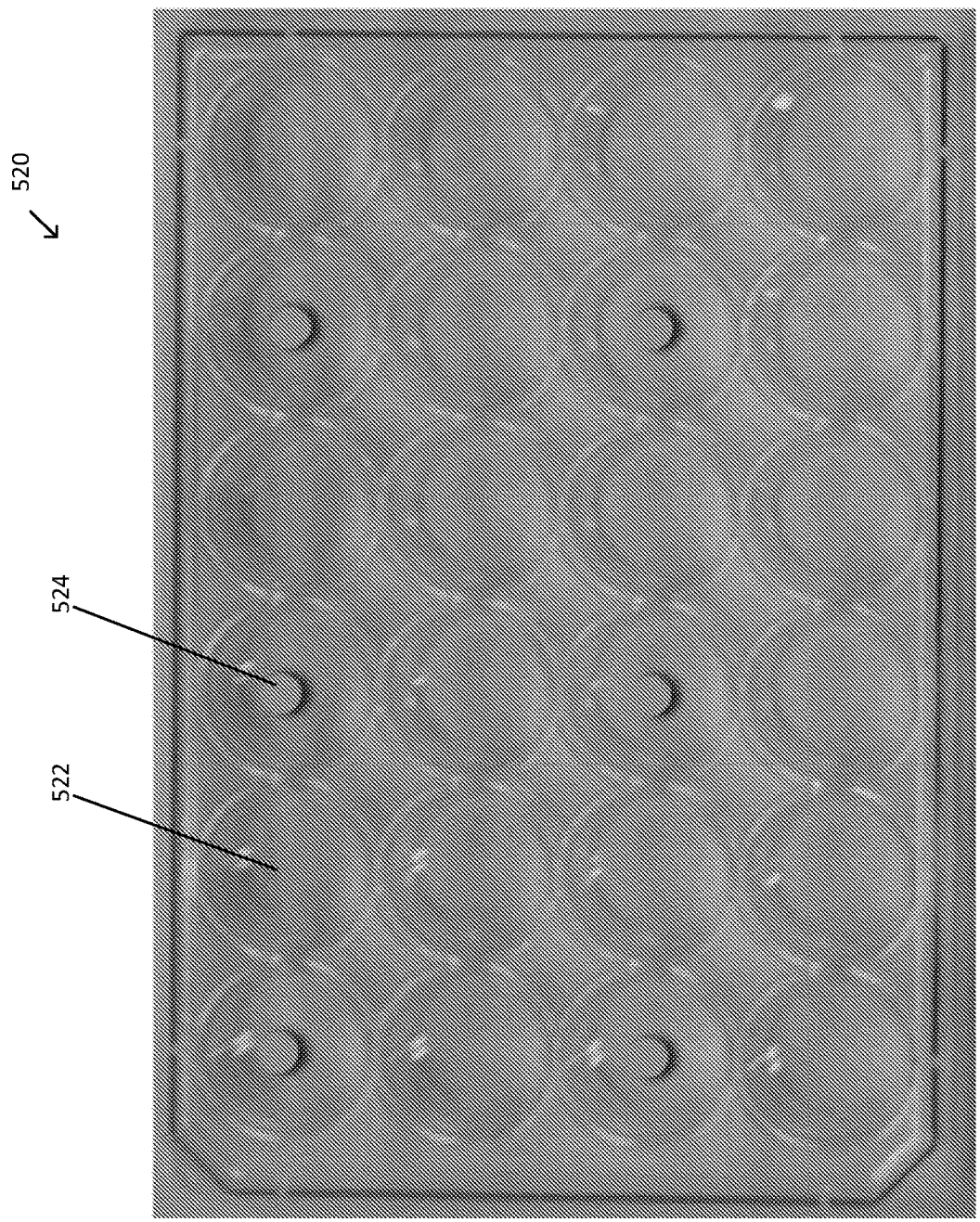
FIG. 8B illustrates an exemplary method of imparting an array of bioreactors with loading forces in groups of six at a time.

FIG. 8 shows an exemplary system 500 comprising an array 502 of six bioreactors 504, which can have various configurations but in one specific embodiment can be similar to the bioreactor 100. The array 502 can be situated on a mount 506 which can be horizontally slidable relative to a base plate 508. The mount 506 can be actuated to move horizontally relative to the base plate 508 using a sliding actuator 510. The system 500 also includes a set of vertical extension arms 512 rigidly coupled to the base plate 508, and an actuator housing 514 rigidly coupled to the extension arms 512. The actuator housing 514 houses six micromechanical actuators 516, which can be used to impart forces to the bioreactors 504. The actuators 516 can also include force sensors 518 to monitor the force being imparted to ensure that sufficient, but not excessive, force is imparted to the bioreactors 504 and the tissues grown therein.

The system 500 can be modified to allow the six actuators 516 to mechanically stress more than six bioreactors 504. For example, additional bioreactors 504 can be situated on the mount 506 and can be moved under the actuators 516 by action of the sliding actuator 510. Thus, the actuators 516 can be used to sequentially stress tissues in a larger number of bioreactors. In other embodiments, a second sliding actuator can be used to make the mount 506 slidable along two perpendicular axes. Thus, the actuators 116 can be used to induce stresses in tissues in bioreactors of an array having a larger number of bioreactors 504 in two dimensions.

FIG. 8A illustrates an exemplary method in which a multi-well tray of bioreactors can be sequentially stressed with loading forces in groups. For example, the tray 520 contains 24 bioreactors in a 4-by-6 array of wells 522. A mechanical loading apparatus, similar to that described in FIG. 8, can apply loading forces to groups of six of the bioreactors at a time. An exemplary group of six is represented by the six dots 524. After providing loading forces on the group of six represented by the dots 524, the tray 520 and/or the loading mechanism can be shifted such that a different group of six wells 522 and bioreactors is positioned below the six loading members of the loading mechanism. This can be repeated until all 24 bioreactors are imparted with loading forces. In this way, the total of 24 bioreactors can be imparted with loads in four sessions, with six bioreactors being imparted with loading forces in each of the four sessions. FIG. 8A illustrates just one exemplary loading pattern. In other loading patterns, groups of different numbers and/or arrangements of bioreactors can be included in each loading session.

Figure 9:
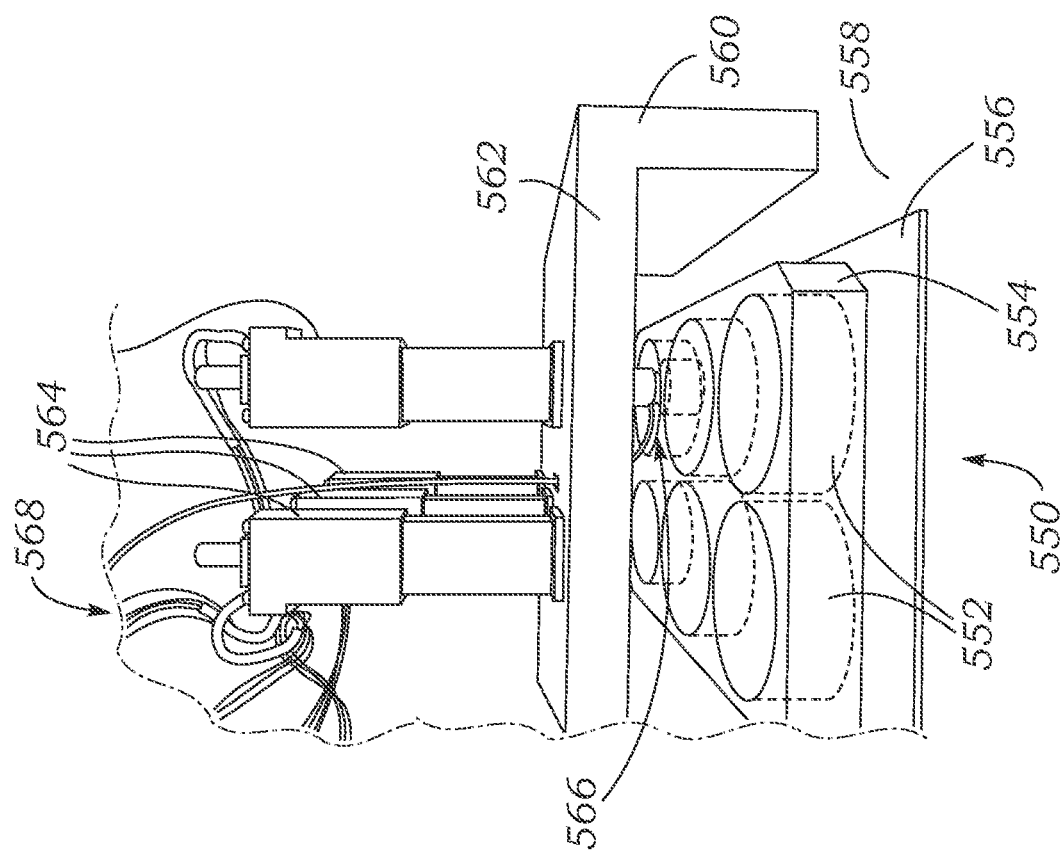
FIG. 9 shows a photograph of another exemplary system having a plurality of mechanical actuators capable of mechanically activating/stressing tissues grown in bioreactors and measuring their mechanical properties.

FIG. 9 shows a side view of an exemplary system 550 comprising six bioreactors 552 housed in a container 554, the container 554 situated on a tray 556 resting on a rigid surface 558. FIG. 9 also shows that supports 560, resting on the rigid surface 558, support an actuator support platform 562, on which six micromechanical actuators 564 are mounted. As in system 500, system 550 can be used to mechanically stress tissues grown in the six bioreactors 552 situated below the actuators 564. As in system 500, force sensors 566 can be coupled to the actuators 564 to measure the forces imparted by the actuators, to ensure sufficient, but not excessive, force is imparted to the tissues in the bioreactors 552. Wiring 568 can be used to couple the actuators to a controller unit such as a computer (not shown). The controller unit can be used to control the forces exerted by the actuators and to monitor force readings from the force sensors 566.

Figure 10:
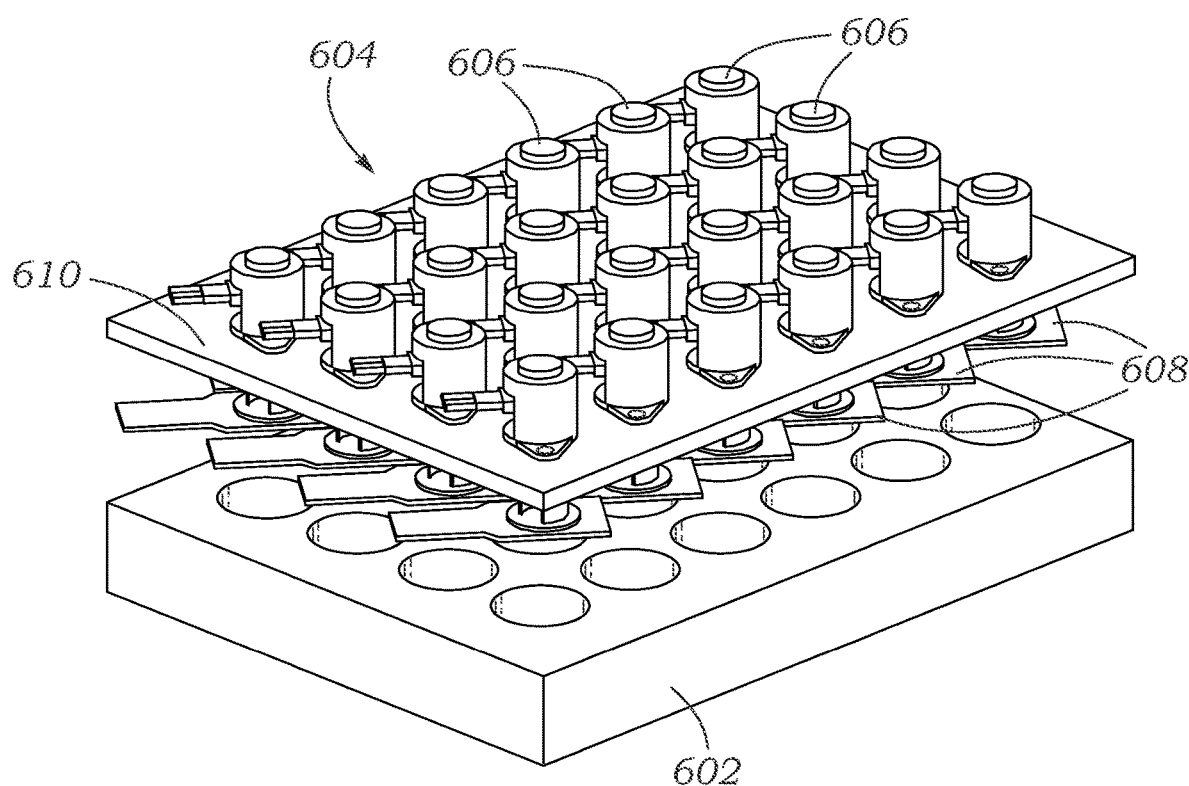
FIG. 10 shows a schematic drawing of another exemplary system having a plurality of mechanical actuators capable of mechanically activating/stressing tissues within laboratory multiwell plates and measuring their mechanical properties.

FIG. 10 shows another exemplary system 600 including a twenty-four well plate 602 and a mechanical stimulator lid assembly 604. The well plate 602 comprises twenty four wells, within each of which a bioreactor (e.g., bioreactor 100) can be situated. An inner body (e.g., an inner body similar to inner body 116) having a protruding ring and being configured to be situated within a well of the well plate 602 can have at least one vertical channel formed in its protruding ring, which channel can be configured to accommodate a pipe or tube which can carry fluid from the lower chamber of a first bioreactor, over the wall between adjacent wells of the well plate 602, and to the lower chamber of a second bioreactor adjacent to the first bioreactor. The mechanical stimulator lid assembly 604 comprises twenty-four micromechanical actuators 606 and twenty-four respective force sensors 608 with associated pistons. The actuators 606 and the sensors 608 are mounted on a support plate 610. As in previous embodiments, the actuators 606 can be used to mechanically stress tissue growing in bioreactors situated in the wells of the well plate 602.

FIG. 11 shows another exemplary system 650 similar to system 600. System 650 includes a twenty four well plate 652 comprising twenty-four wells 654, and a mechanical stimulator lid assembly 656 comprising twenty four micromechanical actuators 658 and twenty-four force sensors 660 mounted on a support plate 662. Additionally, FIG. 11 shows upper inlets 664, lower inlets 666, upper outlet 668, and lower outlet 670.

In some embodiments, mechanical actuation or perturbation of tissues in a bioreactor, as described herein, can comprise a "gentle" application of load, for instance <10% strain for 1 hour a day, that mimics the general mechanical environment of the joints without causing damage, and it generally promotes the production and maintenance of better tissue. In other embodiments, mechanical actuation or perturbation can comprise >10% strain that can induce a response similar to an injury response.

The devices, systems, and techniques so far described can be used to facilitate the growth of different tissues, such as tissue found in an organ, for example, an osteochondral microtissue construct from bone. The proposed construct (shown for example in FIG. 1) involves a layered osteochondral tissue composite including, from bottom to top: bone, osteochondral interface, cartilage, and synovium, cultured within a perfusion-ready container mold. As described elsewhere herein, the bone construct can be peripherally surrounded by endothelium to simulate the biological effects of blood vessels and the vasculature on OA. The endothelium can in some cases extend from its location shown in FIG. 1 to form capillary-like structures within the osteoblast construct. Culture-expanded human vascular endothelial cells can be used to form the endothelial lining. The cartilage construct can in some cases also be peripherally surrounded by endothelium, or, as shown in FIG. 1, can be surrounded by human fibroblast (hf) material. Such a layer of hf material can help to simulate interstitial cellular material present in many tissues, for example, the inner lining of the synovial cavity.

Endothelial cells release factors such as fibroblast growth factors (FGFs), interleukin-1β (IL-1β), and interleukin-6 (IL-6), and nitric oxide (NO) which influence both bone and osteoclast behavior, thereby regulating bone formation and resorption. In particular, endothelial cells provide a robust source of bone morphogenetic protein-2 (BMP-2) which enhances the osteogenic phenotype in bone and bone-progenitor cells. In turn, endothelial cells are the target of many bone-derived signals, such as parathyroid hormone (PTH), insulin-like growth factors types 1 and 2 (IGF-1 and IGF-2), basic fibroblast growth factor (bFGF), platelet derived growth factor (PDGF), and vascular endothelial cell growth factor (VEGF).

Each type of tissue used in the devices, systems, and methods described herein can be formulated with the use of scaffold crosslinking technologies, such as projection stereolithography (PSL) to incorporate internal 3D spatial features which permit optimal tissue formation and medium perfusion. For example, 500-micron-diameter channels can be fabricated within the bone construct to aid in nutrient dispersion throughout the construct. Bone can be formed by seeding and culturing MSCs in photocrosslinked collagen/hydroxyapatite. Collagen and hydroxyapatite, or $Ca_{10}(PO_4)_6(OH)_2$, are primary components of bone, and both are frequently used in tissue engineered bone constructs. Cartilage can be engineered by seeding MSCs in a photo-activated/crosslinked polymeric gel, such as a collagen/chitosan gel, and treated with TGF-β3. Chitosan can be advantageous, as it shares some structural characteristics with glycosaminoglycans, a critical component of cartilage responsible for many of its specific mechanical properties. With its many primary amine groups, chitosan can also aid in collagen crosslinking.

Osteochondral interfaces can be formed from a variety of cellular and other materials arranged in various combinations with one another. An exemplary osteochondral interface can be formed by placing a layer of MSC-laden collagen type I hydrogel between the chondral and osseous layers. The synovial lining can be generated with MSCs seeded in crosslinked polyethylene glycol alone and cultured in non-inductive medium. These conditions have been shown in preliminary experiments to be capable of maintaining a fibroblastic phenotype in MSCs. As previously mentioned, the endothelial component can comprise endothelial cells embedded in collagen to surround the osteochondral elements. Collagen gels can be selected based on their susceptibility to modification and contraction by endothelial cells and osteoblasts, which can result in a tight fit around the osteoblast construct.

As there are limited differentiated cell sources available for cartilage and bone tissue engineering, adult multipotent mesenchymal stem cells (MSCs), with their well-characterized ability to differentiate into chondrocyte- and osteoblast-like cells, represent an advantageous candidate cell source for engineering these tissues. Human MSCs derived from bone marrow or from adipose (lipoaspirate) can be used as the progenitor cell population to engineer the bone, cartilage, and synovium components of the microtissue. However, the microtissue system described herein is compatible with constructs derived from any type of progenitor or primary cell. Indeed, induced pluripotent stem cells, with their ability to be propagated to meet the high cell requirements of tissue engineering, represent an attractive, high-quality cell source and provide one exemplary alternative source.

Bioreactor designs can include two separate circulating feeding/delivery systems, such as those shown in FIG. 1 including lower chambers 128, 130 and upper chambers 132, 134, which may be mixed if desired. A first system (e.g., chambers 132, 134) can supply an upper "synovial compartment" and can be separated by an upper screen (such as upper porous screen 126) having 20 µm pores, which in some cases can include a 0.2 µm filter lining. An outer surface of the upper screen can be layered with endothelial cells which adhere thereto and develop after the cells are delivered by perfusion once the construct is assembled. The inner surface of the screen can be lined with a collar of MSC-embedded photo-polymerized hydrogel to constitute the synovium. A second system (e.g., chambers 128 and 130) can supply the bony tissue construct and can be separated from the bone with a rigid wall (e.g., lower porous screen 124) with ≥20 µm pores, thus delivering nutrients as well as allowing endothelial cells and other cells to adhere to and migrate into the bony tissue and create new biologically relevant niches.

As described above, bioreactor systems can include mechanical loading mechanisms. In one exemplary design, the loading device includes a 3 mm loading surface having an unloaded position <0.5 mm from the cartilage surface, and is configured for loading of 5% strain (100 µm) at 0.1

Hz. Reports in the literature suggest that this combination of strain and loading rate should be chondro-stimulatory in engineered cartilage constructs. Furthermore, extreme loading can be applied in conjunction with stimulation by biochemical stresses to simulate physical injury within the microtissue system. In alternative embodiments, the mechanical loading can be force- or stress-driven rather than strain-driven.

One aspect of the microtissue described herein is its ability to mimic the tissue relationships within the osteochondral complex of the articular joint and to characterize responses to mechanical, toxicological, pathological and inflammatory insults or perturbations. The application of the devices, systems, and methods described herein toward these types of studies can proceed according to several steps. First, behavior of the microtissue grown using the devices, systems and methods described herein can be validated under non-stressed conditions to confirm proper matrix production, differentiation marker expression, and tide mark development. Second, the system can be perturbed with mechanical, chemical, and/or toxicological stresses, insults, or perturbations to demonstrate that the microtissue responds according to published in vivo studies.

Third, once validated, the system can be used to investigate biological process not easily studied by traditional means. For example, to study the effects of mechanical injury, the cartilage component can be pre-injured prior to microtissue assembly to study the effects of damaged cartilage on bone health. Alternatively, the assembled and matured microtissue can be impacted to study changes in cartilage and bone anabolic/catabolic pathways and disruption of the tidemark. Similarly, the microtissue system can be employed as a high-throughput in-vitro model to assess the effects of treatment with glucocorticoids, pro-inflammatory cytokines, anti-inflammatory biologics, even biomaterial wear debris, such as titanium and polyethylene microparticles, on osteochondral health. Microtissue systems grown using the devices, systems, and methods described herein offer novel capabilities for investigating the pathogenic mechanisms of OA as well as serving as a high-throughput platform to test candidate DMOADs.

In some methods for developing functional endochondral microtissue, the components of a bioreactor platform (such as including a shell, inner body, upper ring, and other components, similar to those of bioreactor 100) can initially be fabricated, and then the platform design and integrity can be verified using, e.g., structural and media (pH, oxygen, etc.) tests.

In some methods, undifferentiated MSCs can initially be isolated, and then some of them can be pre-differentiated into osteoblasts and chondrocytes. MSC differentiation can then be verified using, e.g., histological and reverse transcription polymerase chain reaction ("RT-PCR") techniques. In some embodiments, undifferentiated MSCs can be encapsulated in a collagen type 1 gel to form a mesenchymal construct. Undifferentiated MSCs can also be encapsulated in PEG to form a synovium. Pre-differentiated osteoblasts can be encapsulated in hydroxyapatite-containing collagen type 1 gel to form an osteoblast construct. Pre-differentiated chondrocytes can be encapsulated in a collagen type 1/chitosan gel to form a chondrocyte construct. Separately, endothelial cells can be isolated and encapsulated in a collagen type 1 gel to form an endothelium. While specific examples of suitable gel matrices are provided herein for exemplary purposes, various other suitable gels are available for use with the various cellular materials. In some embodiments, biological tissues can be used as an alternative to gel matrices for suspending the cellular material.

The various microtissue cellular components thus formed (e.g., mesenchymal construct, synovium, osteoblast construct, chondrocyte construct, and endothelium) can then be verified for viability and tissue type, using, e.g., 3-(4,5-dimethylthiazol-2-yl)-5-(3-carboxymethoxyphenyl)-2-(4-sulfophenyl)-2H-tetrazolium ("MTS"), Live/Dead staining, and/or histology/immunohistochemistry ("IHC") techniques.

The components of a fabricated bioreactor platform can then be combined with these and/or other microtissue cellular components to assemble a bioreactor similar to bioreactor 100. Performance of the microtissues in the bioreactor can then be verified using, e.g., leakage tests, micro computed tomography ("mCT"), magnetic resonance imaging ("MRI"), MTS, Live/Dead, imaging, and/or histology/IHC techniques.

In some embodiments, a mechanical loading system can be provided that is configured to provide a physiological load to the tissue in the bioreactor. Such a loading system can then be verified using, e.g., mCT, MRI, histology/IHC, or imaging techniques.

In some embodiments, the microtissues in a bioreactor can be treated with various insults, such as mechanical, chemical, toxicological, and/or biological insults or perturbations. For example, the microtissue can be mechanically injured by providing a pathogenic load, and the microtissue response can then be measured. As another example, bone pathology can be investigated by treating an osteoblast construct with glucocorticoids and measuring the microtissue response. As yet another example, bone inflammation can be investigated by treating an osteoblast construct with pro-inflammatory cytokines (e.g., TNF-$\alpha$, etc.) and measuring the microtissue response. As another example, bone exposure to particulates can be investigated by treating an osteoblast construct with titanium microparticles and measuring the microtissue response. As another example, the microtissues can be exposed to any of various implant wear debris, such as microparticles of ultra-high-molecular-weight polyethylene (UHMWPE), titanium, chromium/cobalt, etc., and the microtissue response can be measured. As another example, the microtissues can be exposed to various cells, such as cells typical of an inflammatory environment, and the microtissue response can be measured. In each of these examples, the microtissue response can be measured using, e.g., ELISA, imaging, histology/IHC, mCT, MRI, or matrix metalloproteinases ("MMP") activity techniques.

In some embodiments, cartilage health can be tracked based on gene expression activities, e.g., using adeno-associated virus (AAV)-based tissue-specific promoter-reporter constructs.

While portions of the present disclosure have been directed to the growth and study of bone and cartilage tissues, the devices, systems, and methods disclosed herein are applicable to various other biological tissues and structures. For example, the bioreactors and methods described herein can be used to facilitate the growth and/or study of any set of tissues, particularly a set of tissues in which interactions between the different tissues are suspected or known to exist and are a target for study. For example, a single layer of tissue or combinations of two, or three, or four, or five, or more layers of different tissues can be studied using the devices, systems, and methods disclosed herein. Specific examples include an osteochondral complex and chondrocyte complex without a mesenchymal complex, and various other examples provided herein.

Further, either as a substitute for or in addition to an MSC layer, in some cases, a membrane having any of various suitable pore sizes can be situated between any of various tissue layers being cultured in a bioreactor. For example, the membrane could take the place of an MSC layer as described elsewhere herein. Further, except where structurally impossible, any of the devices, systems, and components thereof described herein can be used in any of various suitable combinations with one another. For example, any of the inserts (e.g., as shown in FIGS. 5A-B) described herein can be used in combination with any of the fluidic systems (e.g., well plates) described herein, and/or in combination with any of the perturbation sources (e.g., mechanical actuators, chemical perturbations, or toxicological perturbations) described herein. Further, any of the dimensions of such devices and components thereof can be modified to accommodate other components and devices.

In some embodiments, bioreactors and associate components, as described herein, can comprise materials that are transparent to X rays so that it is possible to image by microCT the construct within the bioreactor. Similarly, the bioreactor materials can be such that other imaging techniques, such as fluorescence microscopy, can be used "non-invasively," without removing the constructs from the bioreactor.

Example 1

To evaluate some of the devices, systems, methods, and techniques described herein, studies were conducted. Tissue engineering (TE) bone was formed by seeding human MSCs ($4-20\times10^6$/ml) in gelatin/hydroxyapatite hydrogels by photocrosslinking, and cultured in BMP-2 included osteogenic media. Cartilage was engineered by seeding MSCs ($4-60\times10^6$/ml) in gelatin/hyaluronic acid hydrogel by photocrosslinking, and treated with transforming growth factor-$\beta$ 3 (TGF-$\beta$3) included chondrogenic medium. Osteochondral interfaces were formed by placing layers of MSC-laden ($4-20\times10^6$/ml) gelatin hydrogels between the chondral and osseous-constructs. This 3-layer TE osteochondral tissue was then inserted into the mold shown in FIGS. 5C and 5D and cultured in a chamber as shown in FIG. 6 with 2 separated fluid streams for 6 weeks. The upper fluid stream 384 supplied chondrogenic medium (CM) and the lower fluid stream 386 supplied osteogenic medium (OM) at a flow rate of 1 µl/s. [CM: Dulbecco's Modified Eagle's Medium (DMEM) supplemented with 10 ng/ml recombinant human TGF-$\beta$3 (Peprotech), 1% Insulin-Transferrin-Selenium, 50 µM ascorbic acid 2-phosphate, 55 µM sodium pyruvate, 23 µM L-proline, and 1% antibiotics-antimycotic, OM: $\alpha$-MEM containing 10% fetal bovine serum, 1% antibiotics-antimycotic, 10 ng/ml recombinant human bone morphogenetic protein-2 (BMP-2; PeproTech), 1% L-alanyl-L-glutamine, 10 nM dexamethasone, 0.1 mM L-ascorbic acid 2-phosphate, and 10 mM $\beta$-glycerophosphatel.

Next, a native bone and endothelial cell construct was prepared. The microvascular endothelial cell (EC) line HMEC-1 was maintained in EGM-2MV media (Lonza). Human bone plugs were harvested from human trabecular bone using 5.0 mm diameter biopsy hole punches (Miltex) and cultured in DMEM/10% FBS/1% PS for two weeks. EC-containing collagen gels were prepared using the 3D Collagen Culture Kit (Millipore) according to the manufacturer's instructions. Briefly, ice-cold 0.4 ml collagen solution was mixed with 0.1 ml 5× M199 medium and 12.5 µl neutralization solution in 1.5 ml Eppendorf tubes. 25 µl of EC solution ($40\times10^6$ cells/ml DMEM) was added and mixed thoroughly. Bone plugs were then coated in EC/collagen gel by immersion in gel solution for 1 hour in a cell culture incubator. Native bone-EC constructs were cultured in 24-well plates containing 1 ml DMEM/10% FBS/1% PS per well for 0, 4, or 6 weeks.

Next, an osteoprotegerin enzyme-linked immunosorbent assay (ELISA) was performed. Native bone-EC constructs were washed in PBS and cultured in serum-free media for 4 days. Conditioned media samples were collected and analyzed by osteoprotegerin ELISAs (Abcam) exactly according to the manufacturer's instructions.

Next, histology and immunohistochemistry (IHC) was performed. TE bone-cartilage constructs and native bone-EC constructs were washed in PBS and fixed in 4% paraformaldehyde (Electron Microscopy Sciences) overnight at 4° C. Native bone-EC constructs were decalcified overnight in DECAL® (Decal Chemical Corporation) at 4° C. To prepare samples for paraffin embedding, constructs were dehydrated by graded ethanol washes (30%, 50%, 70%, 95%, 100%), each overnight at 4° C., cleared in xylene for 1 hour at room temperature, and infiltrated with paraffin wax in 1:1 paraffin:xylene mix for 10 minutes at 60° C. Samples were incubated in 60° C. paraffin overnight to remove residual xylene, embedded, and sectioned (7 µm thickness).

For hematoxylin and eosin staining, samples were washed twice in Histo-Clear II (Electron Microscopy Sciences), rehydrated in graded ethanols (100%, 95%, 70%, 50%) for 1 min each, washed in deionized water for 1 min, stained in Gill No. 2 hematoxylin (Sigma-Aldrich) for 20 min, washed in running tap water for 1 min, immersed in acid alcohol (0.25% HCl in 70% ethanol) and then Scott's tap water substitute (10 g MgSO4, 0.75 g NaHCO$_3$, 1 L ddH2O) for 30 seconds each, washed in running tap water for 2 min, and stained in alcoholic eosin Y 515 (Leica) for 1 min. The samples were then dehydrated in graded ethanols (95%, 100%) for 1 min each, washed twice with Histo-Clear II for 1 min each, mounted with Clarion Mounting Media (Biomeda), and coverslipped.

For IHC, samples were rehydrated via gradient ethanol washes (100%, 95%, 70%, 50%) for 1 min each and washed in running tap water for 5 min. Following antigen retrieval via citrate buffer, pH 6.0 (eBioscience) for 40 min at 90° C., endogenous peroxidase activity was blocked with 3% H$_2$O$_2$ in methanol for 10 min at room temperature. Samples were then incubated with 1% horse serum for 45 min at room temperature and primary antibody (osteoprotegerin (Abcam), osteocalcin (Abcam)) diluted 1:200 with 1% horse serum overnight at 4° C. in humidified chambers. Following washes with PBS, samples were incubated with biotinylated secondary antibody (Vector Labs) for 30 min at RT, washed with PBS, incubated with HRP-conjugated streptavidin (Vector Labs) for 30 min at RT, washed with PBS, incubated with VECTOR® NOVARED™ peroxidase substrate for 1 min, washed with tap water, counterstained with hematoxylin OS (modified Mayer's formula) (Vector) for 3 seconds, washed in running tap water for 5 min, dehydrated in graded ethanols (95%, 100%) for 5 min each, washed twice in Histo-Clear II for 5 min each, mounted with Clarion Mounting Medium, and coverslipped. Histology and IHC images were captured with an Olympus CKX41 microscope outfitted with a Leica DFC 3200 camera.

FIGS. 12A-B show exemplary resulting osteochondral microtissue constructs, under 10× and 20× magnification, respectively (the bar in the lower corner of each of FIGS. 12A and 12B represents 100 µm). FIGS. 12A-B show, in particular, an interface between an osteoblast construct (labeled oc) and a mesenchymal construct (labeled mc), grown in accordance with the techniques described herein, after six weeks of culture. The arrows indicate a dense structure between the two layers.

To evaluate the effects of crosstalk between endothelial cells and bone cells in the disclosed systems, studies were conducted in which native bone plugs were cultured with collagen gels seeded with or without endothelial cells and cultured for four weeks. The results indicate that samples of bone coated with collagen gels containing endothelial cells produce more new bone matrix and osteoprotegerin, indicating activation of anabolic bone pathways. Specifically, FIGS. 13A-B show bone growth in control tests in the absence of endothelial cells, at 10× and 20× magnification, respectively. This can be compared to the results shown in FIGS. 14A-B, which show bone growth in the presence of endothelial cells, at 10× and 20× magnification, respectfully.

Figure 15:
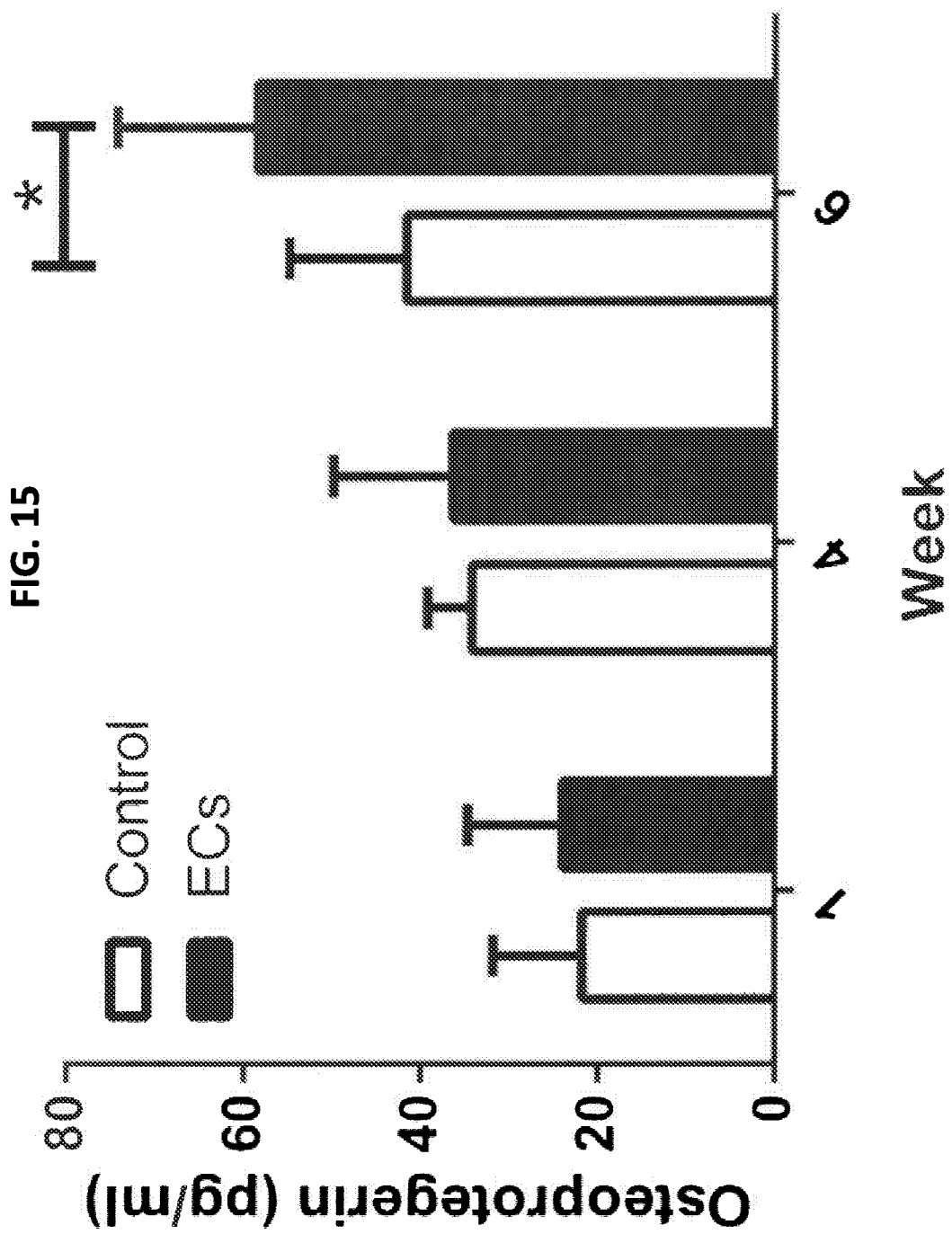
FIG. 15 shows a chart illustrating the behavior of tissues in the presence and in the absence of endothelial cells, at 1 week, 4 weeks, and 6 weeks of growth.

As can be seen, bone growth was greater in the tests in which endothelial cells were present. Future work will assess the extent to which crosstalk with endothelial cells mitigates the negative effects of injurious mechanical and chemical stresses on bone behavior (e.g., by promoting growth, as established by the results shown in FIGS. 13-14). In each of FIGS. 13A, 13B, 14A, and 14B, tissues were IHC-stained for osteoprotegerin, the bar in the lower right corner represents 100 μm, B indicates a bone plug, and G indicates a collagen gel. FIG. 15 shows an ELISA analysis of media samples conditioned by bone plugs coated in collagen gel with and without endothelial cells for 1, 4, and 6 weeks. The asterisk indicates that p=0.0362.

Example 2

The disclosed reactors can achieve cellular communication between the different tissues in the two compartments of the reactor, and each signals to the other in response to changes in the local environment. In a specific example, when bone is stimulated by hormones simulating the menstrual cycle, the hormones initiate an anabolic response and signal to cartilage that will respond even without direct exposure to the hormones. The ability to study this phenomenon is particularly important because hormonal exposure has a protective effect against bone volume loss. To evaluate this effect, a first experiment used a native osteochondral plug.

Figure 16:
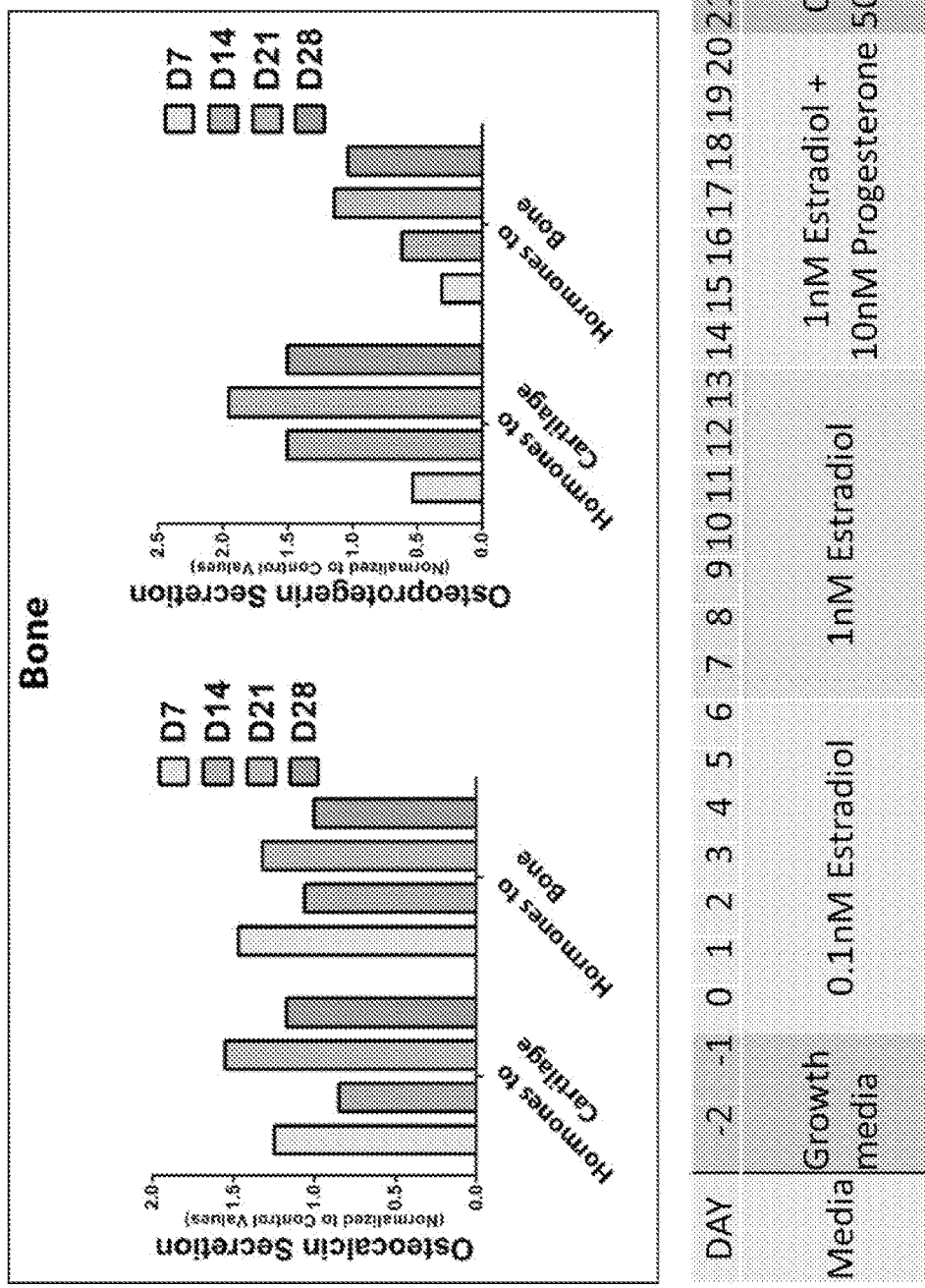
FIG. 16 is a graph showing ELISA data demonstrating use of the bioreactor for evaluating response of cartilage and bone to exposure to hormones. Osteocalcin and osteoprogerin secretion from bone and cartilage is shown at day 7 (D7), day 14 (D14), day 21 (D21), and day 28 (D28).

For the osteochondral plug experiment, human osteochondral plugs from the knees of women undergoing total knee replacement were explanted from macroscopically asymptomatic regions of the joint. Three treatment groups were evaluated with different fluid flow between the top (cartilage) and lower (bone) chambers of the bioreactor. The fluid flows to the top and bottom chambers included Dulbecco's Modified Eagle Media (DMEM), Fetal Bovine serum (FBS), and Penicillin/Streptomycin/Amphotericin (PSF), optionally with hormones that simulate the menstrual cycle. The treatment groups were as follows:
Treatment Groups:
1. Top: DMEM+FBS+PSF
   Bottom: DMEM+FBS+PSF
2. Top: DMEM+FBS+PSF+hormones simulating the menstrual cycle
   Bottom: DMEM+FBS+PSF
3. Top: DMEM+FBS+PSF
   Bottom: DMEM+FBS+PSF+hormones simulating the menstrual cycle
For the groups in which hormones were supplied, the media was altered over the time course shown in FIG. 16. The results shown in FIG. 16 show that hormones affected both bone and cartilage. In particular, hormone treatment reduced osteocalcin secretion and enhanced osteoprotegerin secretion. The results also provided evidence of a cyclic bone response to changing concentrations of hormones that mimicked changes that would be seen throughout the menstrual cycle of a woman. The hormones prevented loss of calcification in the osteochondral junction.

Example 3

Figure 17:
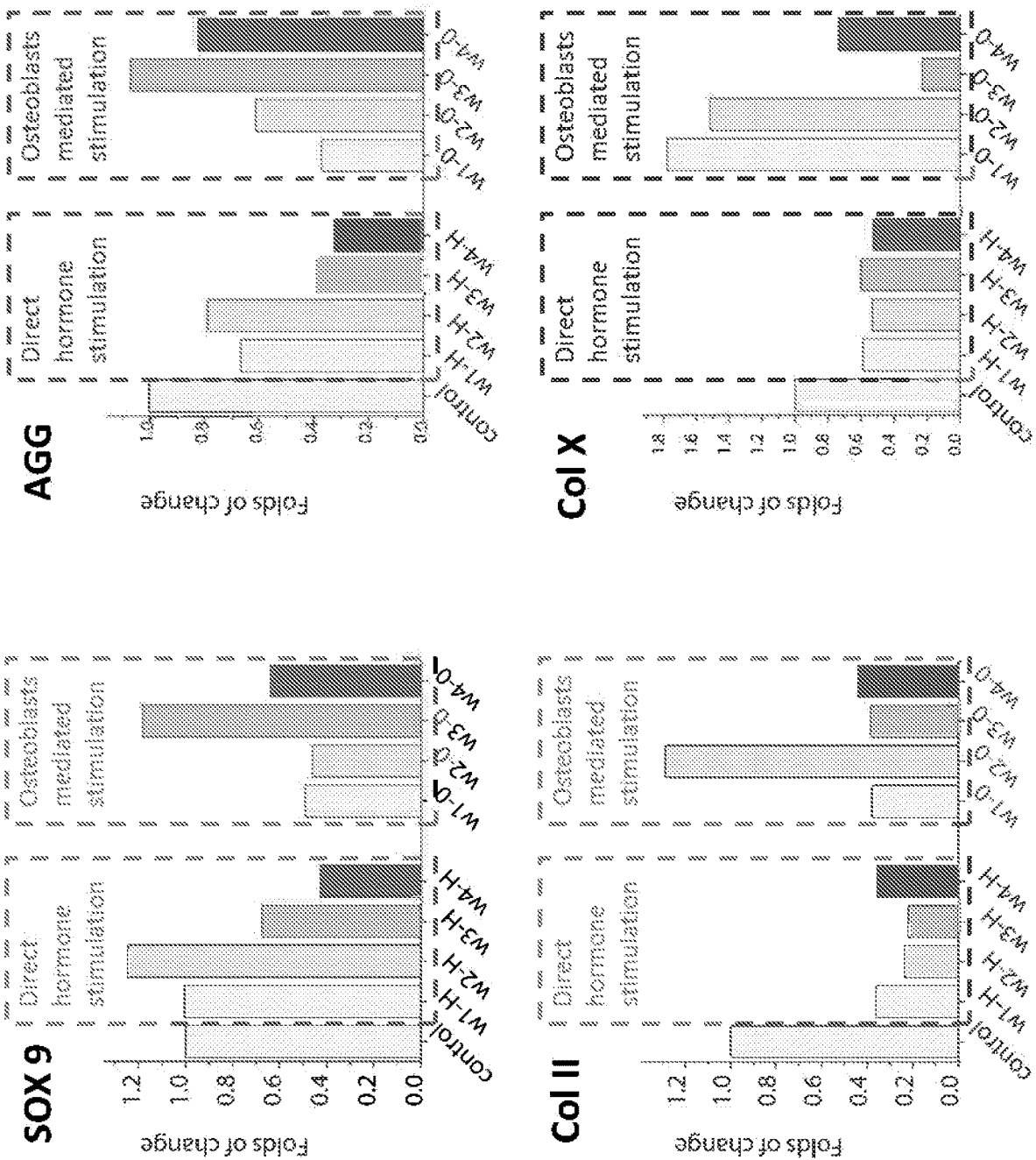
FIGS. 17-20 are graphs that show differential expression of markers (as determined by RT-PCR) for a control medium that contained no estrogen or progesterone (first bar), and then different concentrations of hormones supplied to one or the other of the bioreactor chambers during week 1 (w1: 0.1 nM estradiol), week 2 (w2: 1 nM estradiol), week 3 (w3: 1 nM estradiol and 10 nM progesterone), and week 4 (w4: 0.1 nM estradiol and 50 nM progesterone).
Figure 18:
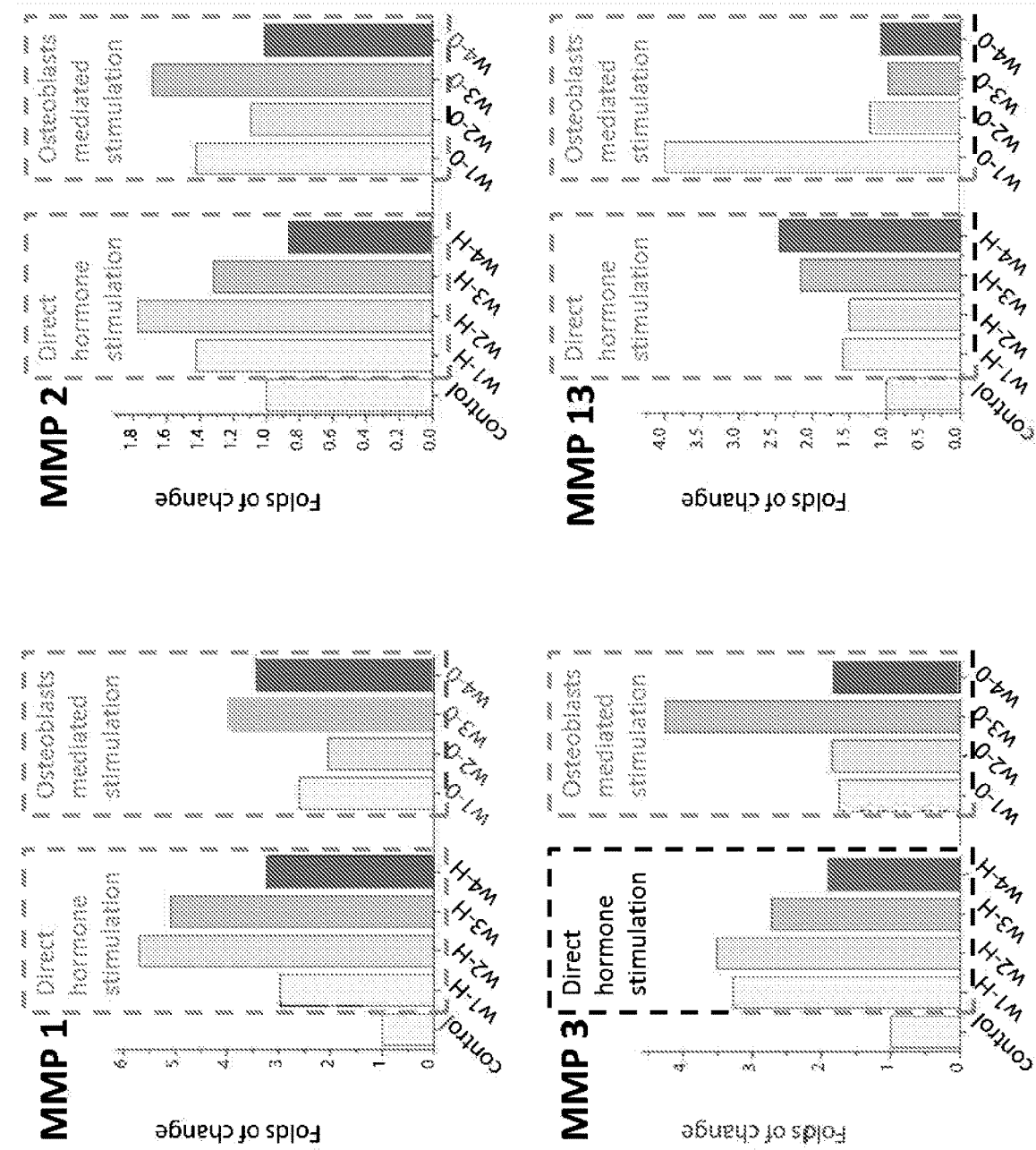

In another demonstration of the use of the bioreactor, a chondrocyte response was shown using real time PCT (RT-PCR) to illustrate that stimulation of bone tissue in the lower chamber of the bioreactor stimulated a chondrocyte response in the upper chamber. FIGS. 17-18 show differential expression of markers (as determined by RT-PCR) for a control medium that contained no estrogen or progesterone (first bar), and then different concentrations of hormones supplied to the chambers during week 1 (w1: 0.1 nM estradiol), week 2 (w2: 1 nM estradiol), week 3 (w3: 1 nM estradiol and 10 nM progesterone), and week 4 (w4: 0.1 nM estradiol and 50 nM progesterone). "Direct hormone stimulation" indicates that the hormones were supplied to the cartilage (top) chamber of the bioreactor; "osteoblasts mediated stimulation" indicates that the hormones were supplied to the bone (bottom) chamber of the bioreactor and had an indirect effect on the chondrocytes in the cartilage chamber.

Figure 19:
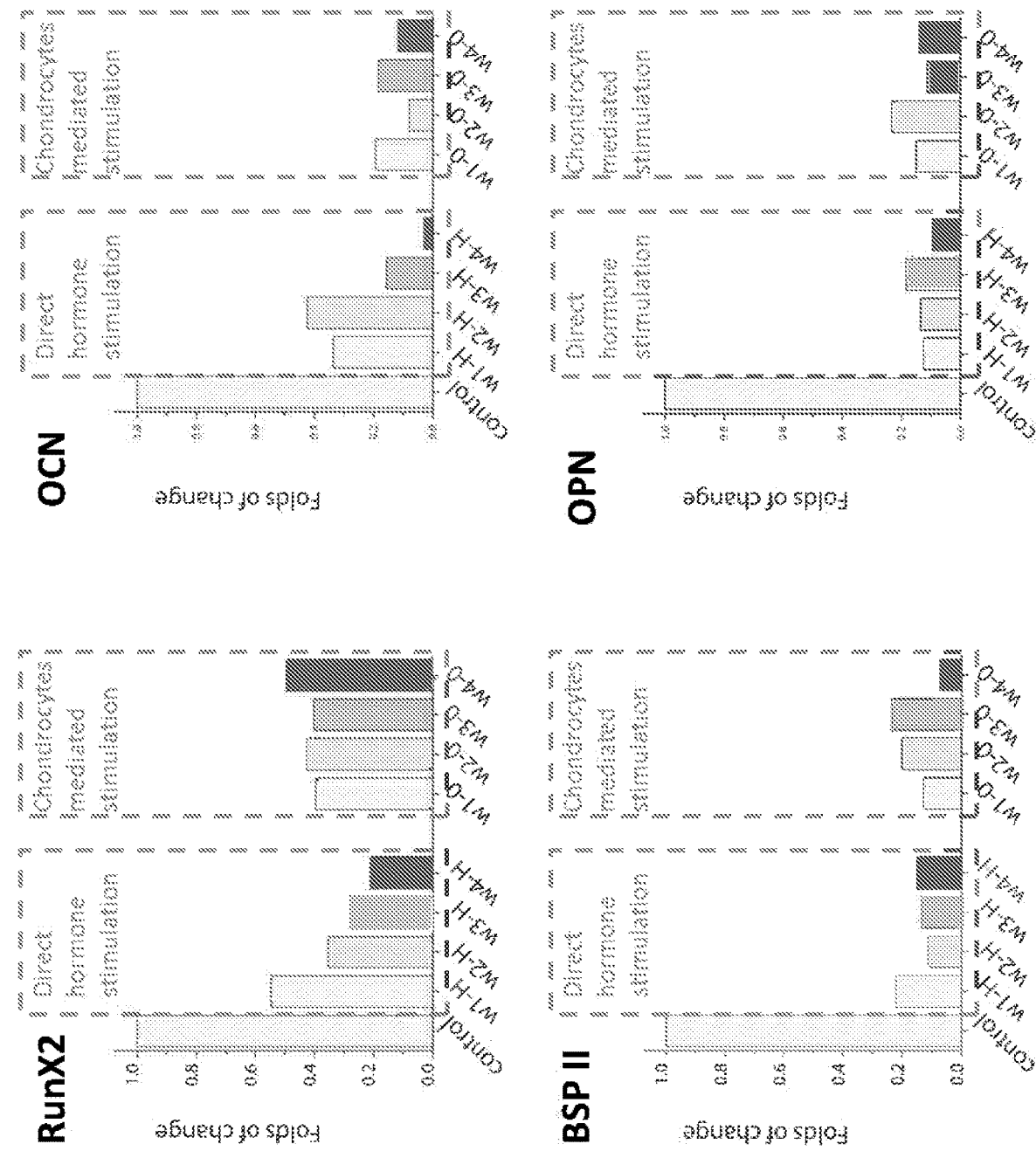
Figure 20:
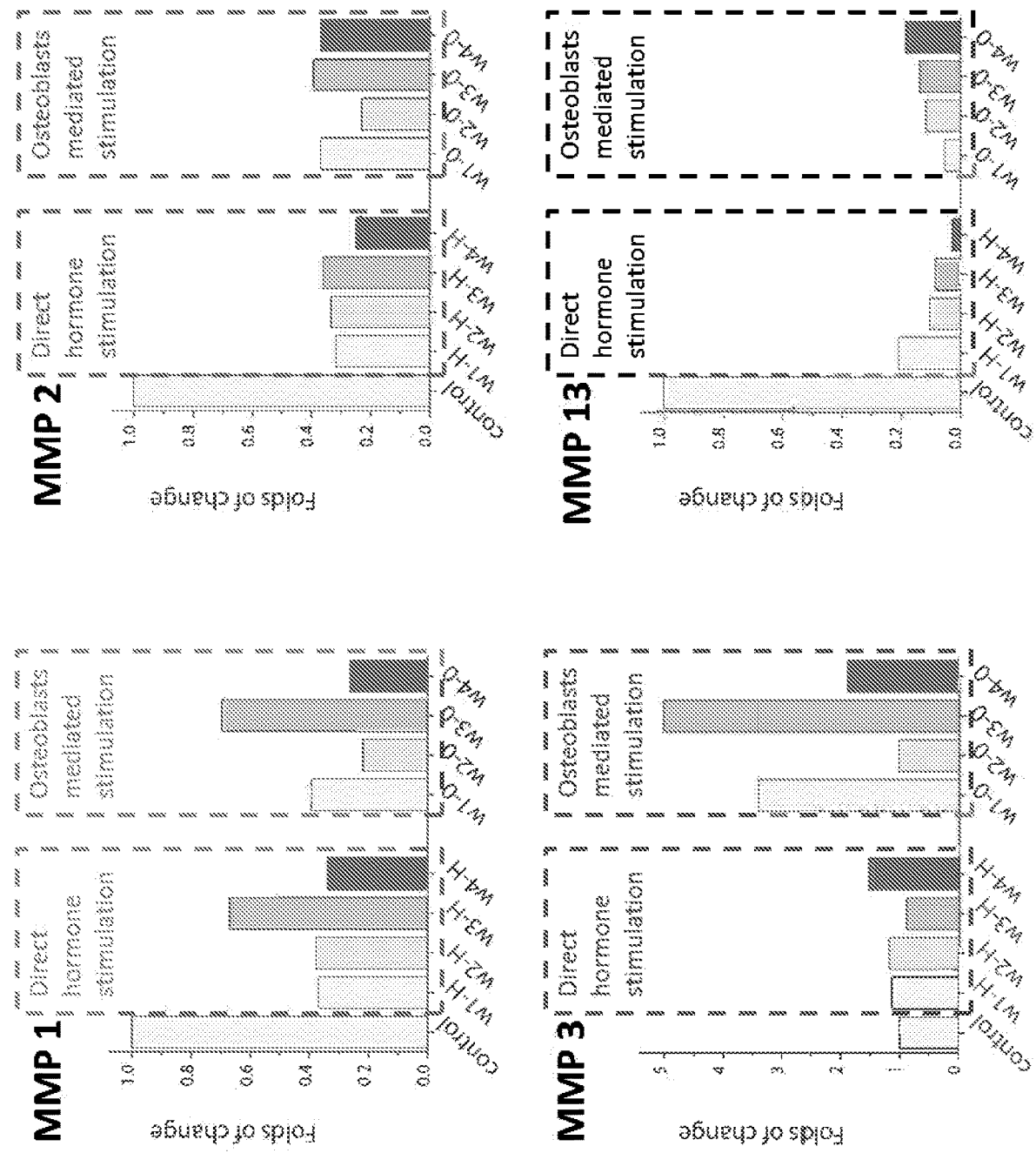
Figure 21A:
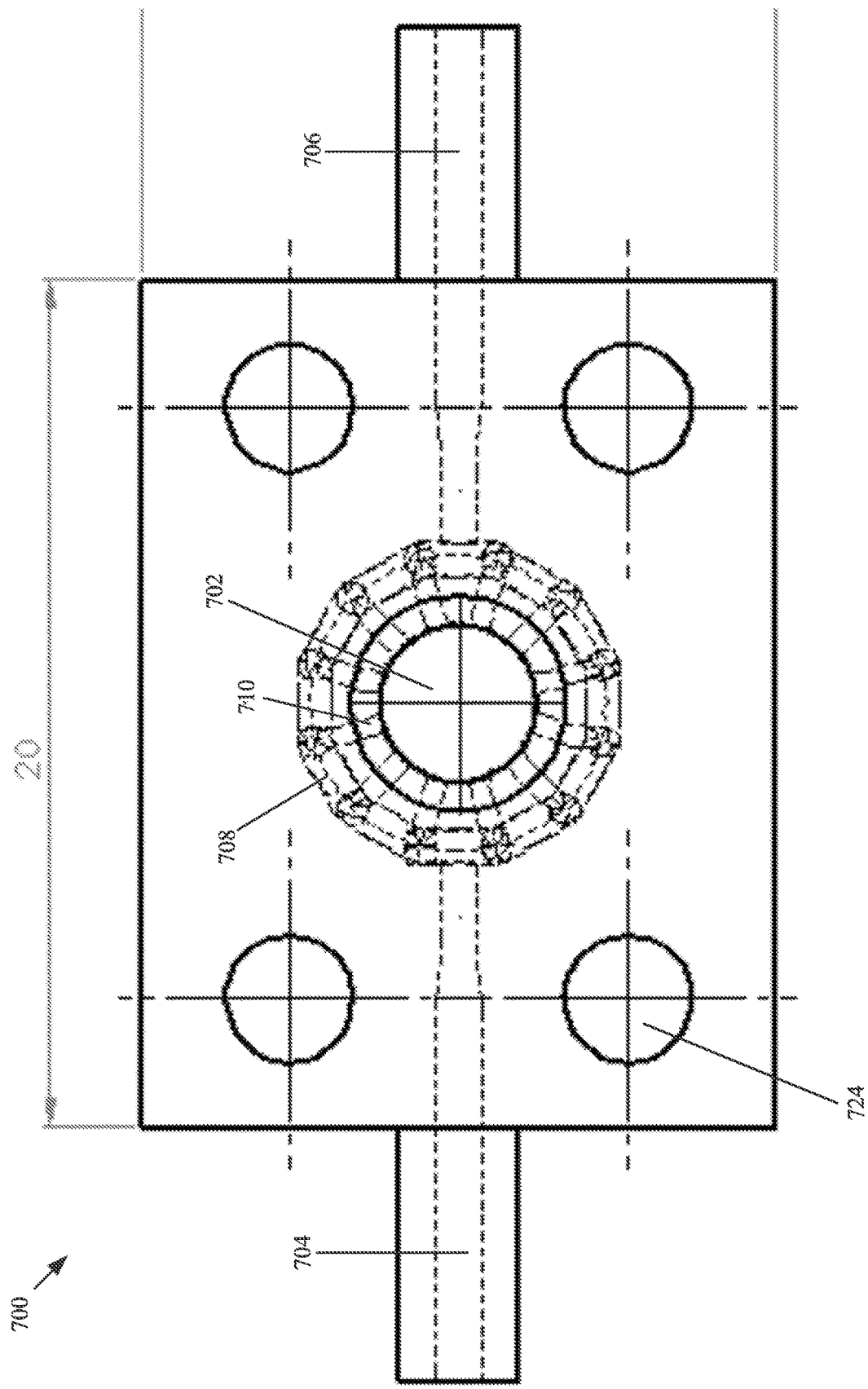
FIG. 21A is a cross-sectional side view of an exemplary diffusion based single well bioreactor.
Figure 21B:
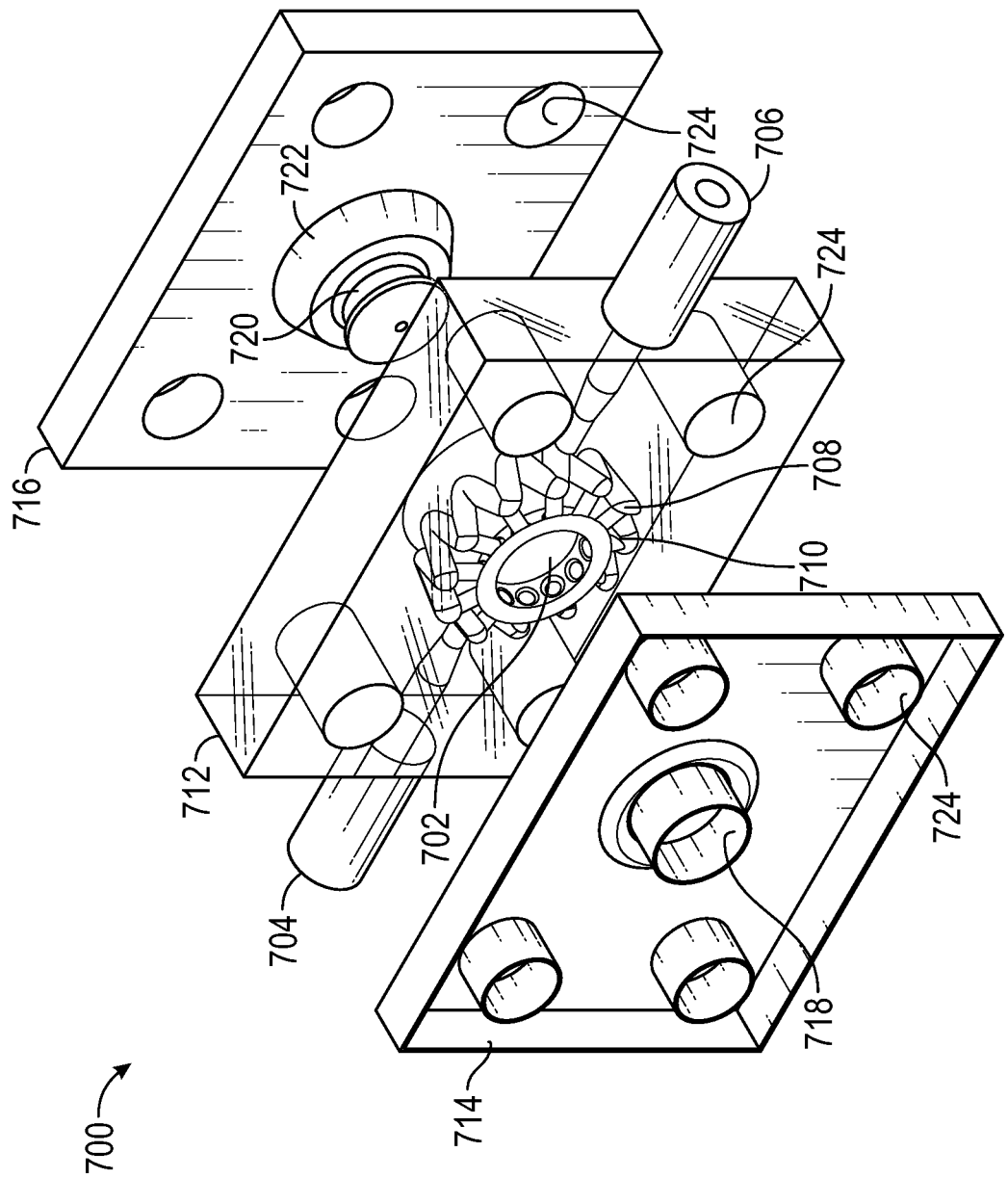
FIG. 21B is an exploded isometric view of the bioreactor of FIG. 21A.
Figure 21C:
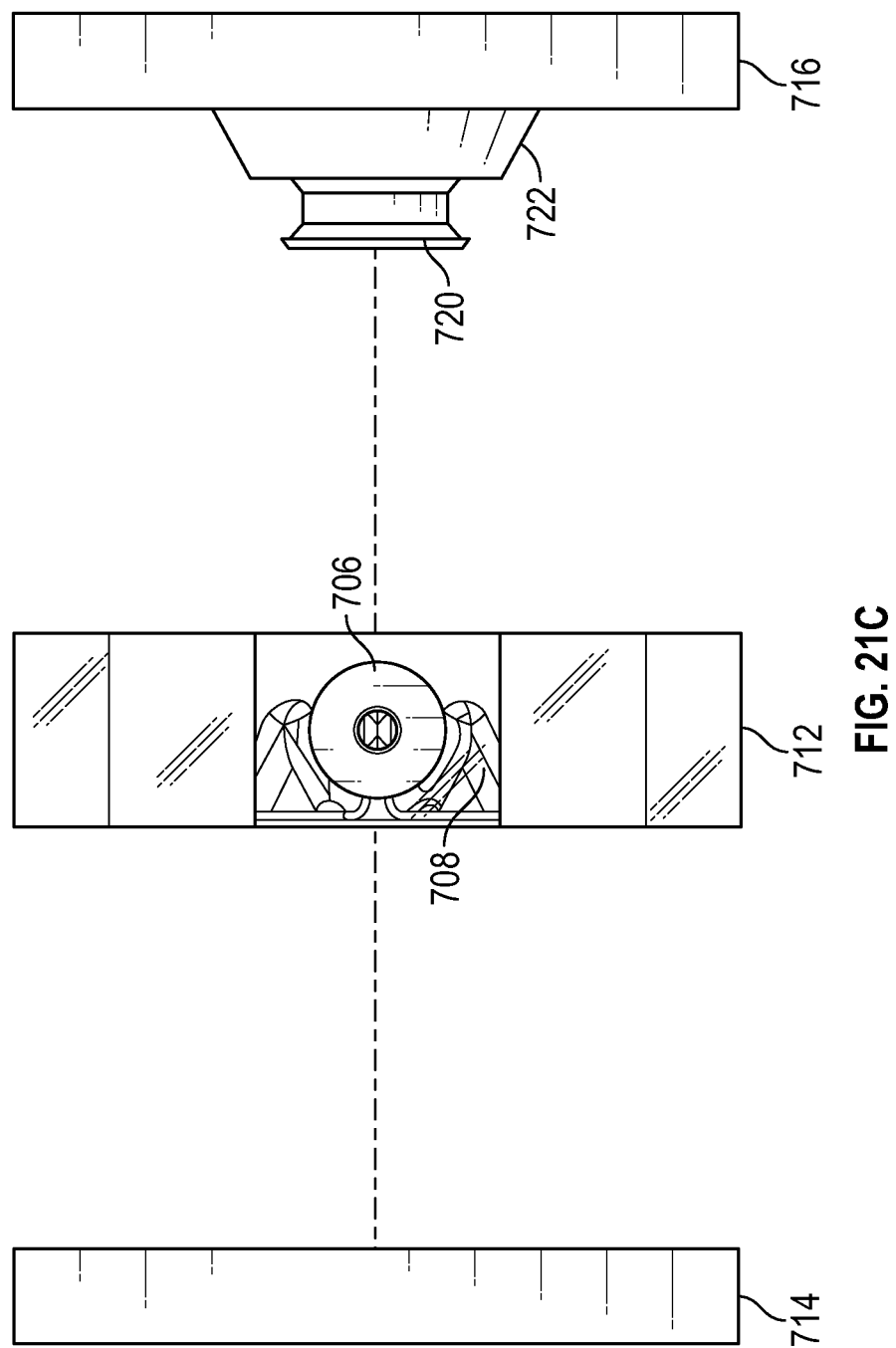
FIG. 21C is an exploded side view of the bioreactor of FIG. 21A.
Figure 21D:
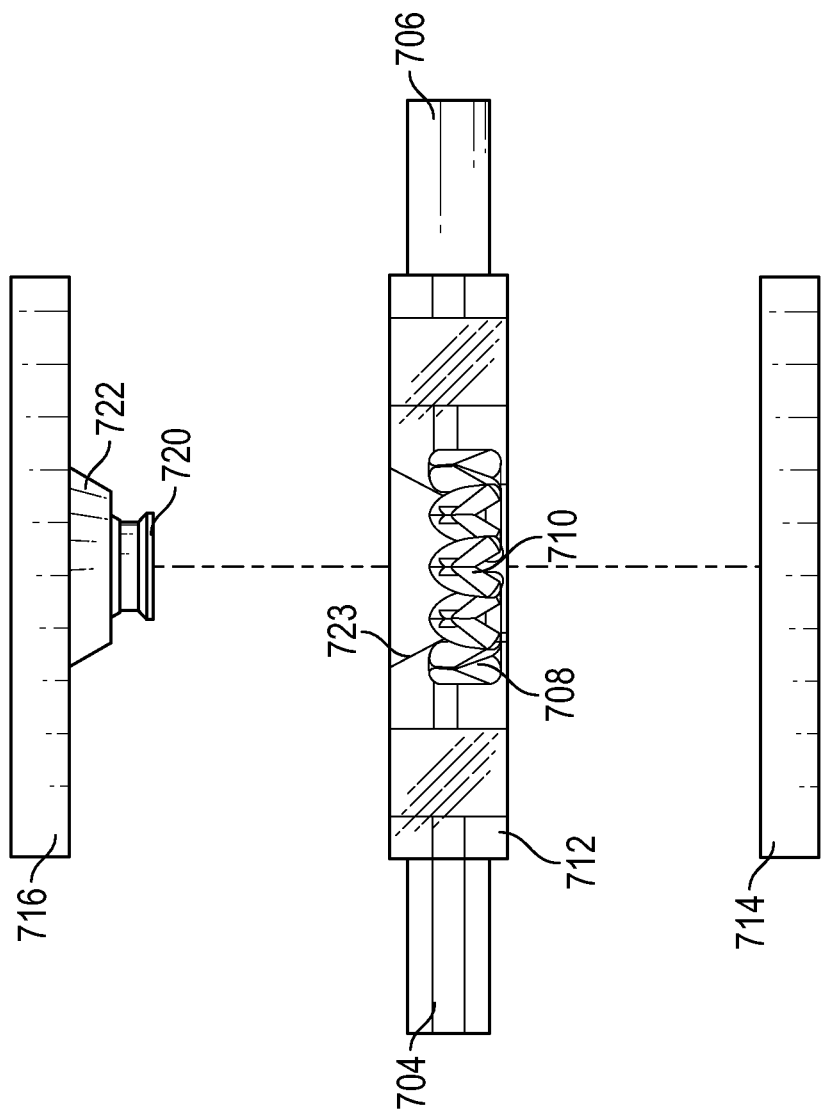
FIG. 21D is an exploded end view of the bioreactor of FIG. 21A.
Figure 22A:
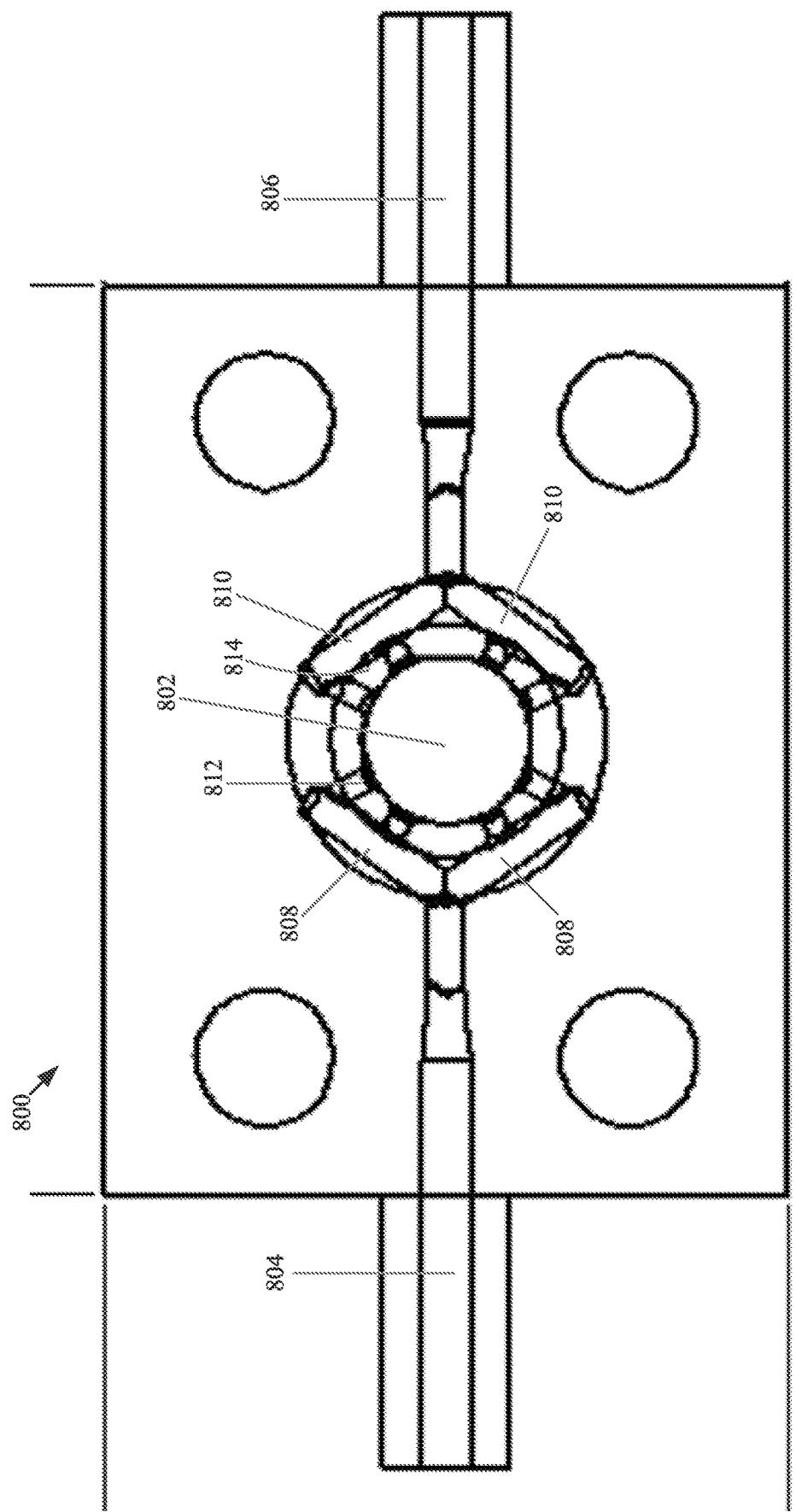
FIG. 22A is a cross-sectional side view of an exemplary perfusion based single well bioreactor.
Figure 22B:
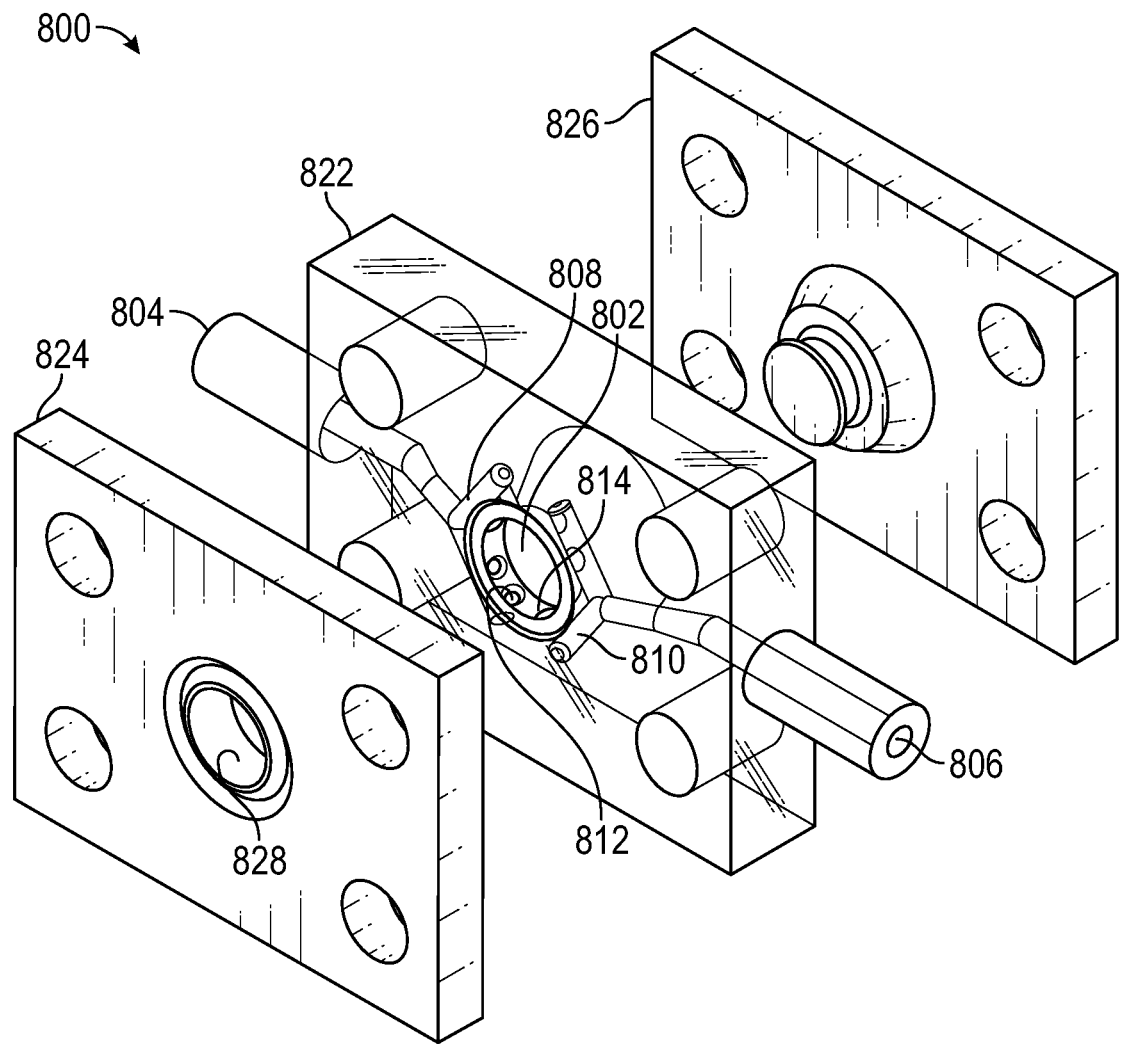
FIG. 22B is an exploded isometric view of the bioreactor of FIG. 22A.
Figure 22C:
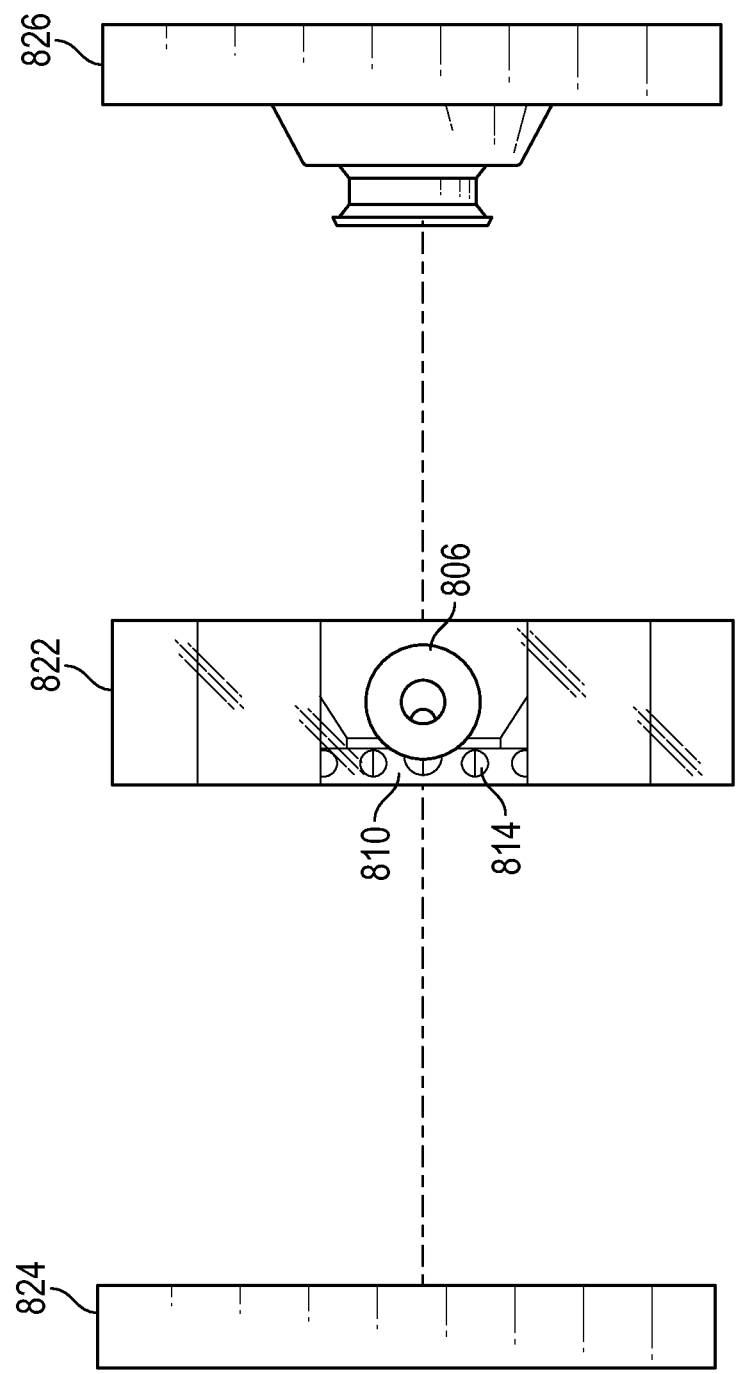
FIG. 22C is an exploded side view of the bioreactor of FIG. 22A.
Figure 22D:
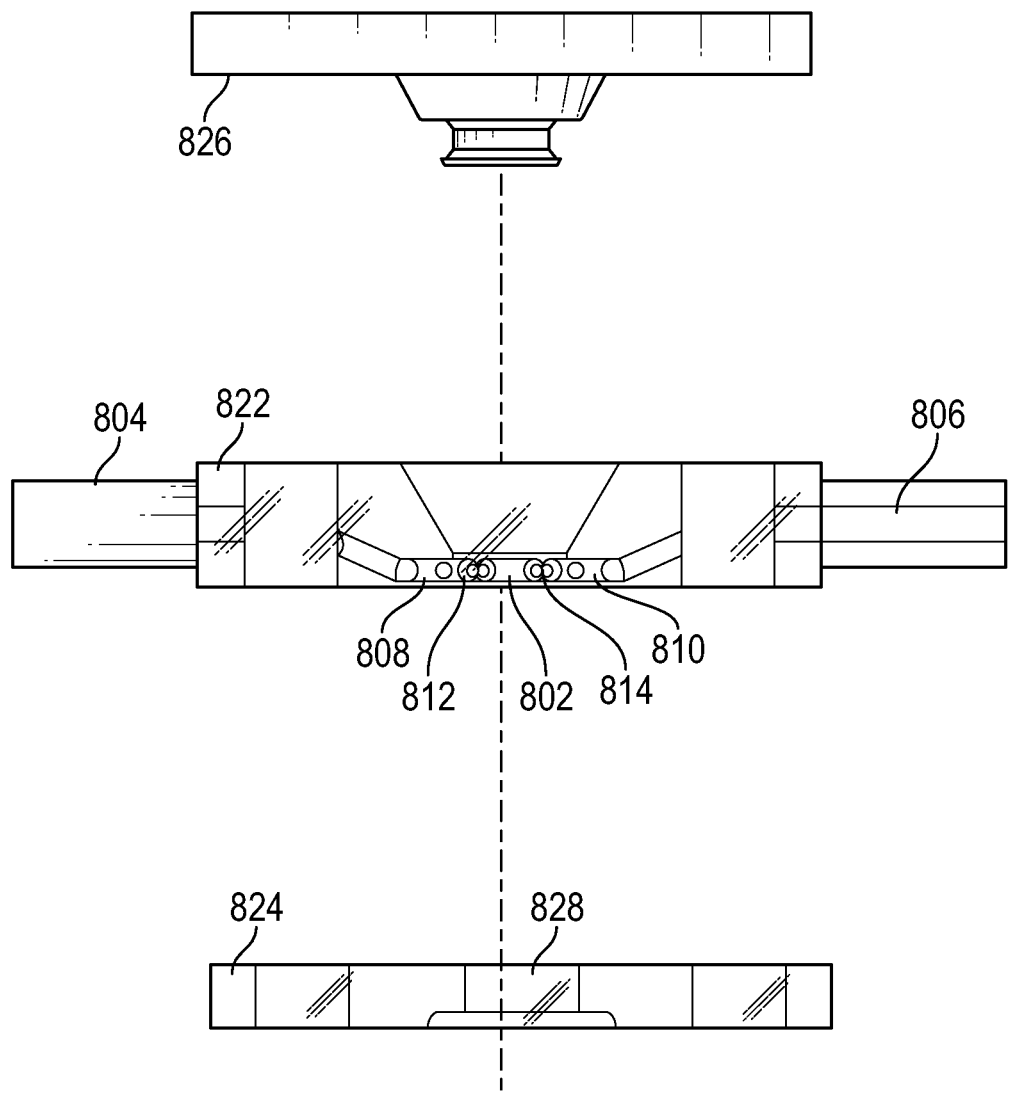
FIG. 22D is an exploded end view of the bioreactor of FIG. 22A.
Figure 23A:
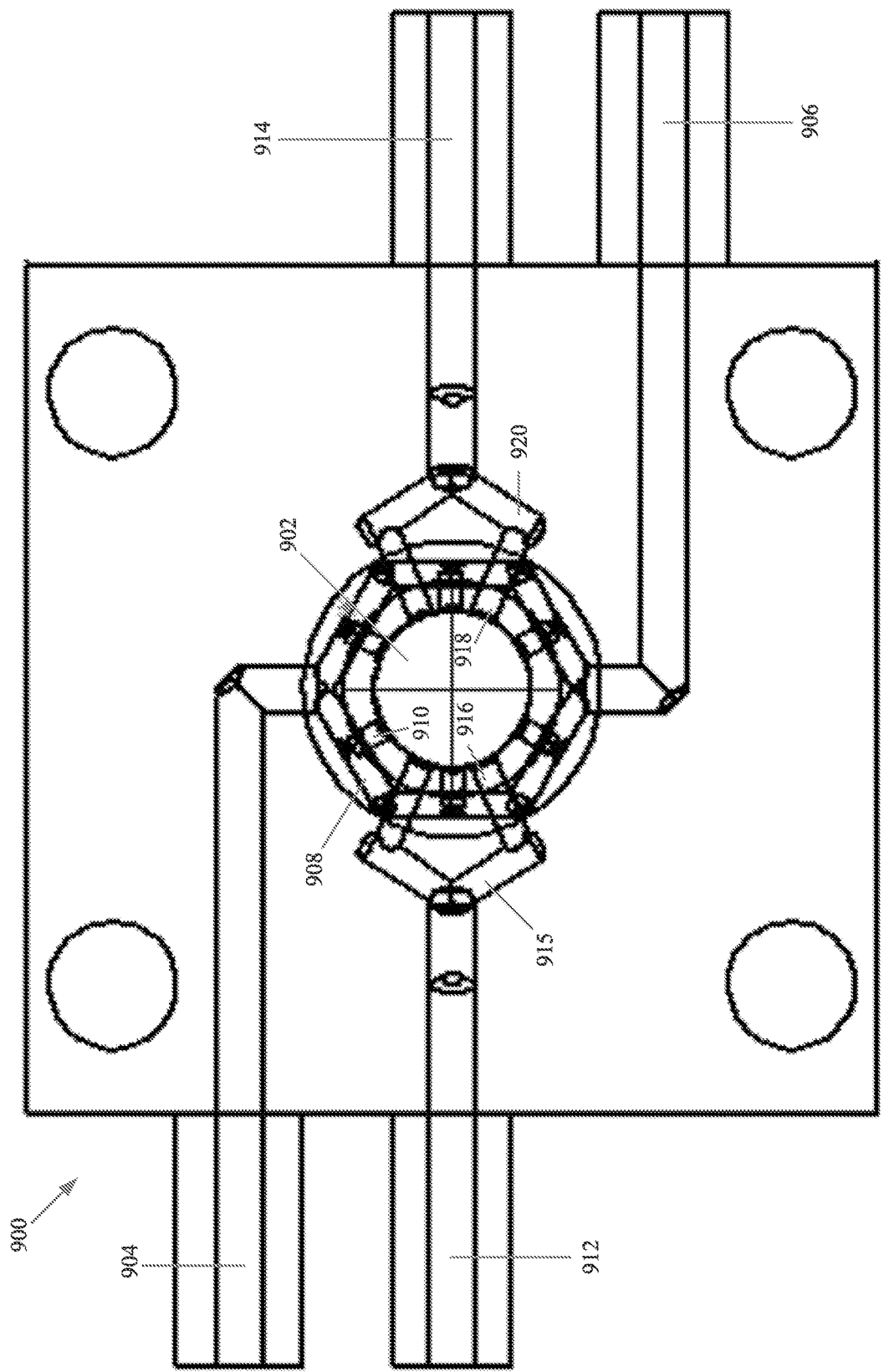
FIG. 23A is a cross-sectional side view of an exemplary combined diffusion and perfusion based single-well bioreactor.
Figure 23B:
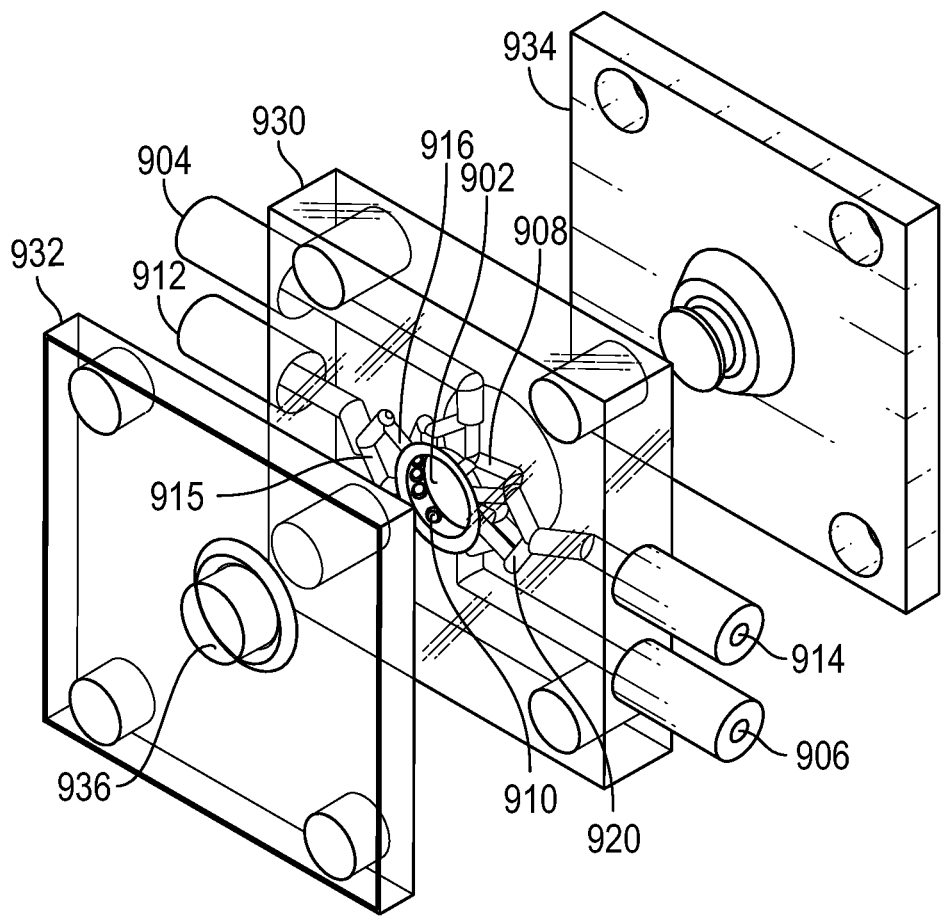
FIG. 23B is an exploded isometric view of the bioreactor of FIG. 23A.
Figure 23C:
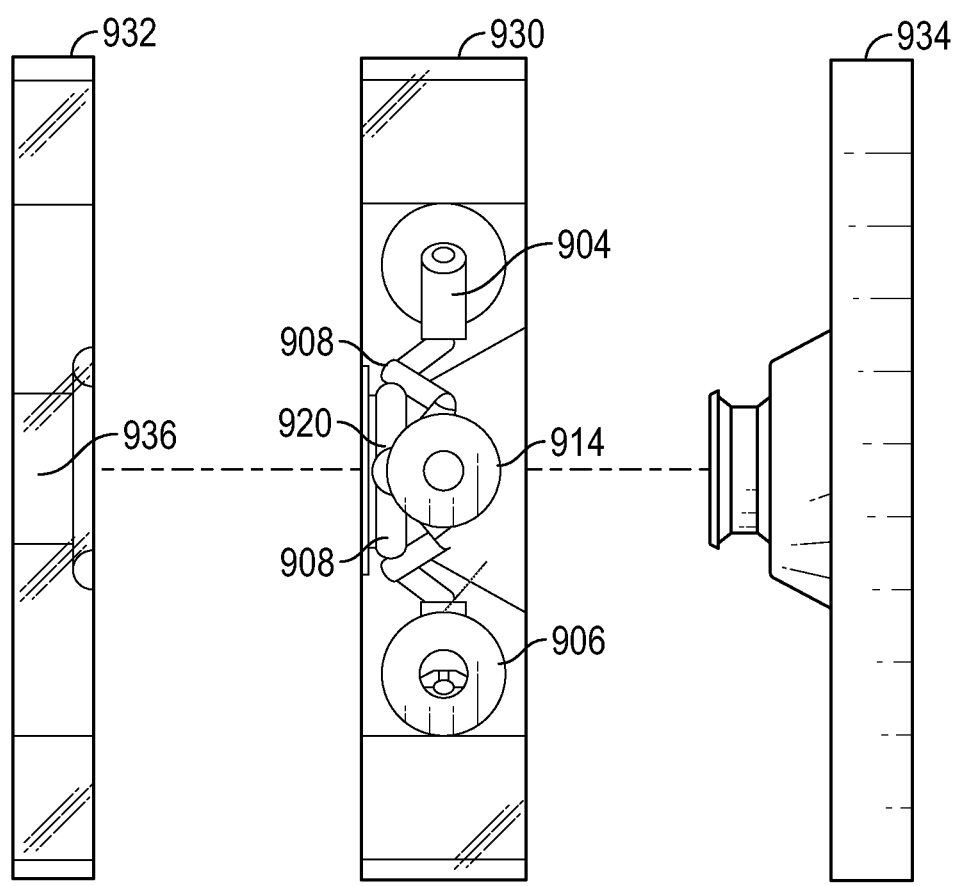
FIG. 23C is an exploded side view of the bioreactor of FIG. 23A.
Figure 23D:
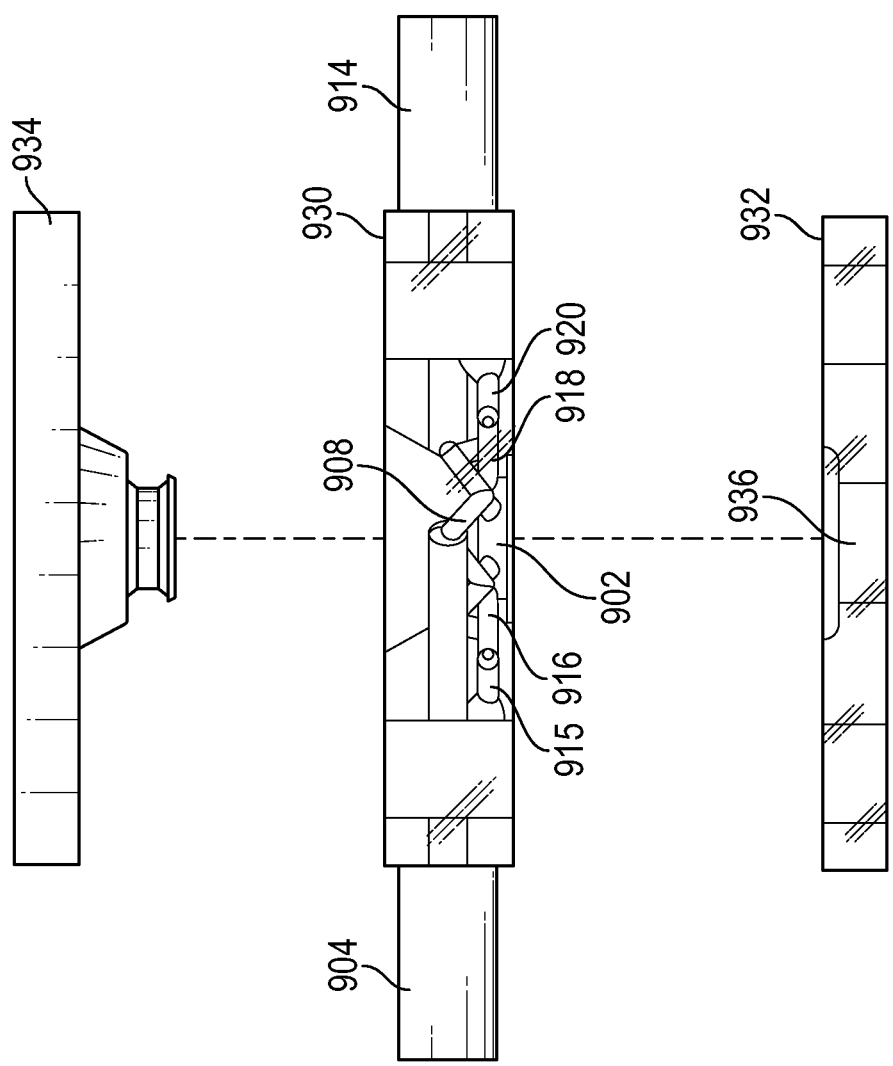
FIG. 23D is an exploded end view of the bioreactor of FIG. 23A.

FIGS. 19-20 show differential expression of markers (as determined by RT-PCR) for a control medium that contained no estrogen or progesterone (first bar), and then different concentrations of hormones supplied to the cartilage chamber during week 1 (w1: 0.1 nM estradiol), week 2 (w2: 1 nM estradiol), week 3 (w3: 1 nM estradiol and 10 nM progesterone), and week 4 (w4: 0.1 nM estradiol and 50 nM progesterone). "Direct hormone stimulation" indicates that the hormones were supplied to the bone (bottom) chamber of the bioreactor; "chondrocytes mediated stimulation" indicates that the hormones were supplied to the cartilage (top) chamber of the bioreactor and had an indirect effect on the osteoblasts in the bone chamber.

Higher concentrations of estradiol in the bone chamber of the bioreactor (FIGS. 17-18, weeks 1 and 2) downregulated cartilage anabolic markers such as Sox9 and Aggrecan, but downregulation is more pronounced when estradiol is applied to the osseous side. When progesterone is progressively added (week 3 and 4), downregulation is still present but with an opposite trend (higher when hormones are directly applied to cartilage). Bone anabolic markers are generally downregulated in all conditions. Cartilage hypertrophy marker ColX is upregulated only when estradiol is administered to the osseous side, and downregulated in any other conditions, suggesting a concomitant signaling from osteoblasts. Metalloproteinases are generally upregulated in cartilage for all conditions (except MMP-13 which has a more complex behavior).

As shown in FIGS. 19-20, metalloproteinases are generally downregulated in bone for all conditions (except MMP-3 which has a more complex behavior). Bone anabolic markers are generally downregulated in all conditions.
Devices and Systems for Optical Monitoring of Bioreactor Wells It can be desirable to have optical access to cells organized in 3D constructs, such as to monitor their morphology over time in response to different stimuli (e.g., differentiation, stress, pharmacological treatment, etc.). Both native cells and fluorescent cells can be optically monitored using disclosed bioreactor systems. It can also be desirable to be able to include in a bioreactor cells transfected with reporter genes to visually monitor activation of fluorescence in response to stimuli. Furthermore, it can be desirable to minimize the amount of cells needed to be present in a bioreactor for producing a 3D construct that can mimic single or multiple tissues systems. Still further, it can be desirable to product multiple different 3D construct types (e.g., hydrogels, micromasses, polymeric scaffolds, etc.) in a single bioreactor well.

FIGS. 21-27 illustrate exemplary bioreactor devices and systems that comprise one or more microwells coupled to microfluidic inlet and outlet channels. In some embodiments, each well in in the bioreactor system can include planar dimensions smaller than those of single wells in conventional 96 well plates. The height of each well can be selected to contain a small volume, such as about 10 µl or less. The height and the radius (for circular wells) or length and width (for rectangular wells) can be adjusted during fabrication depending on the dimensions of the tissue construct intended to be contained therein and the medium volume needed to maintain it. Larger and smaller volumes can be achieved, reaching as little as 1 µl of volume, or less, in some embodiments. In some embodiments, for example, the radius for a circular well can be about 1.8 mm and the height can be about 0.96 mm resulting in a total well volume of about 10 µl. Each microwell can be sealed by a removable base and a removable lid, and one or body can include O-rings for sealing. The thickness of the base can be used to delimit the effective inner volume of the microwell. A small circular glass cover slip can be placed between each microwell and the lid to allow improved optical access to the microwell. In some embodiments, the lid, microfluidic microwell chamber, and base are held together by screws for ease of use and re-use. In other embodiments, the various parts can held together with clip-in or snap-fit connections for rapid assembly and disassembly.

As shown in FIGS. 21-27, the microfluidic systems have one or more inlets and one or more outlets coupled to each well. In the single well system, as shown in FIGS. 21-25, each inlet is connected to a medium source (e.g., a syringe in a syringe pump setup) and each outlet is coupled to a collection container. The transport of fluid and molecules through the microfluidic chamber containing the cells/3D cell constructs can be (a) diffusion based, (b) perfusion based, or (c) a combination of diffusion and perfusion based.

FIGS. 21A-21D show a single well diffusion-based system 700, which includes well 702, inlet 704, outlet 706, a ring conduit 708 coupled to both the inlet and the outlet, and a plurality of radially extending channels 710 extending inwardly from the ring conduit 708 to the well 702. The fluids from the inlet 704 can reach the outlet 706 via the ring 708 without being forced through the cellular construct in the well 702. The radially aligned channels 710 allow the fluids to reach the construct and diffuse through it from several different directions at the same time.

The system 700 includes a main body 712, a lid 714, and a base 716, which can be attached together via aligned bolt holes 724, for example. The lid includes a viewing aperture 718 that is positioned over the well 702 with a transparent material, such as glass cover slip, blocking the aperture 718 and sealing the top of the well. The base 716 can include a lower wall 720 that forms the bottom of the well 702 and a shaped surface 722 that mates with a similarly shaped surface 723 (FIG. 21D) below the well in the main body 712. Gaskets, such as O-rings, can be included to seal the top and bottom of the well.

FIGS. 22A-22D show a perfusion based single well system 800 in which the fluid media can reach the outlet 806 from the inlet 804 only after being forced to perfuse through the well 802 and its content. The system 800 can also comprise inlet branch conduits 808 coupled to a plurality of radial feeder channels 812 and outlet branch conduits 810 coupled to a plurality of radial exit channels 814. The fluid flows through the inlet 804, through branches 808, through feeder channels 812 and into the well 802. Fluid then flows out of the well through exit channels 814, through branches 810, and out through outlet 806.

The system 800 can also include a main body 822, a lid 824, and a base 826, which can be attached together via aligned bolt holes, for example. The lid 824 includes a viewing aperture 828 that is positioned over the well 802 with a transparent material, such as glass cover slip, blocking the aperture 828 and sealing the top of the well. The base 826 can be similar to the base 716. Gaskets, such as O-rings, can be included to seal the top and bottom of the well.

FIGS. 23A-23D show a single well system 900, which combines both diffusion and perfusion in a single well. The well 902 is coupled to inlet 904, ring conduit 908, radial channels 910, and outlet 906 for fluid diffusion through the construct in the well. At the same time, the well 902 is coupled to inlet 912, branches 915, feeder channels 916, exit channels 918, branches 920, and outlet 914 for fluid perfusion through the construct in the well. The same or two different fluids can be supplied through the diffusion conduits and through the perfusion conduits. The ring conduit 908 and/or other conduits can have a non-planar path such that is can go under or over other conduits, such as channels 916 and 918, without intersecting.

The system 900 can also include a main body 930, a lid 932, and a base 934, which can be attached together via aligned bolt holes, for example. The lid 932 includes a viewing aperture 936 that is positioned over the well 902 with a transparent material, such as glass cover slip, blocking the aperture and sealing the top of the well. The base 934 can be similar to the base 716. Gaskets, such as O-rings, can be included to seal the top and bottom of the well.

The system 900 include two separate fluid media streams into and out of the well 902. In other embodiments, any number of separate fluid streams can be fed to a single well, in any combination of diffusion and perfusion arrangements. In some embodiments of this technology, the two or more fluid streams can be directed to two different cell types or two different portions of the construct in the well, thereby providing for a biphasic system. Such a biphasic system can comprise two or more different cell types in adjacent volumes, or a single cell type within a construct that is then locally differentiated by different signals in each media stream.

Figure 24A:
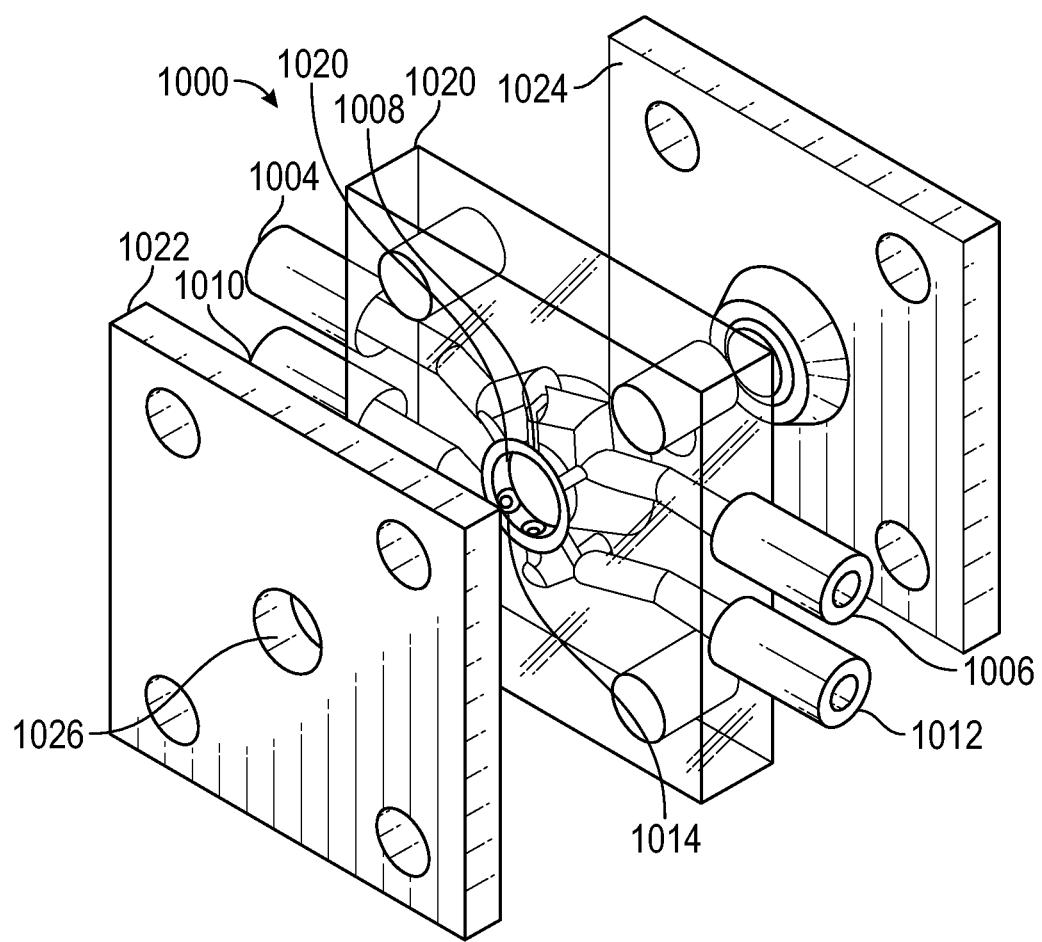
FIG. 24A is an exploded isometric view of an exemplary diffusion based circular bioreactor with two fluid inlets and two fluid outlets for a biphasic construct system.
Figure 24C:
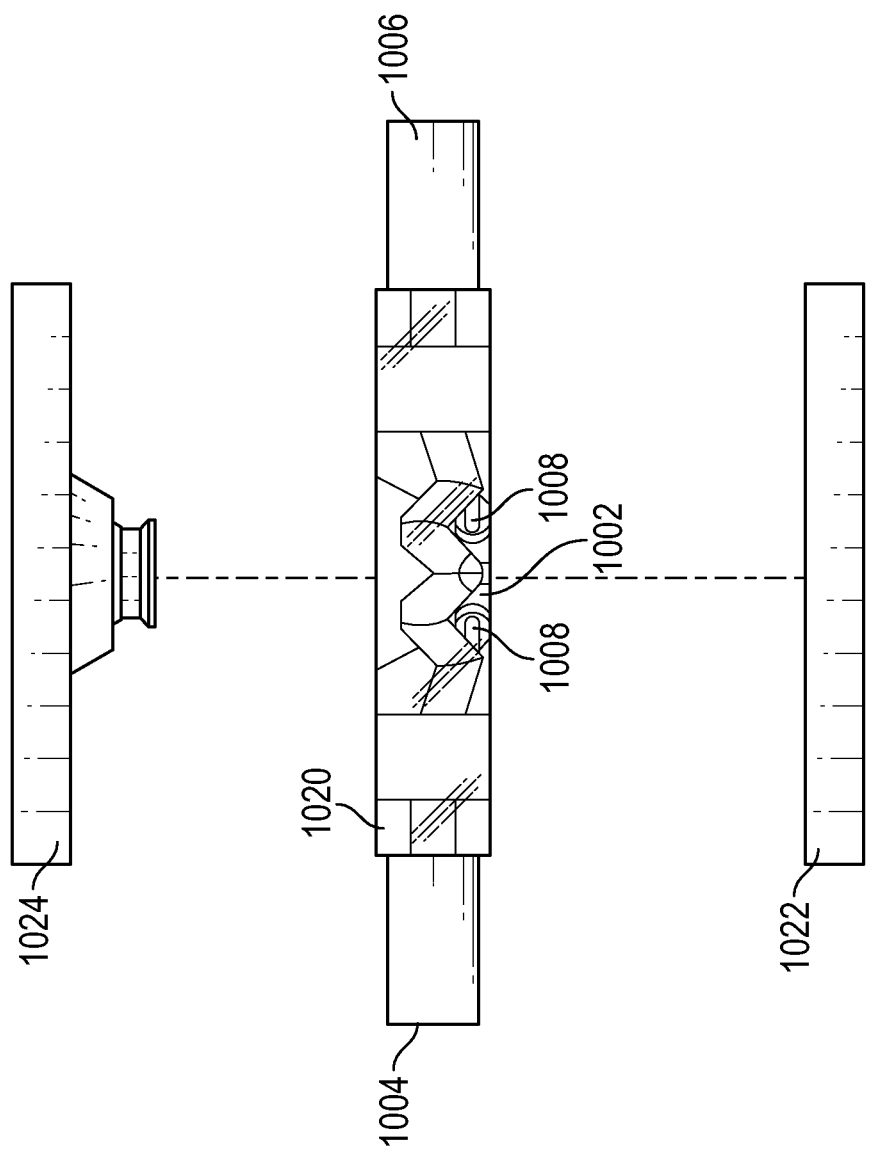
FIG. 24C is an exploded end view of the bioreactor of FIG. 24A.

FIGS. 24A-24C shows a biphasic single well system 1000 having two diffusion streams, one that feeds one half of a circular well 1002, and the other that feeds the other half of the circular well. As shown in FIG. 24A, the first fluid stream includes inlet 1004, outlet 1006, and radial diffusion channels 1008 that feed a first half of the circular well 1002. The second fluid stream includes inlet 1010, outlet 1012, and radial diffusion channels 1014 that feed a second half of the well 1002. The two fluid streams can feed different fluids to the two halves of the well, such as to feed two different cellular materials, or to cause a common cellular material to grow and differentiate into two different tissue types.

The system 1000 can also include a main body 1020, a lid 1022, and a base 1024, which can be attached together via aligned bolt holes, for example. The lid 1022 includes a viewing aperture 1026 that is positioned over the well 1002 with a transparent material, such as glass cover slip, blocking the aperture and sealing the top of the well. The base 1024 can be similar to the base 716. Gaskets, such as O-rings, can be included to seal the top and bottom of the well.

The well chamber containing the cells/construct can be fabricated in any shapes depending on the specific parameters desired to control fluid/molecule/protein transport and for the desired parameters for the cells/3D construct generation or maintenance. The fluidic paths can be modified according to the shape of the well and the desired results.

Figure 25A:
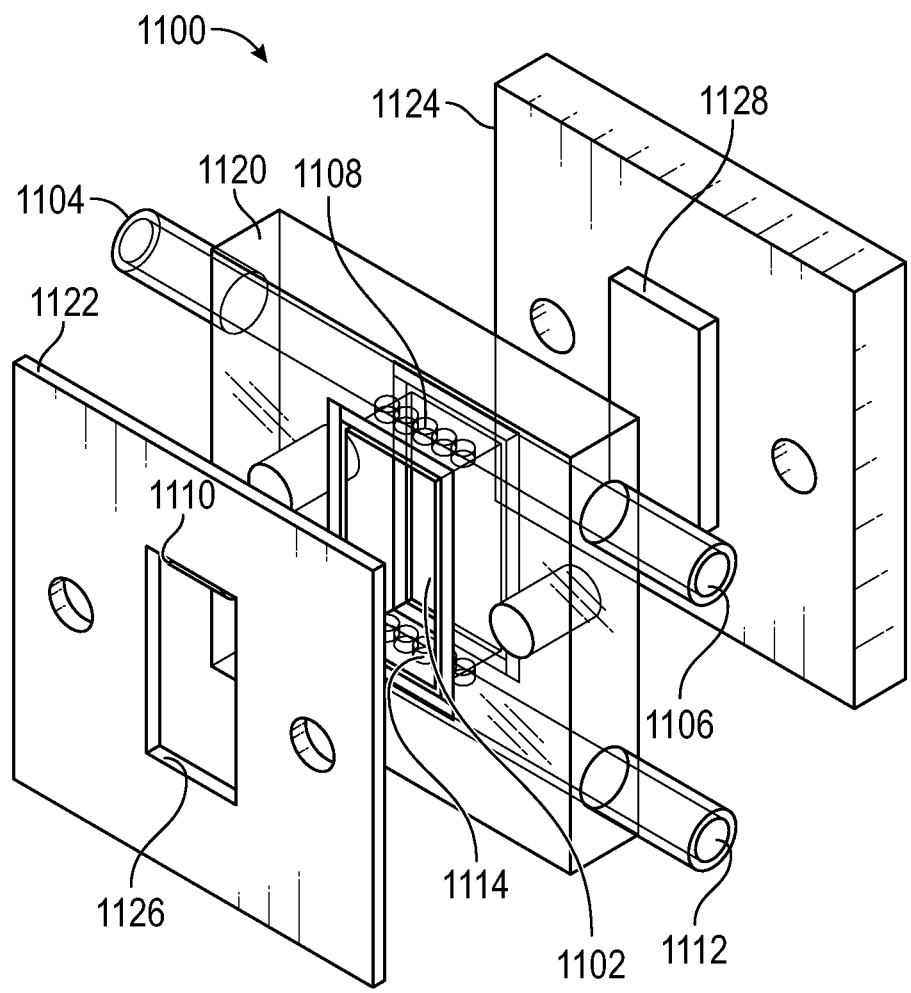
FIG. 25A is an exploded isometric view of an exemplary diffusion based rectangular bioreactor with two fluid inlets and two fluid outlets for a biphasic construct system.
Figure 25B:
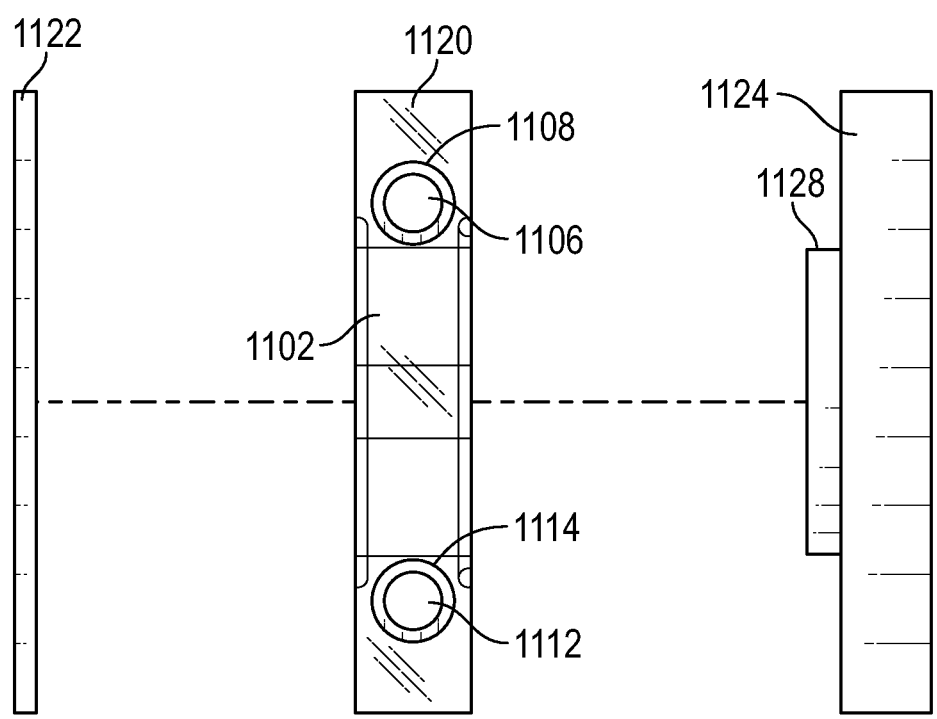
FIG. 25B is an exploded side view of the bioreactor of FIG. 25A.
Figure 25C:
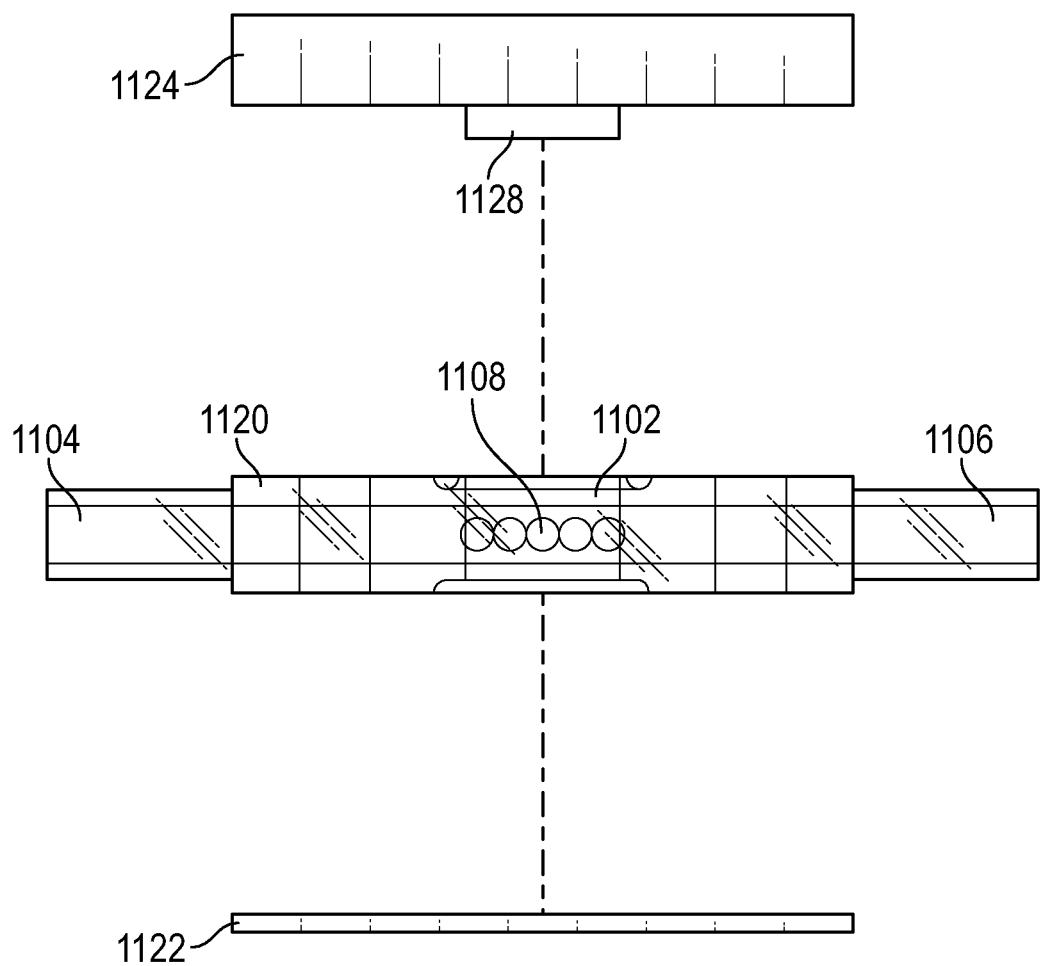
FIG. 25C is an exploded end view of the bioreactor of FIG. 25A.

FIGS. 25A-25C shows a biphasic single well system 1100 having two diffusion streams, one that feeds one end of a rectangular well 1102, and the other that feeds the other end of the rectangular well. As shown in FIG. 25A, the first fluid stream includes inlet 1104, outlet 1106, and diffusion channels 1108 that feed a first end of the rectangular well 1102. The second fluid stream includes inlet 1110, outlet 1112, and diffusion channels 1114 that feed a second end of the well 1102. The two fluid streams can feed different fluids to the two ends of the well, such as to feed two different cellular materials, or to cause a common cellular material to grow and differentiate into two different tissue types.

The system 1100 can also include a main body 1120, a lid 1122, and a base 1124, which can be attached together via aligned bolt holes, for example. The lid 1122 includes a viewing aperture 1126 that is positioned over the well 1102 with a transparent material, such as glass cover slip, blocking the aperture and sealing the top of the well. The base 1124 can include a raised rectangular surface 1128 that matches the shape of the well 1102 and forms the lower surface of the well when the base is attached to the main body. Gaskets, such as O-rings, can be included to seal the top and bottom of the well.

A plurality of the disclosed single-well systems can be fluidly coupled together to replicate the well positions of a 96-well plate or of a column/row of a 96-well plate. The single well systems can be coupled in series and/or in parallel in a multi-well system. When in series, the outlet of one or more wells can feed the inlet of one or more wells.

Figure 26A:
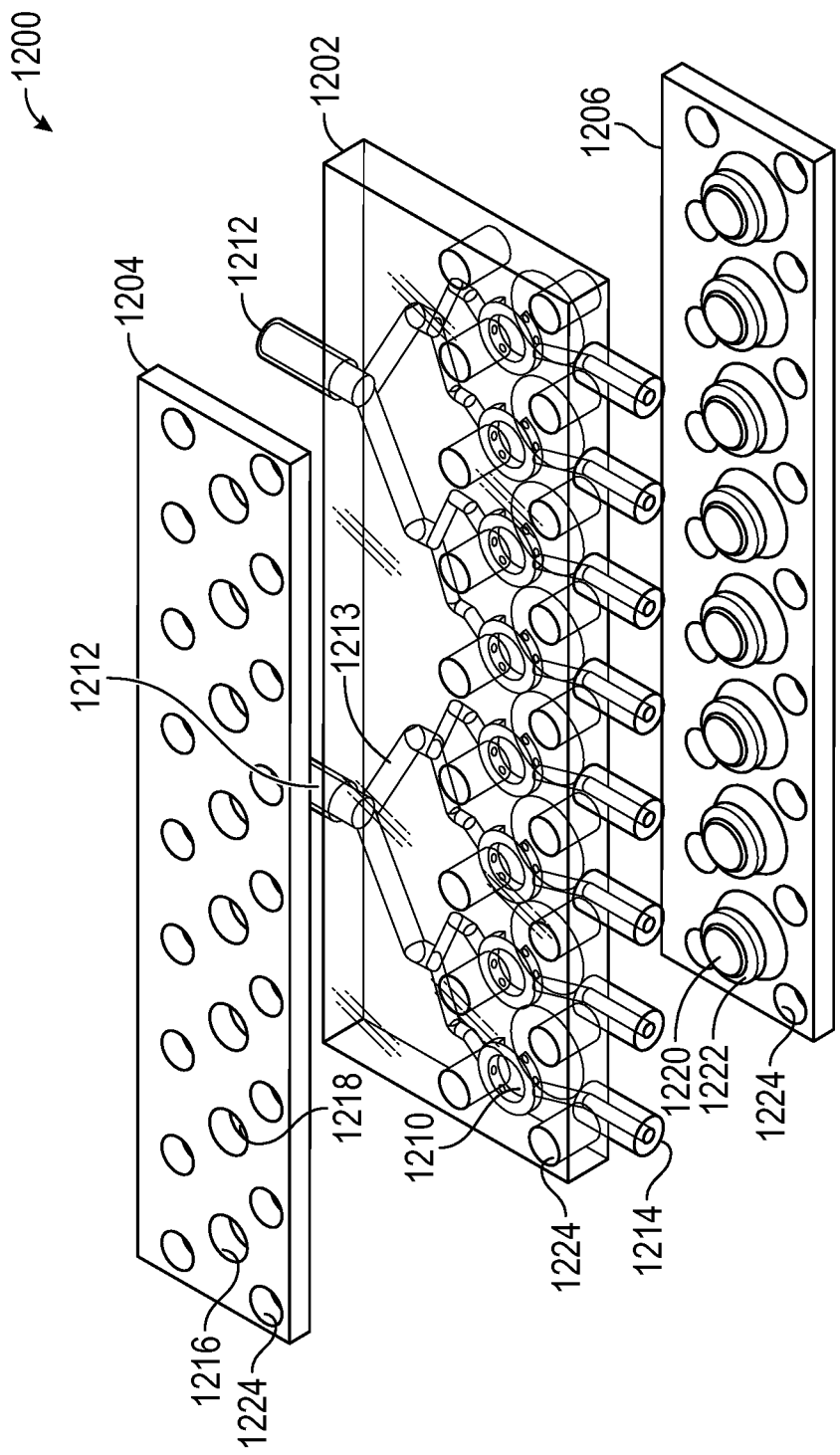
FIG. 26A is an exploded isometric view of a 1×8 well array bioreactor system for perfusion based fluid transport.
Figure 26B:
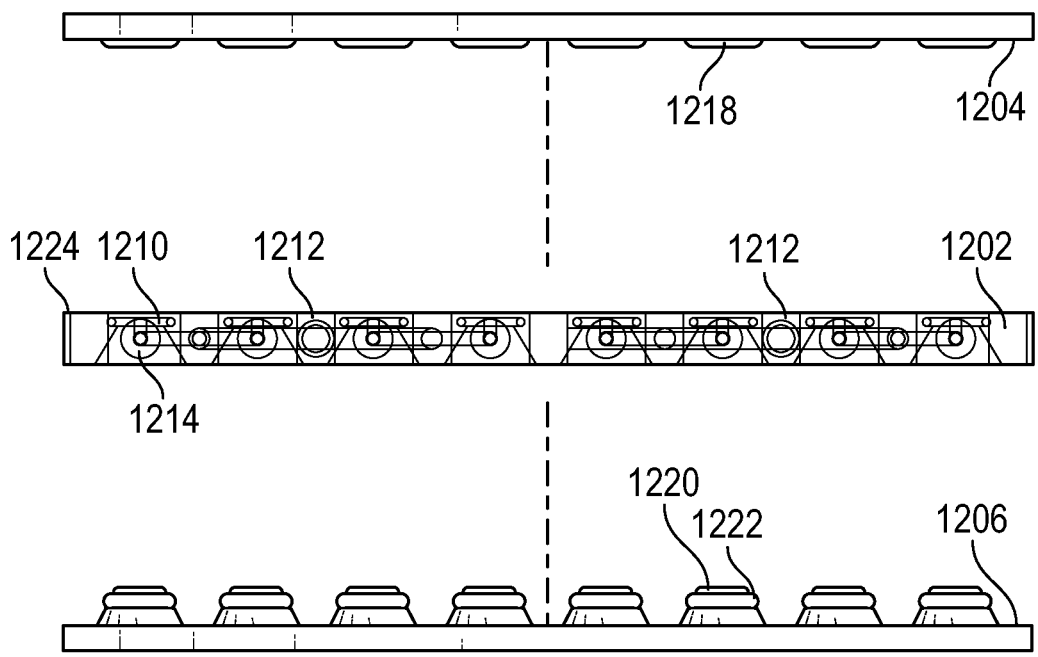
FIG. 26B is an exploded side view of the bioreactor system of FIG. 26A.
Figure 26C:
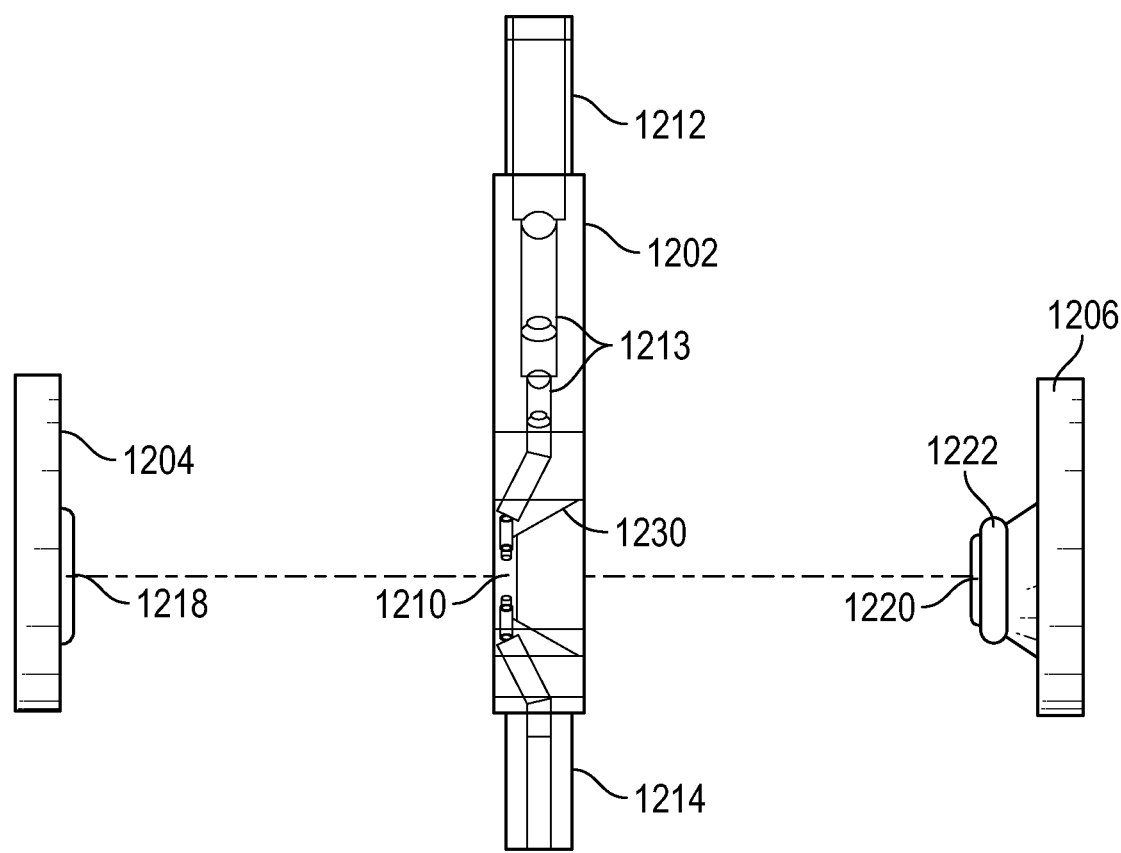
FIG. 26C is an exploded end view of the bioreactor system of FIG. 26A.

FIGS. 26A-26C shows a multi-well system 1200 comprising eight single stream perfusion based wells 1210 with two inlets 1212 that each branch into plural feeders 1213 so that each inlet feeds four of the wells. The system includes eight individual outlets 1214, one for each well 1210. The fluid that enters each inlet 1212 feeds four wells. Two different fluids can be used, one for each inlet 1212, to create four wells 1210 fed by one fluid and four wells 1210 fed by the other fluid.

The system 1200 can include a main body 1202 comprising the wells and conduits, a lid 1204, and a base 1206, which can be attached together via aligned bolt holes, for example. The lid 1204 includes viewing apertures 1216 that are positioned over the wells 1210 with a transparent material, such as glass cover slip, blocking each aperture and sealing the top of each well. The base 1206 can include raised surfaces 1220 that match the shape of the wells 1210 and form the lower surfaces of the wells when the base is attached to the main body. Gaskets, such as O-rings 1218 and 1222, can be included to seal the tops and bottoms of the wells.

Figure 27:
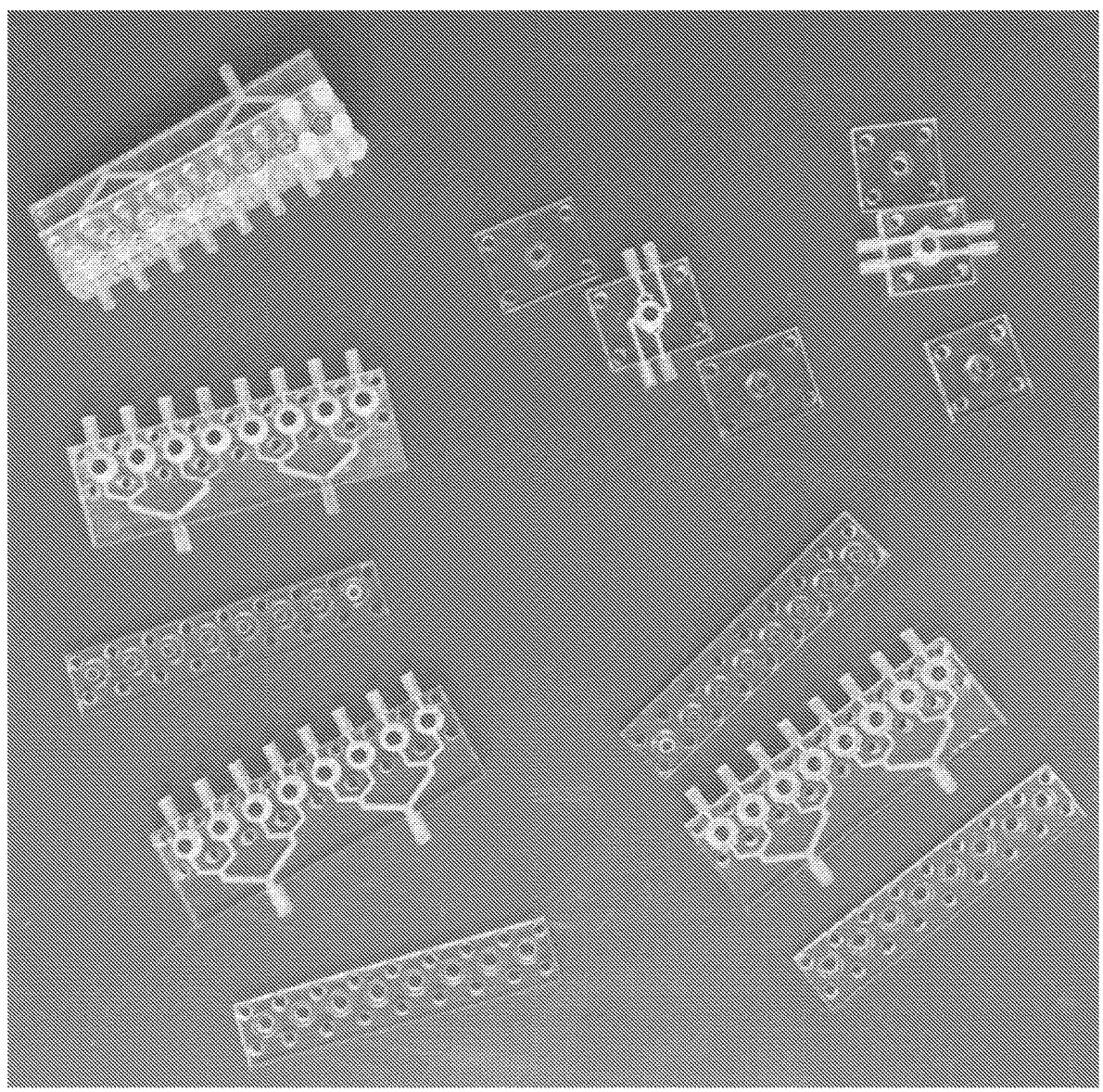
FIG. 27 shows several exemplary microfluidic microwell bioreactors, in various states of assembly.
Figure 30:
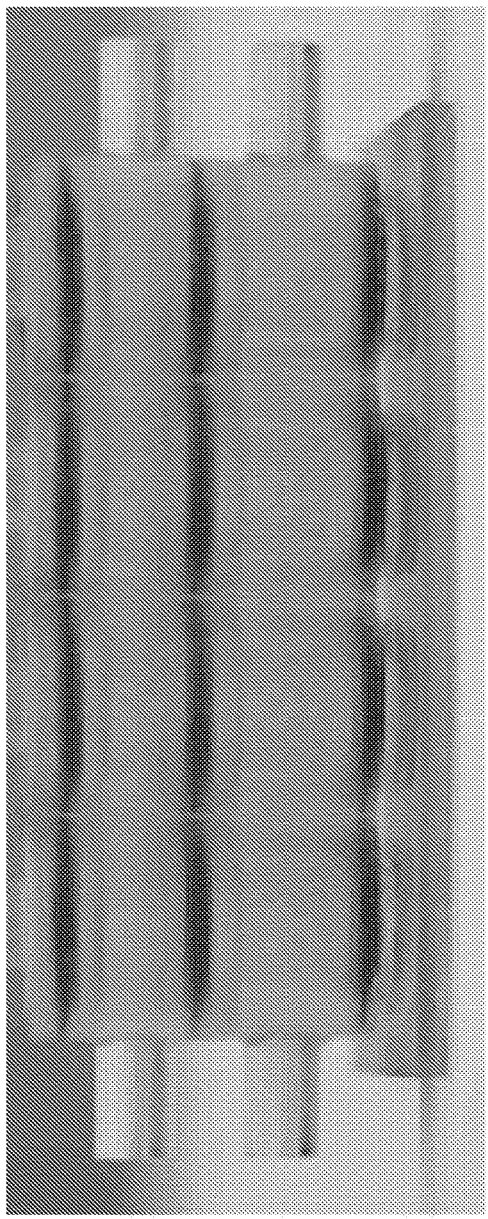
FIGS. 30 and 31 show an exemplary embodiment of the system of FIG. 28.
Figure 31:
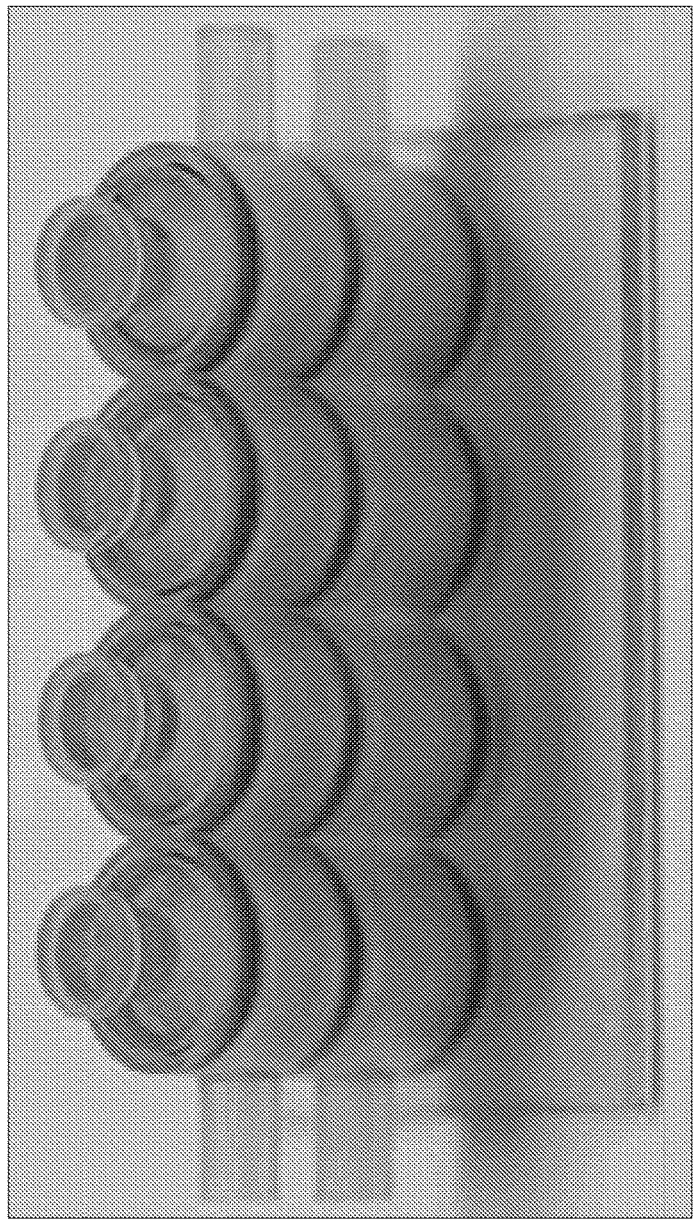

FIG. 27 is a photograph showing examples of several of the bioreactors as described herein fabricated using 3D printing.

In other embodiments, the inlets and/or outlets can be oriented on various other directions that what is shown in the preceding examples. For example, one or more of the inlets/outlets can extend perpendicular, or at other angles between 0°-90°, relative to the orientations shown in FIGS. 21-27. The inlets can also extend non-parallel with the outlets. In an example where there are 96 of the disclosed microwells dispersed across and planar array (similar to the arrangement of a conventional 96 well plate), some or all of the wells can have an inlet and an outlet that project upward substantially perpendicular to the plane of the 96 well array, thereby allowing each well to have individual access from above the array of wells. The inlets/outlets can also extend laterally in the plane of the well but perpendicular or at an angle to the general overall flow direction from the inlet to the outlet.

Inlet/outlet organization can be adapted following experimental needs from individual inlet and individual outlets to one common inlet for eight wells and one common outlet for all of them and any combination in between. In a similar manner, all individual well systems can be organized in arrays of single wells 1×1 (individual well) to multiple wells arranged 8×12 (96 well plate organization) and more in any geometry desired. The fluidic conduits of each array can allow for individual input/output for each well as well as serial or parallel connection of multiple inputs/outputs.

For example, a 1×8 combined diffusion/perfusion system may be created such that each microwell is supplied by its own perfusion inlet (in this case 8 separate inlets) connected to separate syringes controlled by a single syringe pump) to provide maintenance or stimulation media and having eight separate perfusion outlets, one per microwell, connected to individual collection bags to collect the perfusion fluid of each chamber, thus monitoring the response of each construct individually. For the diffusion fluidic in this example, the system can have 1 inlet for the diffusion fluid reaching well number 1 connected to syringe and pump, one outlet for the diffusion fluid exiting well 8 connected to a collection bag, the outlet of well 1 connected to inlet of well 2 and so on until the inlet of well 8. In such a setup, eight wells would share signals through diffusion and have individual perfusion media. Similar examples can be made for all types of fluidic systems, diffusion, perfusion, combined diffusion/perfusion, individual or multiple media inlet/outlet, serial and parallel arrangement for all shapes of wells.

Cells in a construct, for instance in a 3D hydrogel, can be polymerized in situ in the bioreactor or generated in a mold and then fit in the bioreactor. The shape of the hydrogels can be such that it fits perfectly the shape of the well. Alternatively the hydrogels can be shaped to only fit a subsection of the well while the rest is filled with a different material, the same hydrogel containing a different cell type, a hydrogel of complementary shape, another polymeric material, etc.

In exemplary methods, optical microscopy can be used to monitor and study vasculogenesis by GFP-labeled human umbilical vascular endothelial cells (HUVECs) in systems using either diffusion or perfusion to identify ideal conditions to generate in vitro microvasculature models. In some such methods, the method includes combining these HUVECs with osteoblasts (bone cells) to create a model of vascularized bone (two tissues). Some methods also include adding tumor cells into the medium stream and studying tumor cell homing, including tumor cell chemoattraction, rolling, adhesion, and/or transmigration through the endothelial wall into and through the osseous tissue, which can serve as an in vitro model of metastasis.

FIGS. 28-31 show an exemplary bioreactor system 1300 including four bioreactors joined in series with two inlets and two outlets for two fluid streams through the bioreactors.

The bioreactors of the system 1300 are similar to the embodiment 100 shown in FIG. 1, and include an outer housing 1302 and an inner structure 1304 that divides the bioreactor into plural chambers and can create outer fluid passageways around the constructs (e.g., an upper chamber coupled to the upper fluid stream and a lower chamber coupled to the lower fluid stream). Each bioreactor in the system 1300 also includes a removable lid 1306 and a removable base 1308, which can be sealed to the outer housing 1302 with O-rings, gaskets, and/or other means. The lids 1306 can be removed to access the upper chamber(s) of the bioreactor, and the base 1308 can be removed to access the lower chamber(s) of the bioreactors. A common base can be used that covers and seals all the bioreactors, or individual based can be used. Similarly, individual lids can be used, or a common lid that covers all the bioreactors can be used. The removable lids and base can allow the constructs to be more easily accessed for insertion, removal, inspection, cleaning, etc., and can make the system 1300 more reusable since the housing does not have to be broken/damaged to access the construct chambers.

Figure 43:
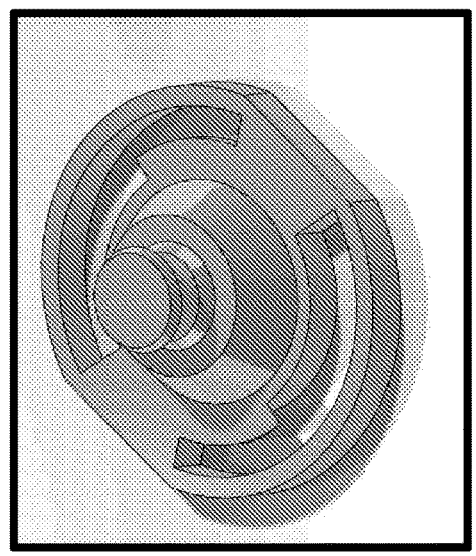
FIGS. 41-43 show three components that are assembled to form an exemplary bioreactor system with optical access.
Figure 42:
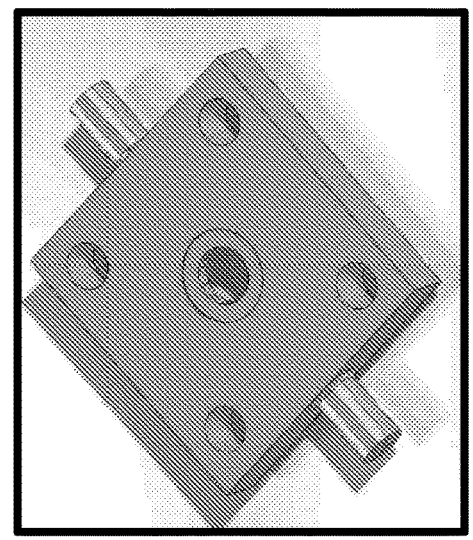
Figure 41:
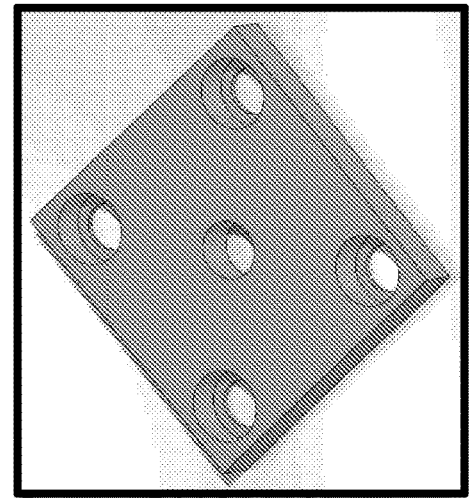
Figure 46:
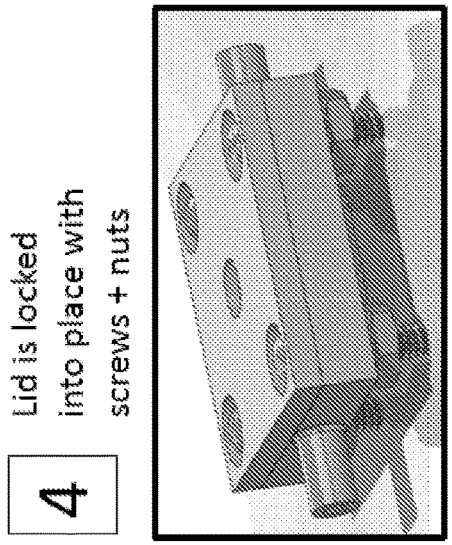
FIGS. 44-46 show assembly of a bioreactor from the components shown in FIGS. 41-43.
Figure 45:
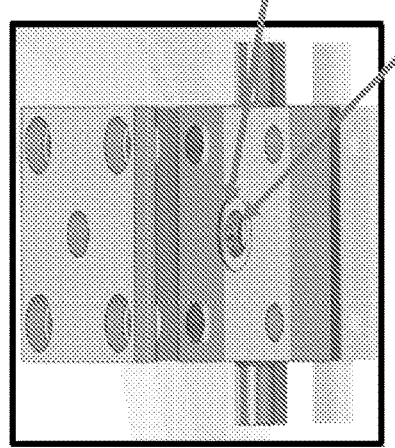
Figure 44:
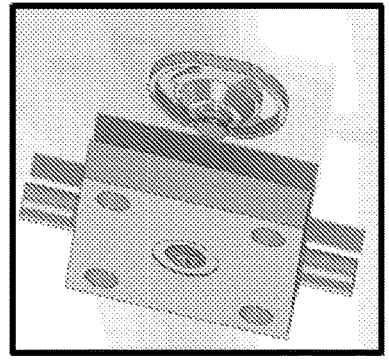
Figure 47:
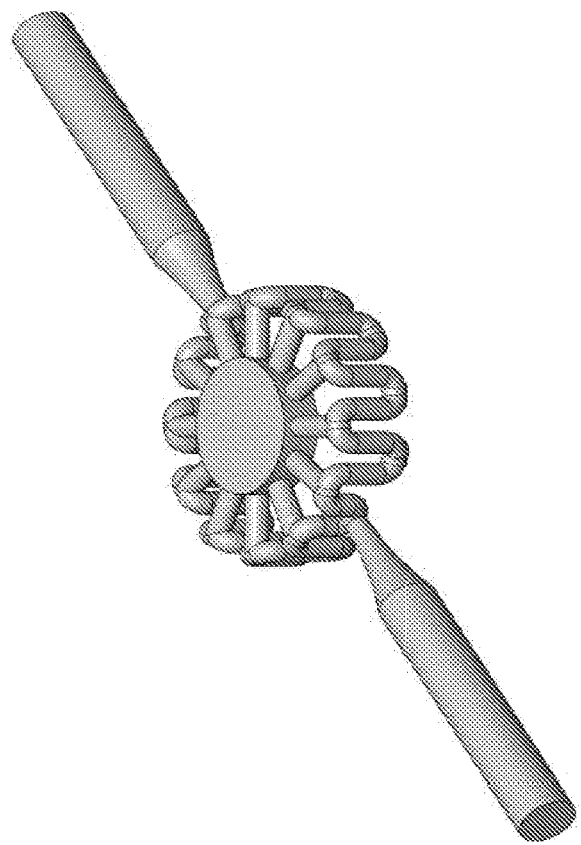
FIGS. 47 and 48 show the inner flow paths for embodiments of bioreactors having right-angled or step function shaped outer rings.

FIGS. 41-46 illustrate another exemplary bioreactor system having a single inlet and a single outlet (e.g., with the interior flow path shown in FIG. 47). FIG. 41 shows a top plate or lid, FIG. 42 shows the main body of the bioreactor including the flow path, and FIG. 43 shows the lower plate or base of the bioreactor. As shown in FIG. 44, the base can be inserted into the bottom of the main body of the bioreactor and locked in place by a mechanical connection that does not require bolts. For example, the base can be secured by rotating the base to cause interlocking members on the base and the main body to engage with each other and create a locked engagement that does not accidentally release. This can save time and cost (fewer parts, fewer steps, etc.) in the process of using the system, and can allow the overall bioreactor to have a thinner, lower-profile design. As shown in FIG. 45, biological material can be then be placed inside the central well and a transparent coverslip or cover (e.g., glass, polymeric, etc.) can be placed over the well. As shown in FIG. 46, the upper place or lid can then be secured over the top of the main body to seal the biological material in the well, while allowing visual access through the cover. The upper plate or lid can optionally also be secured to the main body via a mechanical locking mechanism, like what is shown for the lower plate or base. In some embodiments, the upper plate is not included, and the cover can be secured directly to the main body, covering the well, without another upper plate to hold the cover in place. For example, the cover can be secured to the main body around the perimeter of the well via an adhesive, a snap fit, friction fit, threaded engagement, magnetic attraction, other mechanical mechanisms, other forms of chemical bonding, etc. In some embodiments, the cover itself can comprise an adhesive film that is bonded directly over the well. In other embodiments, the cover can be pre-attached to the upper plate, or can be an integral portion of the upper plate, such that securing the upper plate to the main body simultaneously positions the cover over the well. Reducing the thickness of the upper plate or lid can allow a viewing instrument (e.g., a microscope or camera) to be placed closer to the cover and/or closer to the material inside the well. In any embodiment, it can be desirable for the cover to readily removable from the well to provide access into the well after viewing.

In any of the embodiments described herein, gaskets, O-rings, and/or other sealing materials can optionally be included between the main body and the other bioreactor components to help seal off the well. Furthermore, combinations of two or more of any of the disclosed bioreactor systems can be formed, similar to as shown in FIGS. 6A-6C and/or in FIGS. 26A-31.

FIG. 47 shows an exemplary flow path inside a bioreactor, such as that shown in FIGS. 41-46, that includes an undulating outer ring having substantially right angles or corners instead of a sinusoidal or wavy shape (like the design shown in FIGS. 21A-21D). (The solid volumes shown in FIGS. 47-51 and like figures herein are negatives that represent the open space and/or fluid flow paths inside the bioreactor systems.) The right-angled flow path shown in FIG. 47 can sometimes be referred to as a "step function" path. Such a right-angled or step function path design can allow the device to be manufactured easier, quicker, and/or less expensively, compared to sinusoidal or wavy designs.

Figure 48:
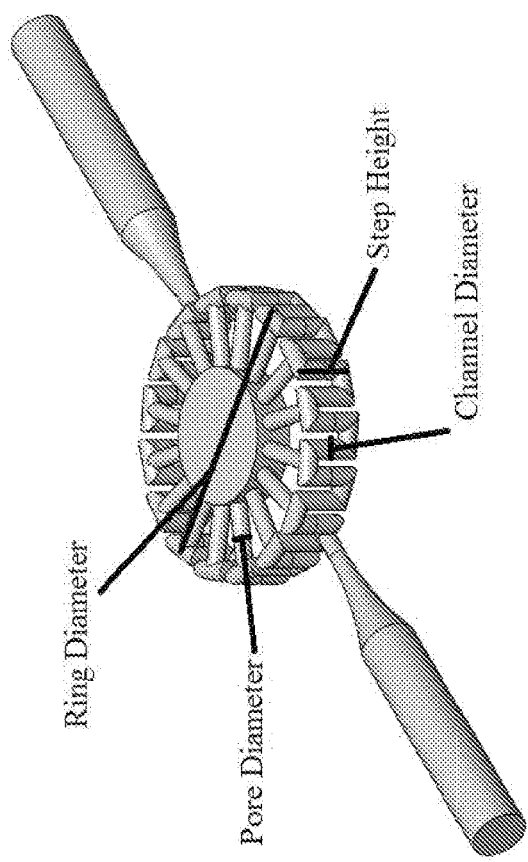

FIG. 48 shows another variant of a right-angled outer ring design. Velocity in the outer ring channels increases as the channel diameter decreases. Velocity also increases as the step height (vertical distance of each step) increases, providing more resistance. Velocity also increases as the number of pores increases. Velocity also increases as the overall ring diameter increases. Accordingly, these dimensions/parameters can be adjusted or selected to provide desirable flow properties in the outer ring and through the pores and through the cells in the well. In one embodiment, the outer ring channel diameter is about 0.60 mm, the pore diameters are about 0.60 mm, the step height is about 1.75 mm, the overall ring diameter is about 6.75 mm, and the number of pores and number of steps is 12.

Figure 49:
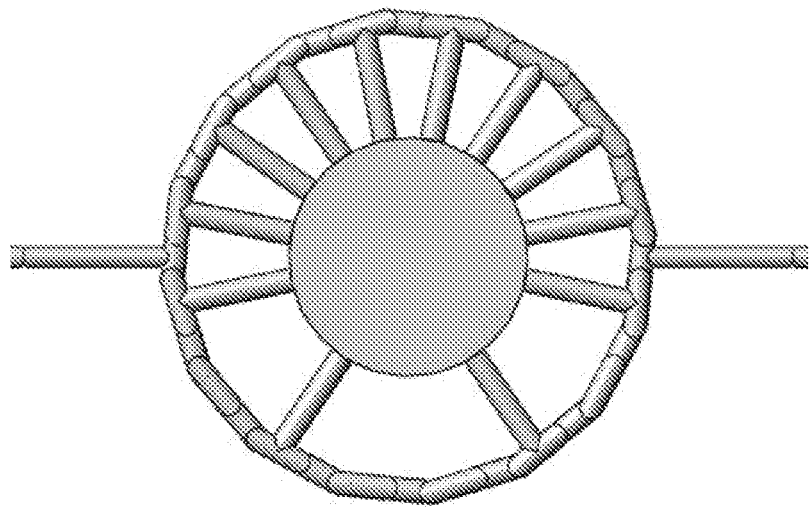
FIG. 49 shows a bioreactor flow path having an asymmetric outer ring, with one side having a larger diameter flow path.

FIG. 49 shows an exemplary bioreactor flow path where one side of the outer ring has an increase channel diameter relative to the other side, causing lower velocity and higher volume flow in the side with the larger diameter.

Figure 50:
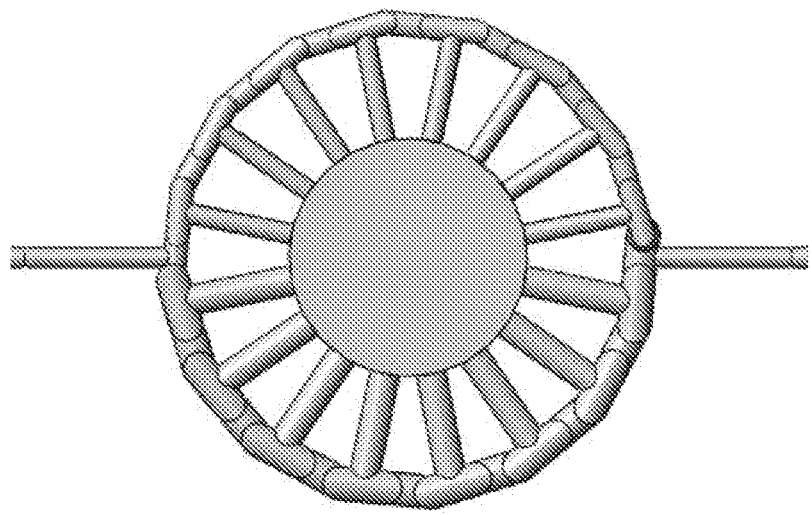
FIG. 50 shows a bioreactor flow path having an asymmetric arrangement of pores extending from the outer ring to the central well.

In alternative embodiments, one or more of the pores can be closed off or removed from the outer ring to change to flow properties. For example, FIG. 50 shows an embodiment with some of the pores removed from one side of the ring. This can create an asymmetric pore pattern and an asymmetric flow pattern though the well.

Figure 51:
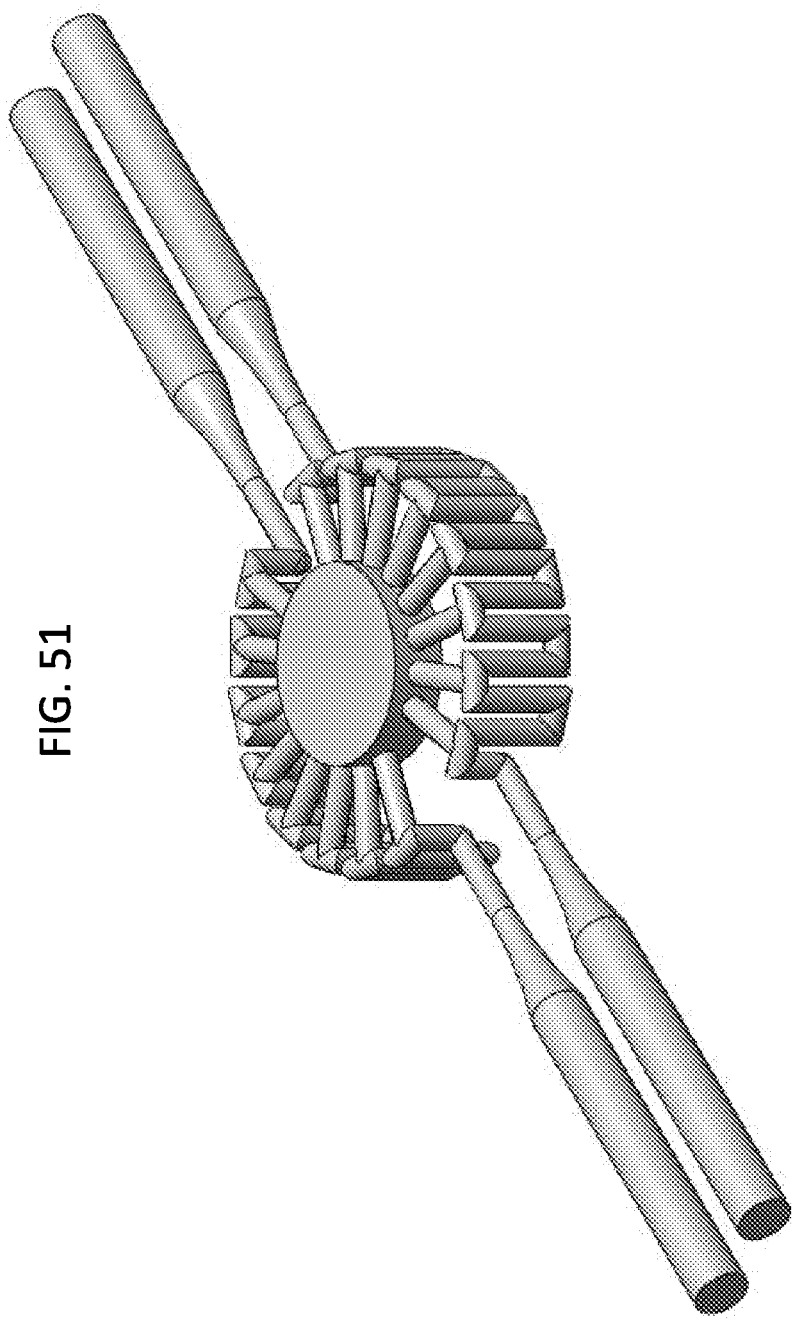
FIG. 51 shows the inner flow paths for an embodiment of bioreactor having two discrete flow paths with right-angled or step function shaped flow paths.

FIG. 51 shows another right-angled outer ring design with two inlets and two inlets, one for each side of the outer ring. This allows greater control of the flow on either side of the ring, independent of the other side. Any of the parameter variations discussed herein can also be applied to the dual-path embodiment of FIG. 51.

The fluid flow properties within the well of the disclosed bioreactors can also be effected by the material properties of the material in the well. In some embodiments, the material in the well can be non-uniform in permeability, such as with one type of material on one lateral side of the well and another type of material on the other side of the well, or more than two different types of materials in discrete zones of the well. For example, if one material is more permeable to the fluid being supplied by the bioreactor, that can cause an increase in fluid flow through the pores on that side of the reactor, and a decrease in the fluid flow around the outer ring on that side of the reactor.

Any of the bioreactor systems disclosed herein can be used to:

test exposure to different growth factors sequences of different cell types in single culture or co-culture (e.g., MSCs, HUVECs, osteoblasts, osteoclasts, T-cells, adipocytes, neuronal cells, etc.) to access cell response;

use cells transduced with fluorescent reporter genes to monitor response to stress or differentiation in response to exposure to specific growth factors, candidate drug compounds, and known or unknown toxicants;

use various different scaffolds to test support to cells growth, proliferations, and differentiation;

test drug compounds candidates and/or toxicants to model tissue/cell response in vivo;

combine different tissue types in series, within the bioreactor or with other bioreactors, to assess tissue-tissue cross-communication; and model various tissues and organs in the bioreactor, including musculoskeletal tissues (cartilage, bone, tendons, ligaments, etc.), adipose, vascular, neural, lymph nodes, combinations thereof, etc.

Understanding Fluid Movement Through Bioreactors Using Circuit Comparisons

A bioreactor can be treated as an element which dissipates pressure as a volume flows through it. Each design element that makes up the flow path of the bioreactor has its own effect on the pressure drop over the entire system Summing these elements as resistors allows for the resistance of the central chamber to be found. By knowing this resistance, the bioreactor and methods for maximizing drug exposure through the cells can be better understood.

Bioreactor technologies employ the use of an apparatus in which to place and maintain tissues or cells whose response to a candidate drug can be monitored and studied. When screening drugs, an exit for air bubbles can be beneficial as they tend to build up around the flow path; therefore, diffusion is the primary method of transport for the drugs and nutrients. The design shown in FIG. 47, for example, uses diffusion as its method of transport as the fluid may go through the central chamber housing the cells but also has the option to continue around the step function outer path while never making contact with the cells in the middle.

Figure 52:
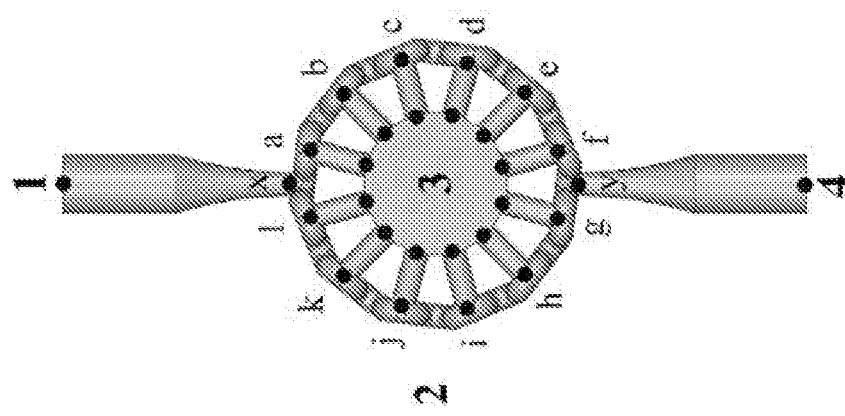
FIG. 52 is a node-based illustration for analyzing fluid flow within a bioreactor.

Inside of this central chamber, the cells exist in a medium with a low permeability resulting in low amounts of drug exposure. This system can be studied further to develop pressure relationships around the entire bioreactor in order to understand how pressure gradients force the fluid through the model. The difference in pressure between two points can be represented as:

$$\Delta p = Q^* R_T \quad (1)$$

Where $\Delta p$ is the pressure upstream minus the pressure downstream, Q is the volume flow rate, and $R_T$ is the hydraulic resistance. This equation is very similar to Ohm's Law which can be rewritten as:

$$\Delta V = I^* R \quad (2)$$

where V is the voltage, I is the current, and R is the resistance. Under this comparison, pressure is equivalent to voltage, volume flow is equivalent to current, and both resistances are equivalent. Using this comparison, the entire bioreactor can be viewed as a combination of resistors which, instead of producing voltage drops as current runs through them, produce a pressure drop as volume flows through them. Nodes can be placed around the bioreactor as shown in FIG. 52. Resistors can be placed between these nodes in order to represent paths with a pressure drop leading to the equivalent circuit represented in FIG. 53.

Understanding how these resistors dissipate pressure will give a better understanding as to how the fluid is being forced through the test cells and through the bioreactor. When this bioreactor system is used in drug screening, one pump is responsible for forcing the drug candidate through multiple bioreactors. This can be accomplished by placing the systems in series, parallel, or a combination of both. As the fluid moves through each bioreactor, the pressure will decrease but the pressure drop across each bioreactor should remain the same. Understanding this relationship will convey how the pressure is dependent on how the bioreactors are aligned.

Because the bioreactor is open at its outlet, the exit pressure is effectively 0 Pa meaning that, from Equation 1, the hydraulic resistance of the entire bioreactor is equal to the inlet pressure divided by the volume flow rate. These values can be found after running an ANSYS simulation on the bioreactor model using Fluid Flow (CFX) with a volume flow rate of 1 mL/day which converts to $1.15741*10^{-11}$ m$^3$/s. The middle of the model is represented as GelMA which has a permeability of $1*10^{-16}$ m$^2$ and a porosity of 0.8. All other pressures for each node in FIG. 53 can also be found. Results show that a pressure of 0.0470599 Pa exists at the inlet. Plugging the inlet pressure and volume flow rate into Equation 1, the hydraulic resistance is found to be $4.066*10^9$ kg/m$^4$·s for the entire bioreactor.

Now that the total resistance is known, the next step is to solve for the resistances of the different parts of the bioreactor. There are five main parts to the model: the inlet/outlet, the small step from the inlet/outlet to the first pore, the step between pores, the pores, and the cell construct. The cell construct presents different resistance values for each resistor as they are all different lengths; however, when looking at the results from the CFX simulation in FIG. 54, the flow is observed to mix about the side most pores meaning that these resistors are effectively the same resistance value. For this reason, the circuit in FIG. 53 can be given the labels seen in FIG. 55.

$R_o$ is the resistance of the inlet/outlet, $R_i$ is the resistance of the small step from the inlet/outlet to the first pore, $R_s$ is the resistance of the step between pores, $R_p$ is the resistance of the pores, $R_1$ is the resistance of the first stream within the cell construct, and $R_2$ is the resistance of the sides of the cell construct.

Figure 56A:
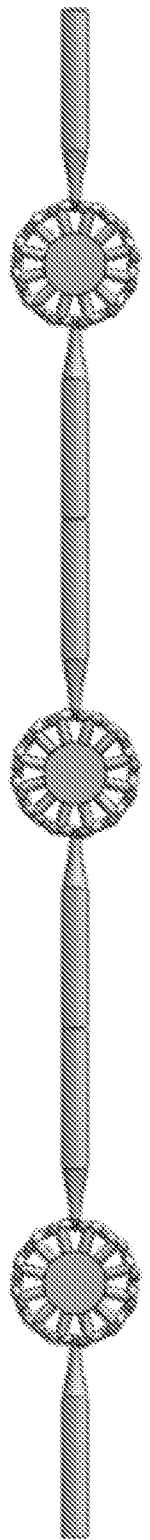
FIGS. 56A and 56B show multi-reactor system configurations that share fluid flow paths.
Figure 56B:
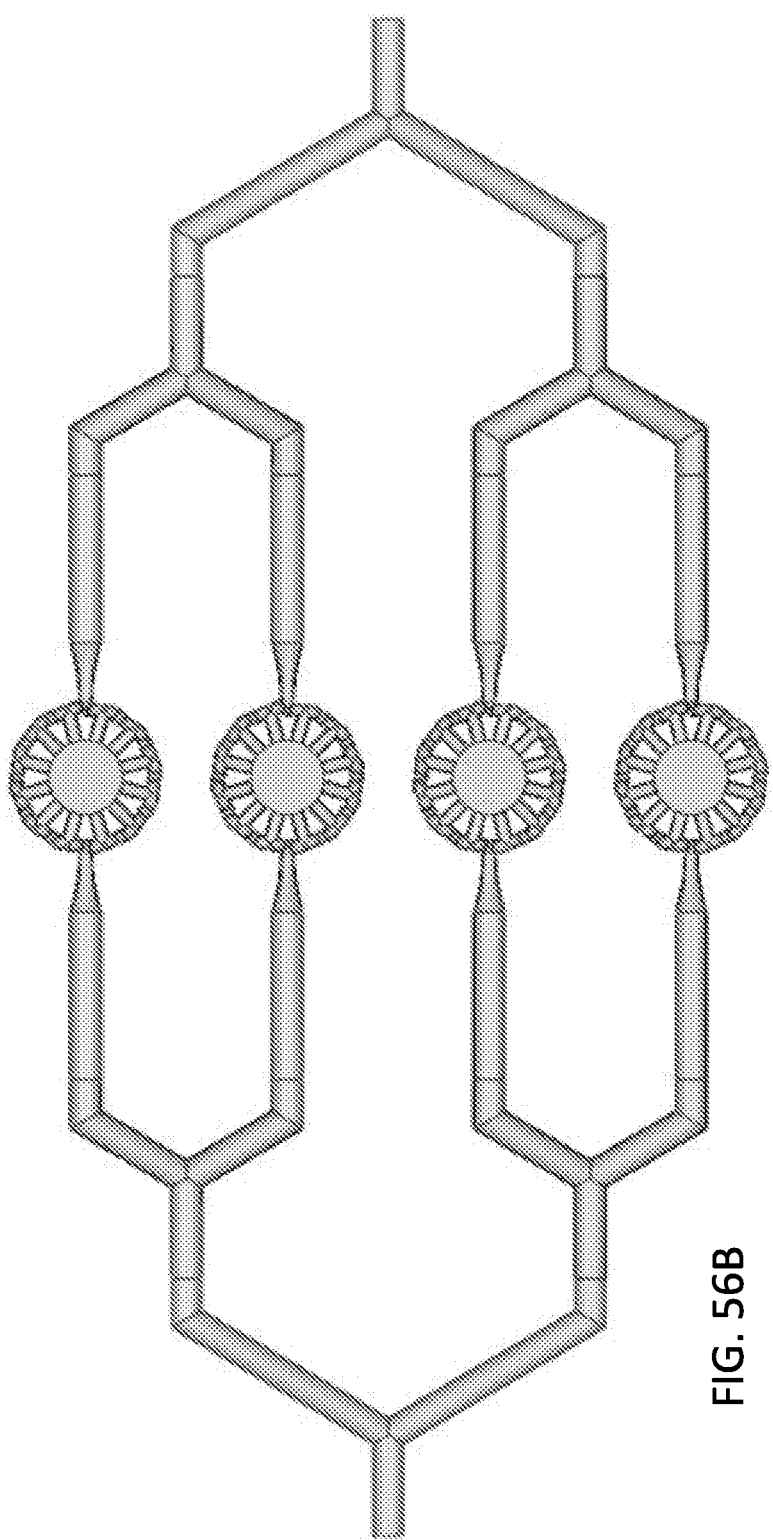

Models can also be made which place multiple bioreactors in series or parallel. Examples of these models can be seen in FIGS. 56A and 56B. In these models, each individual bioreactor is considered a resistor. Similar ANSYS simulations can be performed on these models as was done with the previous model.

Figure 55:
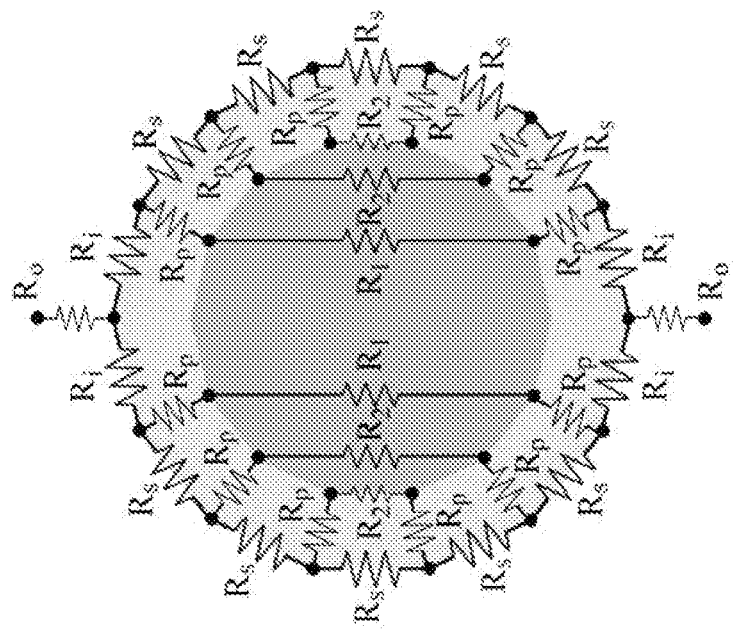
FIG. 55 is another circuit-based illustration for analyzing fluid flow within a bioreactor.

$R_o$ and $R_i$ from FIG. 55 can be solved for as the pressures at the nodes are known, which can be found in Table 1 below, as well as the volume flow through $R_o$ which is 1 mL/day and through $R_i$ which is 0.5 mL/day since flow through the bioreactor is symmetric. The resistance values of each of these resistors were found using the pressure data, and like resistors were averaged to find the average resistance of the two elements.

TABLE 1

Pressure values at nodes corresponding to FIG. 52 (units in Pa)

|   | 1 | 2 | 3 | 4 |
|---|---|---|---|---|
| a | 0.0470599 | 0.0403718 | 0.0404114 | 0 |
| b |   | 0.336566 | 0.033692 |   |
| c |   | 0.0269156 | 0.0269621 |   |
| d |   | 0.0201338 | 0.0201738 |   |
| e |   | 0.0134233 | 0.0134657 |   |
| f |   | 0.00668161 | 0.006728 |   |
| g |   | 0.0067053 | 0.00666553 |   |
| h |   | 0.0133993 | 0.013354 |   |
| i |   | 0.0201436 | 0.0200961 |   |
| j |   | 0.0269303 | 0.0268933 |   |
| k |   | 0.0336025 | 0.0335603 |   |
| l |   | 0.0403574 | 0.0403069 |   |

TABLE 1-continued

Pressure values at nodes corresponding to FIG. 52 (units in Pa)

| | 1 | 2 | 3 | 4 |
|---|---|---|---|---|
| x | | 0.0424997 | | |
| y | | 0.00457554 | | |

In order to find the resistance of the pores, $R_p$, and the step between the pores, $R_s$, individual models were made of each part which were then tested in ANSYS. This approach finds the resistance directly. The resulting resistances can be found in Table 2 below.

Figure 57:
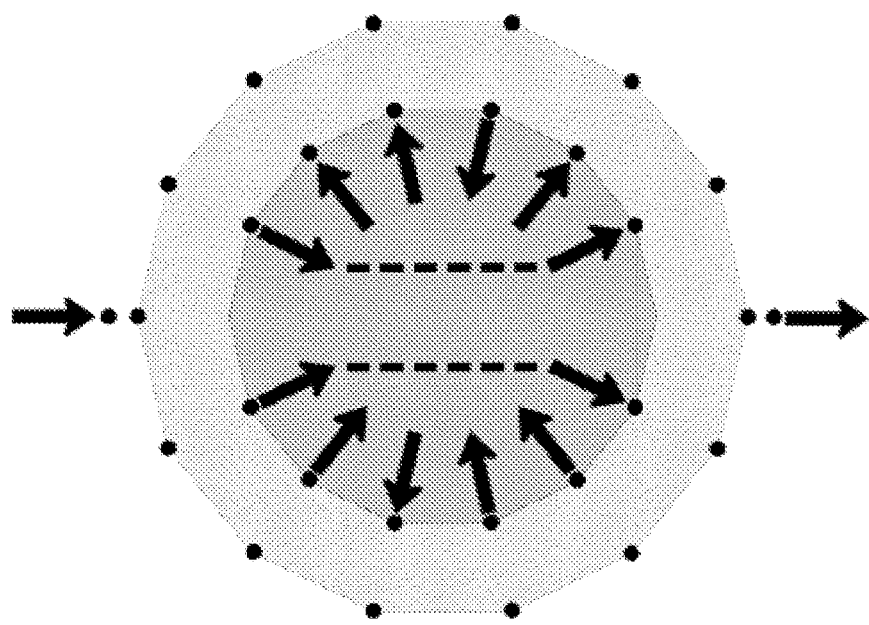
FIG. 57 shows generalized flow directions through the pores in a bioreactor.

Now the only unknown resistance values are $R_1$ and $R_2$ which correspond to the resistance of the cell construct. Knowing the pressure differences around the step function ring and the resistance of each step, the volume flow can be solved for each portion of the ring. This can be used to determine the amount of volume entering and leaving the cell construct. Doing so produces an idea of how the flow is entering and exiting the central chamber seen in FIG. 57.

Figure 54:
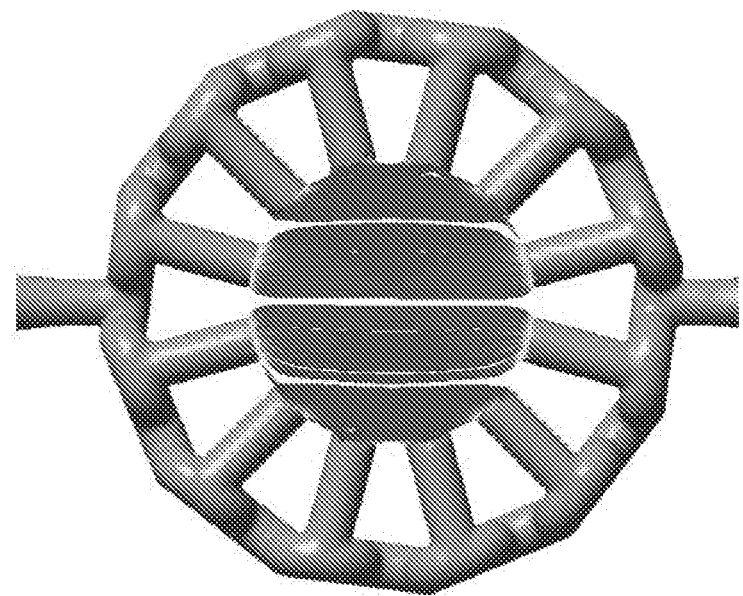
FIG. 54 is a simulation showing fluid flow paths through the central well of a bioreactor.

This flow agrees with the simulation results seen in FIG. 54 as there are two bands down the middle with chaotic clusters at the sides. Knowing the volume flow at every portion of the step function ring means that the volume flow through $R_1$ is known for both sides of the bioreactor as it is simply the volume flow from 2x to 2a minus the volume flow from 2a to 2b for the right side and is done in a similar manner for the left side. Computing the average between these two values leads to the hydraulic resistance of the inner portion of the cell structure. The value can be found in Table 2 below.

TABLE 2

Hydraulic resistance values of design features

| Feature | Hydraulic Resistance, $R_T$ (kg/m$^4$ · s) |
|---|---|
| Inlet/Outlet, $R_o$ | 394.663e6 |
| Initial/Final Step Segment, $R_i$ | 367.460e6 |
| Full Step, $R_p$ | 1.259e9 |
| Pore, $R_p$ | 377.591e6 |
| Inner Cell Structure, $R_1$ | 77.564e9 |
| Entire Bioreactor, $R_T$ | 4.066e9 |

Figure 53:
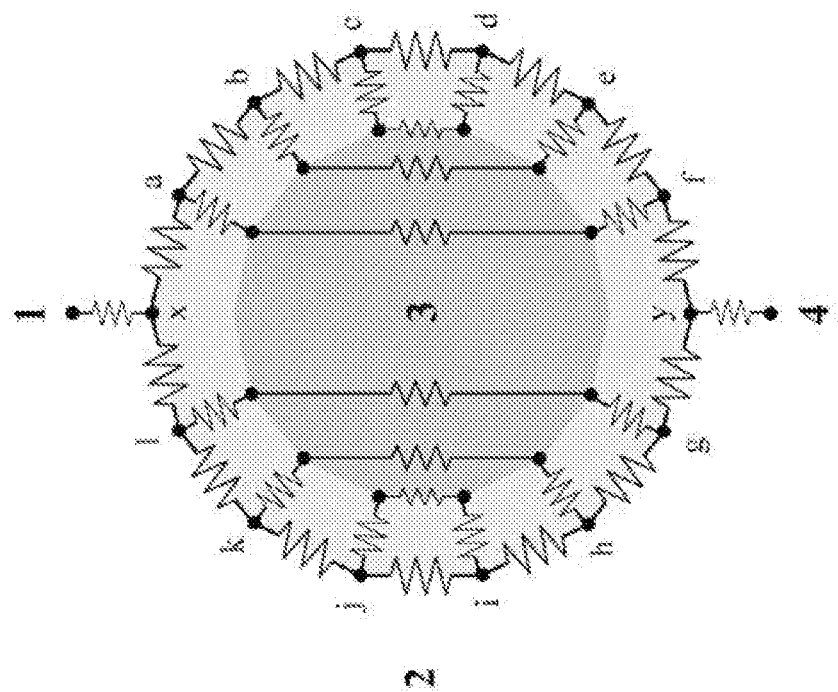
FIG. 53 is a circuit-based illustration for analyzing fluid flow within a bioreactor.

The only unknown is $R_2$ which can be solved for by making an equivalent circuit of FIG. 53. The circuit can be simplified in twelve steps by taking advantage of the fact that the circuit is symmetric about its two sides. After simplifying the entire circuit down to one resistor, its equivalent resistance is equal to $$4.071*10^9 \frac{6.795*10^{18}(R_2 + 1.511*10^9)}{R_2^2 + 6.361*10^9 * R_2 + 7.264*10^{18}} \tag{3}$$

The resistance of the entire bioreactor, $R_T$, is known, so $R_2$ can be solved for. This leads to two solutions: −1.511e9 and 1.3088e12. Only the positive value makes sense; therefore, the resistance of the sides of the cell construct is equal to 1.309e12 kg/m$^4$·s.

Controlling the hydraulic resistance of the entire bioreactor can be just as important as understanding the resistance of each path, for the resistance of the bioreactor seems to be directly related to the velocity of the fluid through the central chamber meaning that there is a high drug exposure over time. Different features of the design of the bioreactor can be changed in order to see if they have any effect on the hydraulic resistance of the entire system. These features include the height of the step function and the diameter of the channel and pores.

Figure 58:
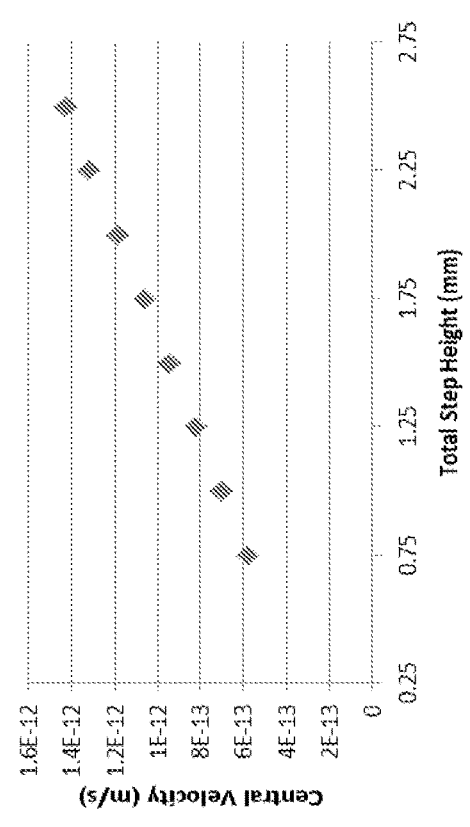
FIGS. 58 and 59 are plots of central fluid flow velocity and hydraulic resistance as a function of total step height in the outer ring.
Figure 59:
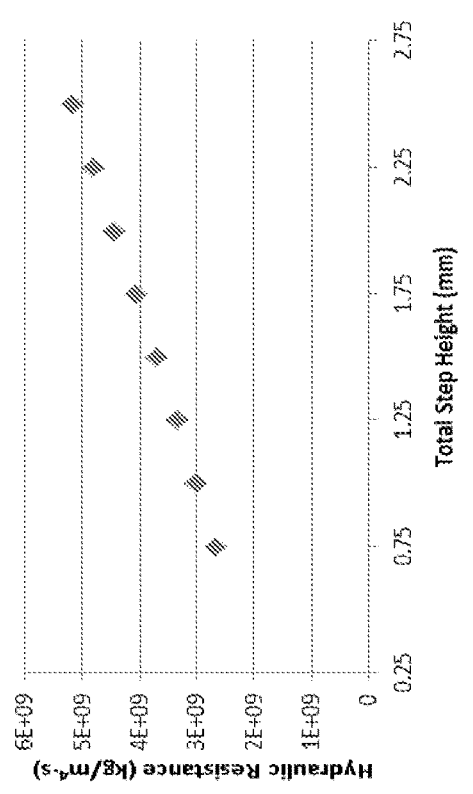

Looking first at changing the height of the step function, the change has an obvious effect on both the velocity through the central chamber and also on the hydraulic resistance of the entire system. Data can be seen in Table 3 below, which is plotted in FIGS. 58 and 59. The channel diameter was kept constant at 0.60 mm for all models.

TABLE 3

Data obtained from increasing step height of bioreactor while channel/pore size remained constant

| Total Step Height (mm) | Velocity Through Central Chamber (m/s) | Hydraulic Resistance, $R_T$ (kg/m$^4$ · s) |
|---|---|---|
| 0.75 | 5.800e−13 | 2.672e9 |
| 1.00 | 6.992e−13 | 3.011e9 |
| 1.25 | 8.202e−13 | 3.342e9 |
| 1.50 | 9.438e−13 | 3.706e9 |
| 1.75 | 1.060e−12 | 4.066e9 |
| 2.00 | 1.188e−12 | 4.439e9 |
| 2.25 | 1.317e−12 | 4.815e9 |
| 2.50 | 1.429e−12 | 5.177e9 |

It is apparent that increasing the step height also increases the velocity through the central chamber as well as the hydraulic resistance. The relationship between the step height and resistance can be seen in Equation 4 where H is the step height is in meters.

$$R_T = 1.4387*10^{12}*H + 1.5654*10^9 \tag{4}$$

The same process can be done with the channel and pore diameter. Increasing these has a much more interesting effect on the hydraulic resistance of the model. Data can be seen in Table 4 below, which is plotted in FIGS. 60-63. The step height was kept constant at 1.75 mm for all models.

TABLE 4

Data obtained from increasing channel/pore size of bioreactor while step height remained constant

| Channel/Pore Diameter (mm) | Velocity Through Central Chamber (m/s) | Hydraulic Resistance, $R_T$ (kg/m$^4$ · s) |
|---|---|---|
| 0.35 | 6.780e−12 | 31.182e9 |
| 0.40 | 4.323e−12 | 18.820e9 |
| 0.45 | 2.962e−12 | 12.279e9 |
| 0.50 | 2.003e−12 | 8.198e9 |
| 0.55 | 1.456e−12 | 5.724e9 |
| 0.60 | 1.060e−12 | 4.066e9 |
| 0.65 | 7.947e−13 | 3.029e9 |

Initially, the data is non-linear; however, whenever the log of the data is taken, a nearly perfectly linear relationship emerges. The relationship between the channel diameter and resistance can be seen in Equation 5 where D is the diameter of the channel and pores in meters.

$$R_T = 2.9114*10^{-3}*D^{-3.7708} \tag{5}$$

The relationships seen in FIGS. 58-63 convey that the hydraulic resistance has a direct impact on the velocity of the fluid through the central chamber and therefore the attained drug exposure. Equation 4 and Equation 5 can be used to maximize the hydraulic resistance of the model to maximize drug exposure.

When the bioreactor is placed in an array, the pressure drop across the entire model is dependent solely upon the volume flow rate through the model as is evident from Equation 1 as the resistance remains constant. Bioreactors in series offer a simple equivalent hydraulic resistance expressed in Equation 6 where N is the number of identical bioreactors in series and Δp is the inlet pressure minus the outlet pressure across the entire array.

$$R_T = \frac{R_{eq}}{N} = \frac{\Delta p}{N*Q} \quad (6)$$

To validate this equation, different number of bioreactors can be placed in series, and the inlet pressure can be measured. With this, the hydraulic resistance of one element can be found. Results can be seen in Table 5 below.

TABLE 5

Data for bioreactors in series

| Number of Bioreactors, N | Total Pressure Drop, Δp (Pa) | Hydraulic Resistance, $R_T$ (kg/m$^4$ · s) |
| --- | --- | --- |
| 1 | 0.0470599 | 4.06597e9 |
| 2 | 0.0943209 | 4.07465e9 |
| 3 | 0.141392 | 4.07208e9 |
| 4 | 0.188262 | 4.06645e9 |
| 5 | 0.235547 | 4.07024e9 |

All hydraulic resistances are very similar with an average value equal to 4.06987309e9 kg/m$^4$·s with a standard deviation of 0.00370e9 kg/m$^4$·s. The same method is done to test the bioreactors in parallel. One difference, however, is that the parallel model contains extra path length as is evident from FIG. 56B. This extra geometry contains its own resistance and therefore must be represented by its own resistor. This can be done by averaging the pressures at the inlet of each bioreactor, plugging this into Equation 1, and solving for the resistance with a volume flow rate of 1 mL/day. The same method is done for the outlet flow path. The two resistances can be averaged leading to the resistance of the flow path. This leads to the values in Table 6 below.

TABLE 6

Data for parallel pipe

| Element | Average Pressure Drop, Δp (Pa) | Hydraulic Resistance, $R_T$ (kg/m$^4$ · s) |
| --- | --- | --- |
| 2 Element Parallel Pipe | 0.000673 | 58.135e6 |
| 4 Element Parallel Pipe | 0.001264 | 109.198e6 |

Knowing these values, the equivalent resistance of the bioreactor array can be expressed with Equation 7 by combining the bioreactors in series as resistors in series and then combining these as resistors in series with the piping.

$$R_T = N*R_{eq} = N\left(\frac{\Delta p}{Q} - 2R_{piping}\right) \quad (7)$$

Using the values in Table 6 above, Equation 7 can be used to solve for the hydraulic resistance of each bioreactor to confirm that it is close to the actual value. Doing so yields the results seen in Table 7 below.

TABLE 7

Data for bioreactors in parallel

| Number of Bioreactors, N | Pressure Drop Over System, Δp (Pa) | Hydraulic Resistance, $R_T$ (kg/m$^4$ · s) |
| --- | --- | --- |
| 1 | 0.0470599 | 4.06597e9 |
| 2 | 0.025059 | 4.09765e9 |
| 4 | 0.0143369 | 4.08124e9 |

Averaging these values leads to an average hydraulic resistance of 4.08162e9 kg/m4·s with a standard deviation of 0.01584e9 kg/m4·s. This proves that the circuit model still holds when the bioreactors are placed in an array.

The value of $R_2$ for the cell construct is nearly seventeen times larger than that of $R_1$. This seems rather large but still seems feasible. From FIG. 57, it is apparent that the fluid flow through the sides of the central chamber is non-uniform and chaotic. Fluid, like current, wants to travel down the path of least resistance; therefore, fluid would much rather travel along a path of uniform velocity and direction such as in the center of the chamber rather than through the side having its velocity constantly changing. For this reason, the difference in resistance between the two sides of the central chamber is accepted.

Understanding how the fluid is forced through the bioreactor allows for a better design to maximize the flux through the middle of the model while still using diffusion as the method of transport. Features of the model can be changed such as the step height or the diameter of the pores and channels in order to increase the hydraulic resistance of the bioreactor and consequently the central velocity through the test cells. Further models can be created and analyzed with the goal of maximizing the pressure difference between the nodes of the central chamber which will in turn maximize the volume flow through that length. This also offers a better method for comparing two models. Previously, models were compared by looking at simply the hydraulic resistance of the entire bioreactor, but by using this technique, a better comparison can be made as the overall resistance does not convey how the fluid is forced through the model.

Many more models of differing dimensions can be made in order to compare the resistance of the central chamber with that of the current working model in order to see if pertinent relationships develop between changing dimensions and changing resistance. Also, different materials can be placed in the central chamber, resulting in different flow behaviors, such as with materials that is more or less permeable. Further, increasing the number of pores can increase the number of steady bands of flow through the central chamber. This can be useful to change resistances of the resistors representing the cell construct when there is more than one instance of flow with uniform direction and velocity.

Distributed and Lumped Parameter Models for the Characterization of High Throughput Bioreactors The following, along with FIGS. 32-40, describes the development of a general computational approach to model the microfluidics of a multi-chamber, interconnected system, such as those that may be applied to human-on-chip devices. This development includes overcoming several challenges at the level of computational modeling, including addressing the multi-physics nature of the problem that combines free flow in channels with hindered flow in porous media. Fluid dynamics is also coupled with advection-diffusion-reaction equations that model the transport of biomolecules throughout the system and their interaction with living tissues and C constructs. Ultimately, this technology can provide a predictive approach useful for the general organ-on-chip community. To this end, we have developed a lumped parameter approach that allows the analysis of the behavior of multi-unit bioreactor systems with modest computational effort, provided that the behavior of a single unit can be fully characterized.

1 Introduction

Figure 32:
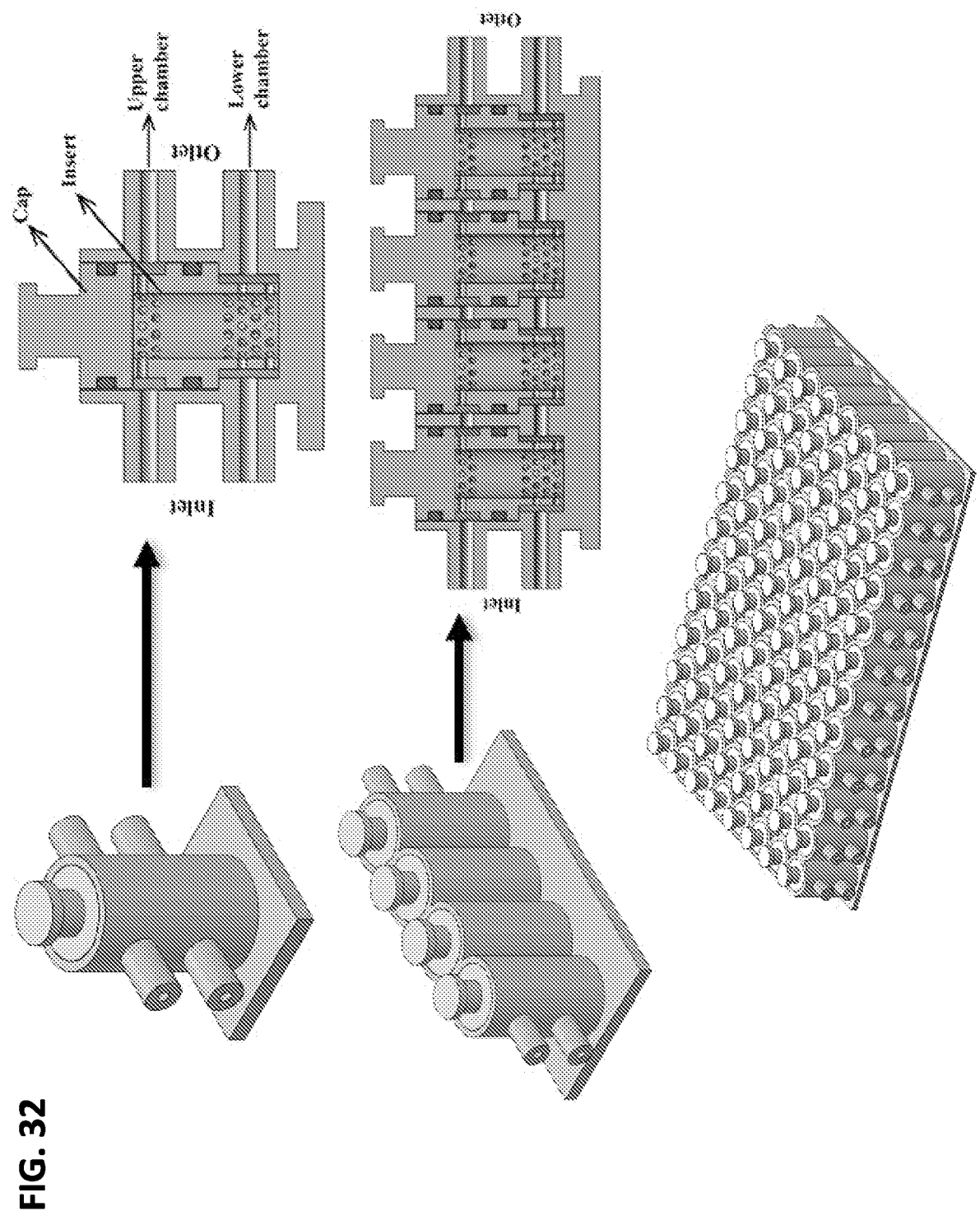
FIG. 32 shows different bioreactor configurations: 1 cell (top left), 1-unit in cross section (top right), 4-units (bottom left) and 96-units. (bottom right).

A number of in vitro approaches have been used over time for high throughput drug screening or toxicology testing. However, most currently available systems are only partial approximations of human biology and their predictive capacity is consequently limited. In fact, such systems are either based on human cell cultures, not capturing the complexity of cell behavior in a three dimensional (3D) environment, or they are based on animal tissues fragments, 3D in nature but only partially biosimilar to human tissues and unable to account for interactions with other organs. To overcome these limitations, next generation bioreactors are being developed to generate multiple human cell-based tissue analogs within the same fluidic system to better recapitulate the complexity and interconnection of human physiology. These efforts aim at creating multi-tissue organ systems (cardiovascular, gastro-intestinal, musculoskeletal, etc.) that ultimately can be joined in an interconnected human-on-chip device capable of providing a veritable representation of the body complex response to diseases and potential drug treatments. The effective development of these devices requires a solid understanding of their interconnected fluidics, to predict the transport of nutrients and waste through the constructs and improve the design accordingly. In this work, we have focused on a specific bioreactor with multiple input/output aimed at generating osteochondral constructs, i.e., a biphasic constructs in which one side is cartilaginous in nature, while the other is osseous. This bioreactor represented in FIG. 32 has been chosen since it comprises both a dual chamber system to host a single biphasic tissue construct with distinct fluidics (FIG. 32, top), and a set of interconnected chambers with common fluidics (FIG. 32, bottom). Starting from this specific bioreactor, we have developed a general approach to model the microfluidics of a multi-chamber, interconnected system that may be applied to human-on-chip devices.

The microphysiological osteochondral bioreactor analyzed in this work is aimed at the study of osteoarthritis (OA), a major pathology of articular joints, affecting over 33% of the population over the age of 65. The hallmark of this disease that affects all tissues in the joint, is the progressive degeneration of cartilage which begins well before clinical symptoms manifest, ultimately requiring joint replacement surgery. The high incidence of this painful and disabling pathology begs for the understanding of the causes and mechanisms of its development, in order to identify reparative drug therapies to arrest or even regenerate the damaged tissues and ultimately avoid surgery. A novel strategy in this respect adopts a tissue engineering approach and the use of bioreactors to generate a high number of identical in vitro constructs that can replicate the pathogenesis of joint diseases for the identification of therapeutic targets and for drug screening. Critical in this respect is the development of a representative model of the interactions between cartilage and other joint tissues and, in particular, with the subchondral bone. In fact, there is growing evidence of the exchange of nutrients, cytokines, and hormones in vivo between bone and cartilage. The osteochondral (OC) unit is then conceived as the main target of OA, to reflect the dynamic cartilage/bone interplay in both health and disease. The medium to high throughput system studied in this work, which we call high-throughput bioreactor (HTB) hereon, is the first of its kind. It hosts in a single chamber a biphasic construct, with separate fluidics for its cartilaginous and osseous components, effectively creating a dual-chamber setup (FIG. 32). In this way, cartilage and bone will be in contact and able to signal to each other, while each is exposed to its ideal culture medium. Furthermore, the HTB allows the generation and culture of a high number of identical OC constructs similar in dimensions to native tissue biopsies. It must be noted that the physiological functions of the examined tissue are primarily load bearing and force transduction, which imply a key role for the extracellular matrix (ECM), also an essential player in the regulation of cell differentiation, physiology and response to insults. Consequently, a bioreactor that accommodates a significant ECM tissue component to recapitulate at least some of the physiological aspects of the osteochondral complex requires a relatively larger volume, in the order of millimeters rather than the hundreds of micrometers more common in microfluidic systems. To generate a construct that mimics tissue physiology, the bioreactor chamber is filled with a cell-laden porous polymeric scaffold. Hence, the larger size and the presence of porous scaffold within the insert makes nutrient perfusion within the device a potential challenge, since to avoid cellular hypoxia and to obtain adequate tissue development, nutrients must travel a longer path to reach the inner regions within the bioreactor. In this context, we use computational fluid dynamics to assess the hydrodynamic properties of the system. Previous works evaluated the fluid mixing and transport of nutrients between chambers in the same unit of a forced perfusion setup, but to our knowledge there are no similar studies about the interaction of fluid and porous constructs in a design with more effective fluidics as the one in FIG. 32.

Furthermore, to achieve a high-throughput drug screening system, single bioreactor dual-chambers (bioreactor unit) have been connected and combined in a multi-unit system, organized in sequential and parallel rows (FIG. 32). In the 96 wells design presented in FIG. 32, individual units are connected only in series, 8 at a time as this design is best suited for drug or toxicological screening; to asses for instance a dose response, each array of 8 units can be subjected to a different concentration of the compound under examination. "In parallel" connection, although possible, has not been envisioned. The constructs in each row are meant as replicates for multiple endpoint testing (e.g., histology, PCR, etc.). A further challenge is then to guarantee that the tissue constructs in the downstream chambers receive the appropriate amount of nutrients from the fluid that has perfused the units upstream. In other words, not only a dual-chamber bioreactor, but also a multi-unit array shall be analyzed.

The specific objective of this work is to develop a methodology to characterize the flow and transport in a HTB by means of a computational modeling approach, combining distributed and lumped parameter models. In particular, we have assessed the degree of perfusion and mixing of nutrients in each region of the device, evaluating the effect of different scaffold types. The computational model was then used to compare two different engineered constructs, a hydrogel (methacrylated gelatin, GelMA) and a porous polymeric scaffold (poly-L-lactate, PLLA). The first one features very small pore size and is solute permeable, the second one shows larger pore size and is impenetrable to fluid and nutrients.

Performing such simulations requires overcoming several challenges at the level of computational modeling. The main one consists of addressing the multi-physics nature of the problem that combines free flow in channels with hindered flow in porous media. Fluid dynamics is then coupled with advection-diffusion-reaction equations that model the transport of biomolecules throughout the system and their interaction with living tissue. Besides these modeling challenges, the complex configuration of the bioreactor poses significant difficulties in building the CAD model and discretizing its parts with a computational mesh suitable for the application of a numerical scheme. These issues can be solved using an in-house-made software that incorporates state-of-the-art efficient algorithms for the approximation of partial differential equations. Although this approach is viable, it entails significant costs in terms of man-hours for the implementation and validation of the new software. For this reason, we have adopted here a commercial platform, ANSYS (ANSYS Inc., Canonsburg, Pa.), which features advanced multi-physics simulation capabilities. Another challenging aspect of this work is then to stretch the limits of the ANSYS platform to address the complex problem at hand. Ultimately, our aim is to provide a predictive approach useful for the general organ-on-chip community. To this end, we have developed a lumped parameter approach that allows us to analyze the behavior of multi-unit bioreactor systems with a modest computational effort, provided that the behavior of a single unit could be fully characterized. If the linearity conditions are satisfied, this computational methodology is independent from the specific osteochondral nature of the biological system being studied. Our approach simply describes a network of interconnected multi-chamber units. Consequently, we believe that our approach can be directly applied to predict the flow and transport of a generic human-on-chip setup, even those comprising multiple physiological systems (e.g., a liver model connected to a kidney model, connected to a bone model, etc.) with single or multi-chamber units.

2 Models and Methods

Exploiting the commercial platform ANSYS (ANSYS Inc., Canonsburg, Pa.), we have developed a CAD model of the bioreactor and we have used it to simulate flow and transport phenomena in the system. The steps to achieve a realistic simulation of the fluid and transport within the bioreactor are detailed below.

2.1 CAD Model

The 3D CAD model of the bioreactor was created using ANSYS ICEM CFD v.15.0 (ANSYS Inc.) CAD modeler. Some bioreactor systems include a row of 4-units connected in series (see FIG. 32). Each unit has the same configuration, specifically designed to grow a construct that combines cartilage and bone, and comprises the following parts: two inlets and two outlets consisting of cylindrical channels, to guarantee the circulation of fluid from the upstream units to the downstream ones. Each inlet/outlet channel is characterized by a length (L) of 5.3 mm and an inner diameter (d) of 1 mm. The perforated cylindrical insert that holds the scaffold in place is 8.5 mm high and 3.75 mm wide. Each bioreactor chamber is sealed by an upper cap and by two O-rings (see FIG. 32). Forthcoming extensions of this study will consider rows of 8 bioreactor units. By aligning 12 parallel lines of these rows, one obtains a plate of 96-units, which is a realistic prototype of high-throughput bioreactor for drug screening.

2.2 Flow

The bioreactor features the combination of free flow for the inlets, outlets, and the outer chambers with porous media flow for the inner culture chamber (insert). In each region, we assume that the flow is incompressible. For momentum balance, our approach employs a general equation that encompasses the nature of both types of flow, and we will switch between them by suitably tuning the problem parameters in each region. This equation has the structure of Brinkman equation for flow in porous media, because it combines viscous terms, such as in Stokes, with friction terms, such as in Darcy. To model free flow, a convective term, which plays a significant role in case of high Reynolds regimes, was added. Static conditions are also assumed. Then, the momentum balance equation reads as follows:

$$\nabla \cdot (\rho \underline{U} \times \underline{U}) - \nabla \cdot (\mu(\nabla \underline{U} + (\nabla \underline{U})^T)) = -\frac{\mu}{K_{perm}} \underline{U} - \nabla p \qquad (8)$$

$$\forall x \in \Omega_{c\_up} \cup \Omega_{c\_down} \cup \Omega_{scaffold}$$

where $\underline{U}$ denotes the velocity vector field ($\underline{U}_f$ and $\underline{U}_p$ denote the restriction of the velocity field to the free fluid and porous medium, respectively), p the hydrostatic pressure, $\rho$ e $\mu$ are the fluid viscosity and density respectively, and $K_{perm}$ the hydraulic conductivity of the porous medium (for the free flow regions we set $K_{perm} \to \infty$). For the partition of the bioreactor into sub-regions, we refer to FIG. 33. We assume that the culture medium that perfuses the bioreactor is comparable to water ($\rho$=999.97 kg/m³ $\mu$=0.001 Pa·s) since the dissolved nutrients and other chemical species are relatively dilute.

For the definition of boundary conditions, we partition the bioreactor surface as illustrated in FIG. 33. At the bioreactor inlet, ($\Gamma_{c\_up,in} e \Gamma_{c\_down,in}$) a given flow rate is applied through the enforcement of a flat velocity profile on the inflow sections; a no-slip condition is adopted on the surfaces that separate the free fluid and the porous medium from the bioreactor walls ($\Gamma_{c\_up}, \Gamma_{c_{down}} e \Gamma_{scaffold}$), which have been assumed to be rigid walls. At the outlet, ($\Gamma_{c\_up,out} e \Gamma_{c\_down,out}$) we have set a uniform normal stress field equal to the atmospheric pressure, namely $\sigma_f n=0$, where $\sigma_f = \nabla \cdot (\mu(\nabla \underline{U} + (\nabla \underline{U})^T)) - \nabla p$ is the Cauchy stress in the fluid. Given the previous modeling choices, the flow problem becomes $$\begin{aligned}
\nabla \cdot \underline{U} &= 0 & \forall x &\in \Omega_{c\_up} \cup \Omega_{c\_down} \cup \Omega_{scaffold} & (9)\\
\nabla \cdot (\rho \underline{U} \times \underline{U}) - \nabla \cdot (\mu(\nabla \underline{U} + (\nabla \underline{U})^T)) &= -\frac{\mu}{K_{perm}} \underline{U} - \nabla p & \forall x &\in \Omega_{c\_up} \cup \Omega_{c\_down} \cup \Omega_{scaffold} \\
Q(r) &= \overline{Q} & \forall x &\in \Gamma_{c\_up,in} \cup \Gamma_{c\_down,in} \\
P &= 0 & \forall x &\in \Gamma_{c\_up,out} \cup \Gamma_{c\_down,out} \\
\underline{U} &= 0 & \forall x &\in \Gamma_{c\_up} \cup \Gamma_{c\_down} \cup \Gamma_{scaffold} \\
\underline{U}_f &= \underline{U}_s & \forall x &\in \Gamma_{fluid-porous} \\
\sigma_f \cdot n &= \sigma_s \cdot n & \forall x &\in \Gamma_{fluid-porous}
\end{aligned}$$

2.3 Mass Transport

An important part of this study consists of modeling the transport of bio-molecules dissolved in the culture media that perfuse the bioreactor. In particular, we focus on oxygen, fundamental to guarantee cell survival. However, the model is general and has been used to describe the transport of glucose and proteins, as it will be reported in forthcoming works. Since all solutes are diluted, they are modeled as passively transported by the culture media. Their governing equations have been formulated in terms of volumetric concentrations measured in [mg/ml]. The symbol C denotes the solute concentration, D the diffusion coefficient for the specific biomolecule and the subscripts f and s indicate the fluid and the porous medium (scaffold), respectively. Therefore the equation describing the biomolecules' transport in the fluid phase is:

$$\nabla \cdot (-D_f \nabla C_f + \underline{U} C_f) = 0 \quad \forall x \in \Omega_{c\_up} \cup \Omega_{c\_down} \quad (10)$$

For the porous medium, namely the scaffold region, we assume that fluid and solid phases coexist. We denote with $C_{s,s}$ and $C_{a,f}$ the volumetric concentration of biomolecules in the solid and in the fluid phase of the scaffold, respectively. Denoting with $\gamma$ the porosity of the scaffold (complement to unity of the solid phase, i.e. for the free flow regions we set $\gamma = 1$), the volumetric concentration of biomolecules in the porous medium is given by the following weighted average $C_s = \gamma C_{s,f} + (1-\gamma) C_{s,s}$. Then, following the theory of mixtures, the governing equations for biomolecules concentration in the porous medium read as follows:

$$\nabla \cdot (-D_{s,s} \nabla (1-\gamma) C_{s,s} + (1-\gamma) \underline{U} C_{s,s}) + (1-\gamma) S + \tau IAD(C_{s,s} - C_{s,f}) = 0;$$

$$\nabla \cdot (-D_{s,f} \nabla \gamma C_{s,f} + \underline{U} \gamma C_{s,f}) + \gamma S + \tau IAD(C_{s,f} - C_{s,s}) = 0 \forall x \in \Omega_{scaffold}. \quad (11)$$

This model assumes that both the fluid and the solid phases in the porous medium are permeable to biomolecules. The mass transfer coefficient from the fluid to the solid phase in the porous medium is $\tau$, while IAD is the interface area density of the surface separating the two phases. As a result, the term $\tau IAD(C_{s,s} - C_{s,f})$ represents the flux exchanged between the two phases of the porous medium. The symbol S denotes the source term representing the consumption of nutrients by living cells disseminated into the scaffold. For this reason, it is usually a function (linear or nonlinear) of the nutrient concentration. We will discuss the constitutive models for the parameters in S,$\tau$,IAD in the next section.

At the inlet boundaries ($\Gamma_{c\_up,in} e \Gamma_{c\_down,in}$) a known concentration has been imposed, using independent values on each inlet section. A homogeneous Neumann condition $\nabla C_f \cdot n = 0$ has been adopted on the bioreactor wall and outlets ($\Gamma_{c\_up}, \Gamma_{c\_down}, \Gamma_{c\_up,out} e \Gamma_{c\_down,out}$). In fact, the wall is considered impermeable to nourishments and their flux in the direction normal to the outlets is assumed equal to zero. Moreover, conservation of concentrations $C_f = C_s$ and of biomolecules flux $-D_f \nabla \cdot C_f n = -D_s \nabla \cdot C_s n$ have been applied at the interface between fluid and porous media ($\Gamma_{fluid-porous}$). As a result, the concentration of oxygen is determined by the following problem:

| | |
|---|---|
| $\nabla \cdot (-D_{s,s} \nabla (1-\gamma) C_{s,s} + (1-\gamma) \underline{U} C_{s,s}) + (1-\gamma) S + \tau IAD(C_{s,s} - C_{s,f}) = 0$ | $\forall x \in \Omega_{scaffold}$ |
| $\nabla \cdot (-D_{s,f} \nabla \gamma C_{s,f} + \underline{U} \gamma C_{s,f}) + \gamma S + \tau IAD(C_{s,f} - C_{s,s}) = 0$ | |
| $\nabla \cdot (-D_f \nabla C_f + \underline{U} C_f) = 0$ | $\forall x \in \Omega_{c\_up} \cup \Omega_{c\_down}$ |
| $C_f = \overline{C}_1$ | $\forall x \in \Gamma_{c\_up,in}$ |
| $C_f = \overline{C}_2$ | $\forall x \in \Gamma \Gamma_{c\_down,in}$ |
| $\nabla C_f \cdot n = 0$ | $\forall x \in \Gamma_{c\_up,out} \cup \Gamma_{c\_down,out}$ |
| $\nabla C_f \cdot n = 0$ | $\forall x \in \Gamma_{c\_up} \cup \Gamma_{c\_down}$ |
| $C_f = \gamma C_{s,f} + (1-\gamma) C_{s,s}$ | $\forall x \in \Gamma_{fluid-porous}$ |
| $-\gamma D_f \nabla C_f \cdot n = -D_s \nabla (\gamma C_{s,f}) \cdot n$ | $\forall x \in \Gamma_{fluid-porous}$ |
| $-(1-\gamma) D_f \nabla C_f \cdot n = -D_s \nabla ((1-\gamma) C_{s,s}) \cdot n$ | $\forall x \in \Gamma_{fluid-porous}$ |

2.4 Model Parameters and Constitutive Laws

2.4.1 Model Parameters for the Flow Model

First, the characteristic Reynolds number of the flow in the bioreactor was determined from the following definition, $$Re = \frac{vD\rho}{\mu} = \frac{4}{\pi D} \frac{\rho v \pi D^2}{4 \mu} = \frac{4}{\pi D} \frac{\rho \overline{Q}}{\mu} \quad (13)$$

where D is the inlet diameter of 1 mm, $\rho = 999{,}97$ Kg/m$^3$ and $\mu = 0{,}001$. Pa·s are the fluid density and dynamic viscosity, respectively, $\overline{Q}$ is the inlet flow rate into each chamber, equal to 1 ml/day. A Re<<0.01, was found thus confirming that the assumption of laminar flow is accurately verified. As a consequence, the inertial (and nonlinear) term in the momentum equation, namely $\rho \underline{U} \times \underline{U}$, can be neglected and the flow model turns out to be a set of linear equations. This will be the key property for the later derivation of a surrogate of the flow model, which is only based on algebraic equations consequently featuring a negligible computational cost.

Another parameter, essential to determining the flow in the porous medium is the (intrinsic) permeability $K_{perm}$, that is determined by the microscopic structure of the scaffold, quantified by the porosity ($\gamma$), the tortuosity, etc. In the case of materials featuring an anisotropic structure, permeability is a tensor quantity. Here, since the scaffolds under consideration are isotropic, it becomes a scalar parameter. In what follows, we will consider two types of scaffolds, one made out of methacrylated gelatin (GelMA) and the other consisting of a poly-L-lactate (PLLA) foam. The porosity and permeability of the latter have been estimated via Boyle's pycnometer and scanning electron microscopy (SEM) analysis. Data for GelMA are scarce in literature. However, for tissue engineering it is used as a surrogate material to mimic the extracellular matrix of cartilage; hence, we initialized the model for the bioreactor configuration using data that have been previously measured for native cartilage. In both cases, the values for porosity and permeability are reported in Table 8 below.

TABLE 8

Porosity and permeability values
used for GelMA and PLLA scaffolds

| | GelMA scaffold | PLLA scaffold |
|---|---|---|
| Porosity | 0.8 | 0.93 |
| Permeability [m$^2$] | 1e−16 | 3.23384e−09 |

2.4.2 Model Parameters and Constitutive Laws for Mass Transport

Inlet concentrations for oxygen are 3.15 e-3 [mg/ml] and 7.2 e-3 [mg/ml] for the upper and lower chamber, respectively. We observe that the oxygen supply of the upper chamber falls within the range of hypoxic conditions, compatible with the biological need of the chondral tissue, while the lower chamber, where bone is developed, is kept under normoxic conditions. These different environments are aimed at supporting stem cell differentiation into a chondral and osseous phenotype, respectively. The diffusion coefficient was obtained from previously published studies.

Figure 34:
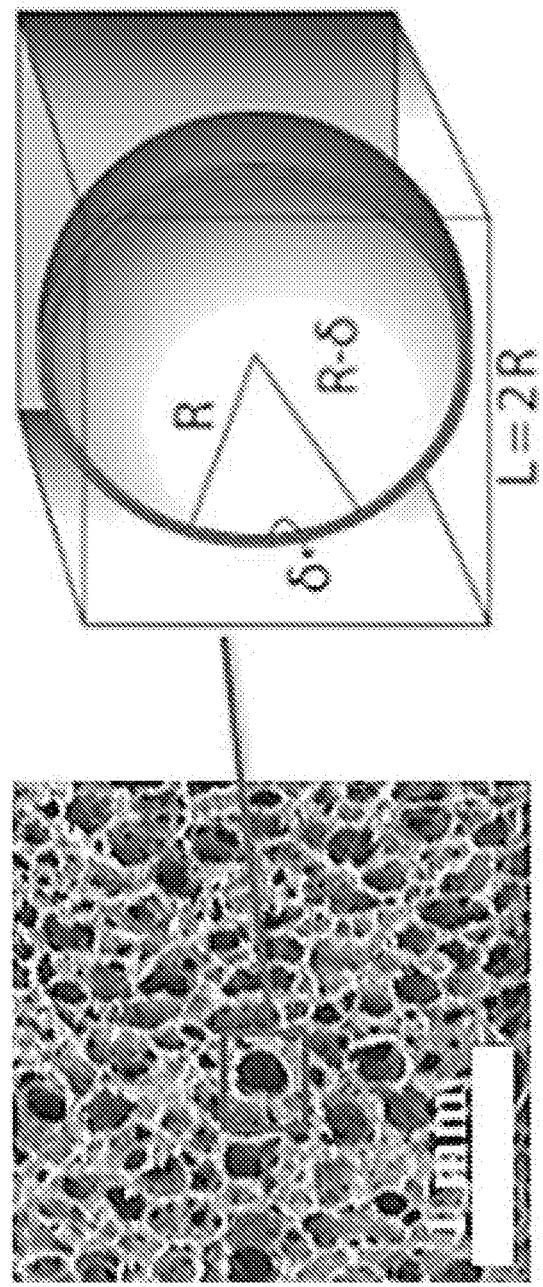
FIG. 34 shows a representative SEM micrograph of the PLLA scaffold and microscopic model of the scaffold pores for the quantification of the exchange between fluid and solid constituents of the porous matrix.

For the exchange of biomolecules between fluid and solid phases within the scaffold, the coefficients $\tau$,IAD must be calculated. To this purpose, we model the porous medium as a periodic structure whose unit can be idealized as a cube containing a hollow sphere, namely the pore, as illustrated in FIG. 34.

Although this configuration is incompatible with the flow through the pore, as it is completely closed, it is adequate for modeling mass transfer between the solid and the fluid phases of the porous medium. According to this model, we estimate the value of the interface area density (IAD), which only depends on the configuration of the unit. Let $S_{a\_a}=4\pi R^2$ and $S_{i\_s}=4\pi(R-\delta)^2$ be the external and internal pore surface, respectively, and let $V_c$ be the total volume of the unit. Then the interface area density is defined as:

$$IAD = \frac{S_{e\_s} + S_{i\_s}}{V_c} \quad (14)$$

To estimate the mass transfer coefficient, we assume that at the pore scale mass transfer is dominated by diffusion in the solid phase. As a consequence, the Sherwood number magnitude turns out to be in the range of unity. Exploiting this assumption, we have $$1 = Sh = \frac{\tau d}{D_{s,s}} \quad (15)$$

where $\tau$ is the mass transfer coefficient and d is the pore diameter. As a result, we obtain, $$\tau = \frac{D_{s,s}}{d} \quad (16)$$

We observed that GelMA and PLLA have different behaviors with respect to mass transfer and interface area density. GelMA scaffold has homogeneous properties, namely the pore radius is uniform everywhere and equal to R=9.77205 e-6 with a thickness $\delta$=10% R. The GelMA matrix is permeable to solutes, as shown by the positive diffusion coefficients $D_{s,s}$ reported in Table 9 below. The PLLA scaffold is substantially different because it is impermeable to solutes. As a result, the mass transfer coefficient is necessarily null. Since the exchange between solid and fluid phases in the porous medium is modeled by terms $\tau$IAD $(C_{a,c}-C_{a,f})$, we notice that the interface area density does not affect the model.

TABLE 9

Oxygen parameters adopted for GelMA and PLLA scaffolds

| | GelMA | PLLA |
|---|---|---|
| $D_f = D_{s,f}$ | $2.1 \times 10^{-9}$ [m$^2$/s] | $2.1 \times 10^{-9}$ [m$^2$/s] |
| $D_{n,s}$ | $4.5 \times 10^{-10}$ [m$^2$/s] | 0 |
| $\tau$ | 0.230248e-5[211] [m s$^\wedge$-1] | 0 |
| IAD | 2.9094e5 [m$^\wedge$-1] | 3.8924e4 |
| $v_{max}$ | 1.15 10$^{-17}$ [mol/cell s] | 1.15 10$^{17}$ [mol/cell s] |
| $N_v$ | 1.12 10$^6$ [cell/ml] | 1.12 10$^6$ [cell/ml] |
| $\overline{C}_s$ | 168.98 10$^{-9}$ [mol/cl] | 168.98 10$^{-9}$ [mol/cl] |

In order to complete the mass transport model, we introduced the term S, to account for both catabolite production and metabolite consumption in cell metabolism. Given the importance of maintaining cell viability by ensuring sufficient nutrients supply, we focus in particular on metabolite consumption, for which studying transport of oxygen is ideal. Cells are assumed to be confined in the porous scaffold and consumption of nutrients, $S(C_s)$, is expected to be proportional to their availability, namely $S(C_s)=S(\gamma C_{s,f}+(1-\gamma)C_{s,s})$. Different models can be adopted for this function, either linear or nonlinear. In the former case we set $S(C_g)=rC_s$, where $\tau$ is a constant parameter determined according to the following balance law:

$$r \cdot \overline{C} = V_{max} \cdot N_v \quad (17)$$

where C is a reference concentration for each solute, measured in [mol/ml], $V_{max}$ the maximal consumption rate for the considered nutrient and for a specific cell phenotype, quantified in [mol/cell s], and $N_v$ is the average volumetric cell density in the scaffold, measured in [cells/ml]. The main limitation of this model is that it does not guarantee any upper bound for nutrient consumption rate. The more nutrients are available, the more they are metabolized. This approach can be improved using a Michaelis-Menten description of cell metabolism, which introduces saturation of the consumption rate, according to the following function:

$$r(C_s) = \frac{V_{max} C_s}{K_m + C_s} \quad (18)$$

where $K_m$ is the Michaelis-Menten constant, equal to the concentration at which the consumption rate reaches 50% of the maximal value. As a result, the consumption term turns out to be a nonlinear function, namely $$S(C_s)=r(C_s)C_s \quad (19)$$

We observe that for small nutrient concentrations the linear and the Michaelis-Menten models behave similarly, whereas the latter provides a better estimate of metabolic consumption in case of abundance of nutrients.

2.5 Computational Solvers

The commercial code ANSYS CFX v.13.0 was used to carry out the fluid dynamic and mass transport simulations. The spatial discretization consists of a cell based finite volume method. From the computational standpoint, the main challenge of this study consists in solving a fluid-porous interaction problem that involves coupled flow and mass transport. A fully coupled strategy has been adopted, namely all the equations are solved simultaneously through a monolithic linear system that embraces all the degrees of freedom.

More precisely, the Laplace operator in the fluid momentum and oxygen transport equations is approximated by a centered scheme, while the convective terms have been discretized by means of an upwind method. The convective term in the Navier-Stokes equations is linearized by Picard iterations (equivalent to a fictitious time stepping method with semi-implicit treatment of $\nabla \cdot (\rho \underline{U} \times \underline{U})$) ("ANSYS CFX-Solver Theory Guide", ANSYS Inc., 2010). The pressure variable in the Navier-Stokes equations is evaluated at the same nodes of the velocity field.

The system is then solved using an algebraic multigrid method exploiting incomplete LU factorization as smoother. Numerical simulations have been performed on parallel CPUs using a quad-socket 12-Core AMD Magny Cours CPU, 128 GB RAM at University of Pittsburgh. Convergence criteria were set to $10^{-6}$ for the normalized residuals of the global linear system of equations.

To ease the convergence of the algebraic solver, it turned out to be extremely helpful to neglect the contribution of streamline diffusion in the mass transport model, accounting only for the cross-wind component of the diffusion operator. From the modeling standpoint, this approximation is justified since the Péclet number characterizing mass transport in the ducts and in the scaffold of the bioreactor is larger than unity. More precisely, we define the Péclet number as follows $$Pe = \frac{a\overline{U}}{D} \tag{20}$$

where $\alpha$ is the characteristic length of diffusion, $\overline{U}$ is the characteristic fluid velocity and is the diffusion coefficient of the nutrient in the fluid (water). The Peclet number has been calculated for two sets of parameters, the first one identifying flow and mass transport in the pores of the insert ($\alpha$=9.77205 e-6 m, $\overline{U}$=1.546e-3 m/s, D=2.9e-9 m$^2$/s) and the second one the flow in the chambers that will hold the scaffold ($\alpha$=5e-4 [m], $\overline{U}$=1.473e-5 [m/s], D=2.9e-9 [m$^2$/s]). For the insert we obtained Pe=2.5, while for the chambers $p_e$=5.2.

Domain discretization is a crucial phase in the computational model set up to ensure an accurate description of the investigated phenomena as well as reasonable computational time and costs. The geometrical features of the bioreactors span from 8.5 mm (height of the scaffold), to 1 mm (inlet/outlet channel inner diameter), to 0.25 mm (radius of the pores). The final mesh consists of 735658 and 550226 tetrahedral elements for the GelMA and the PLLA case, respectively, with a minimum dimension of the elements of 0.1 mm and a maximum of 0.25 mm. This discretization is suitable for the fluid dynamics model, because, as previously stated, the Reynold's number results smaller than 0.01, and consequently the boundary layers can be considered fully developed. The fluid dynamics simulations in single array are performed with moderate computational effort (about 7 minutes on CPUs using a quad-socket 12-Core AMD Magny Cours CPU, 128 GB RAM). A numerical test that uses a coarser mesh consisting of 443740 and 242236 elements, respectively, confirms that the results obtained with the finer discretization are insensitive to the mesh size.

3 Lumped Parameter Models of HTB

Although in-silico analysis is rightfully considered a cost efficient approach with respect to experimental investigation, section 2.3 illustrates that the development of a computational model of the bioreactor is a challenging task, because of the significant amount of work-hours required to define a detailed CAD model and the considerable computational efforts involved with the definition of a computational mesh and with the solution of the discrete equations.

When using numerical tools in the design or optimization of the bioreactor configuration and working conditions, it is essential to minimize the cost of running simulations for different sets of design parameters. The scientific computing community is well aware of this critical aspect of the approach and has recently made great progress in developing strategies to synthesize surrogate models that replace the brute force simulation approach with much less computational costs. We have mentioned a list of a few examples related to bioengineering, among many others. Surrogate or reduced models are based on much simpler mathematical operators than partial differential equations. For steady problems, they may consist of algebraic equations, or ordinary differential equations to capture time dependent phenomena. Such models are often called lumped parameter models, because they synthesize into a small number of coefficients the behavior of spatially dependent functions, solutions of partial differential equations, a.k.a. distributed parameter models.

An object of this section is to derive a set of lumped parameter models describing flow and mass transport in the bioreactor fulfilling two objectives:

1. To determine the change of quantitative outputs when the input data are varied, for a fixed single or multi-chamber configuration,
2. To determine the change of quantitative outputs when the number of chambers in the array is varied.

3.1 Lumped Parameter Model for a Fixed HTB Configuration

We aim to develop an input-output relation between parameters of the model and observed quantities of interest. Because of the linearity of the flow model, motivated by low Reynolds numbers, this relation is a linear operator that can be characterized by a limited number of simulations. The number of required simulations depends on the dimension of the input/output parameter space.

To illustrate the derivation of a lumped parameter model, we consider an example that will be later used for the bioreactor design. In particular, we analyze the flow split at the outlet of the bioreactor chambers for prescribed values of the inlet flow rates. Let us consider the velocity fields $\underline{U}_i$, i=1,2 defined by fixing unit flow rates at each inlet of the bioreactor, $$-\nabla \cdot (\mu(\nabla \underline{U}_i + (\nabla \underline{U}_i)^T)) = -\frac{\mu}{K_{perm}}\underline{U}_i - \nabla p_i \tag{21}$$

$$\forall x \in \Omega_{c\_up} \cup \Omega_{c\_down} \cup \Omega_{scaffold}$$

$$\nabla \cdot \underline{U}_i = 0 \qquad \forall x \in \Omega_{c\_up} \cup \Omega_{c\_down} \cup \Omega_{scaffold}$$

$$\underline{U}_i = 1 \qquad \forall x \in \Gamma_{in,i}, i = 1, 2$$

$$\sigma(\underline{U}, p) \cdot n = 0 \quad \forall x \in \Gamma_{out,i}, i = 1, 2$$

Since the flow model is linear, the velocity and pressure fields $\underline{U}$,p corresponding to any combination of the inlet flow rates, denoted as $Q_{in1}$ and $U_{in2}$ respectively, can be represented as a linear combination of solutions $\underline{U}_i$,$p_i$ $$\underline{U} = \frac{Q_{in1}}{A_1}\underline{U}_1 + \frac{Q_{in2}}{A_2}\underline{U}_2; \; p = \frac{Q_{in1}}{A_1}p_1 + \frac{Q_{in2}}{A_2}p_2 \tag{22}$$

Since we are interested in the quantification of the outflow rates, we calculate $$Q_{out,i} = \int_{\Gamma_{out,i}} \underline{U} \cdot \underline{n}dx = \tag{23}$$

$$Q_{in,1}\overbrace{\int_{\Gamma_{out,i}} \underline{U}_1 \cdot \underline{n}dx}^{m_{i,1}} + Q_{in,2}\overbrace{\int_{\Gamma_{out,i}} \underline{U}_2 \cdot \underline{n}dx}^{m_{i,2}} = Q_{in,1} \cdot m_{i,1} + Q_{in,2} \cdot m_{i,2}$$

As a result, we have identified the following input-output algebraic relation between inlet and outlet flow rates $$\begin{vmatrix} Q_{out,1} \\ Q_{out,2} \end{vmatrix} = \begin{vmatrix} m_{1,1} & m_{1,2} \\ m_{2,1} & m_{2,2} \end{vmatrix} \cdot \begin{vmatrix} Q_{in,1} \\ Q_{in,2} \end{vmatrix} \; i.e. \; \begin{vmatrix} Q_{out,1} \\ Q_{out,2} \end{vmatrix} = M \begin{vmatrix} Q_{in,1} \\ Q_{in,2} \end{vmatrix}, \tag{24}$$

$$M = \begin{vmatrix} m_{1,1} & m_{1,2} \\ m_{2,1} & m_{2,2} \end{vmatrix}$$

that represents the lumped parameter model we were looking for. We note that the operator (matrix) M depends on the bioreactor geometric design.

This approach can be extended to the mass transport problem, provided that the model adopted for consumption of nutrients is linear, namely $S(C_s) = \gamma C_s$. In this case, we denote with $d_i$ the solution of equation obtained setting $\overline{C}_i = C_{in,1} = 1$ and $\overline{C}_{j \neq 1} = C_{in, \neq j} = 0$. Then, any solution $C_f$ of the mass transport problem can be expressed as $$C_f = C_{in,1} d_1 + C_{in,2} d_2 \quad (25)$$

Let $C_{out,1}, C_{out,2}$ be the nutrient concentration on the upper and lower outlets respectively and for simplicity of notation let us define $$d_{i,1} = d_i|_{\Gamma_{out,up}}, d_{i,2} = d_i|_{\Gamma_{out,down}} \quad (26)$$

Then, because of the linearity of the mass transport model we obtain $$C_{out,i} = C_{in,1} \cdot d_{1,1} + C_{in,2} \cdot d_{2,1} \quad (27)$$

that can be translated in the following vector form, $$\underline{C_{out}} = D \cdot \underline{C_{in}}; \quad \underline{C_{out}} = \begin{vmatrix} C_{out,1} \\ C_{out,2} \end{vmatrix}; \quad \underline{C_{in}} = \begin{vmatrix} C_{in,1} \\ C_{in,2} \end{vmatrix} e \quad (28)$$

$$D = \begin{vmatrix} d_{1,1} & d_{1,2} \\ d_{2,1} & d_{2,2} \end{vmatrix}$$

3.2 Lumped Parameter Model for Variable Bioreactor Configurations

Here we focus on the problem of determining a lumped parameter model for a sequence of bioreactor units, when the solution for 1-unit is known. From the methodological standpoint, this problem is more challenging than the one of characterizing the lumped parameter model for one bioreactor unit, because partial differential equations are not linear with respect to the configuration of the domain. In other words, the solution of an n-unit bioreactor is not the superposition of n solutions of a single unit configuration.

Figure 35:
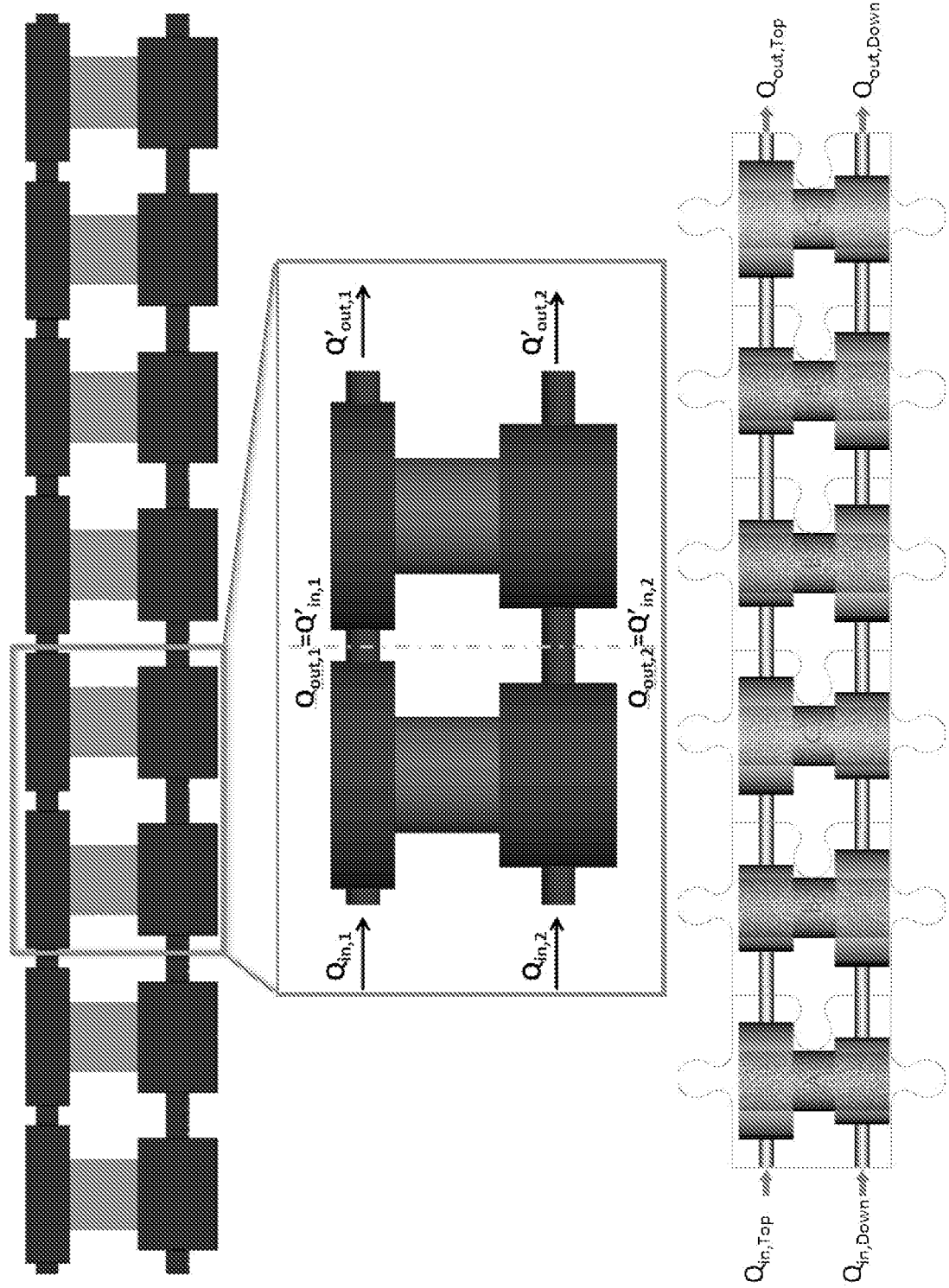
FIG. 35 shows distribute vs lumped parameter models. Top: A 8-unit bioreactor configuration, showing details of a 2-unit example used for the development of the lumped parameter model (top panels). Bottom: A sketch of a multi-unit bioreactor configuration with heterogeneous unit design in a generic sequence of units, where different unit designs are denoted with letters A, B, C.

Another strategy for determining a lumped parameter model of a multi-unit configuration emerges observing that units are combined in sequence (see FIG. 35). Consequently, we conjecture that the behavior of the n-unit bioreactor is the composition of n-unit models. As an example, for a sequence of two units we posit that the input/output relation for flow rates is $$\begin{vmatrix} Q'_{out_2} \\ Q'_{out_1} \end{vmatrix} = \tilde{M} \begin{vmatrix} Q_{in_2} \\ Q_{in_1} \end{vmatrix}; \begin{vmatrix} Q'_{out_2} \\ Q'_{out_1} \end{vmatrix} = \tilde{M}_1 \begin{vmatrix} Q'_{in_2} \\ Q'_{in_1} \end{vmatrix}; \begin{vmatrix} Q'_{in_2} \\ Q'_{in_1} \end{vmatrix} = \tilde{M}_2 \begin{vmatrix} Q_{in_2} \\ Q_{in_1} \end{vmatrix} \quad (29)$$

Owing to the similar design of the upper and lower chambers, the resistance to flow of the fluid entering from the upper and lower inlets is comparable. As a result, the following property is valid at any junction between two adjacent bioreactor units, $$\sigma(\underline{U}, p) \cdot n|_{\Gamma_1} = \sigma(\underline{U}, p) \cdot n|_{\Gamma_2} \quad (30)$$

It shows that equal normal stresses are applied at the intermediate section of a 2-unit bioreactor. Since these are the boundary conditions applied at the outlet of our model for an individual unit it means that any unit in a row functions as an individual one. As a result, we conclude that $$\tilde{M}_1 \cong M; \tilde{M}_2 = M \quad (31)$$

and consequently $$\begin{vmatrix} Q'_{out_2} \\ Q'_{out_1} \end{vmatrix} = M \cdot \begin{vmatrix} Q'_{in_2} \\ Q'_{in_1} \end{vmatrix} = M \cdot M \begin{vmatrix} Q_{in_2} \\ Q_{in_1} \end{vmatrix} = M^2 \begin{vmatrix} Q_{in_2} \\ Q_{in_1} \end{vmatrix} \quad (32)$$

This example can be easily generalized to the case of a row of n-units. More precisely, we infer that the lumped parameter model for an n-unit bioreactor, denoted by $M_n$, the multiplicative composition of n single unit models, namely $$M_n = M^n \quad (33)$$

where the latter expression denotes the n-th power of the operator M.

This approach can be applied to flow as well as to mass transport. In this way, the lumped parameter models M,D, derived in section 3.1 for single unit configurations, can be extended to multi-unit configurations made of units combined in a row. Using direct numerical simulations of multi-cell configurations, we will demonstrate in the next sections the good accuracy of these reduced models.

We finally observe that the model composition rule is also applicable in the case of combination of different unit designs (schematized in FIG. 35 with letters A, B, C). In particular, the input/output relation (Y=M·X) for a row of 3-units of generic type A, B, C of which we know the individual lumped parameter models, $M_A$, $M_B$, $M_C$ respectively, is given by $M = M_A \cdot M_B \cdot M_C$. Following the ambitious vision of building a human-on-chip model, any pattern of bioreactors organized in a row can be characterized using this approach, provided that the properties of each individual unit are known.

4 Numerical Simulations

4.1 Numerical Simulation of Flow

In this study, simulations of flow are performed to compare flow patterns in the GelMA and PLLA scaffold when inlet flow rates are varied. More precisely, the following different flow pairs were simulated: (a) 1 and 1, (b) 1 and 2 and (c) 10 and 10 ml/day for the upper and lower inlet, respectively.

Figure 36:
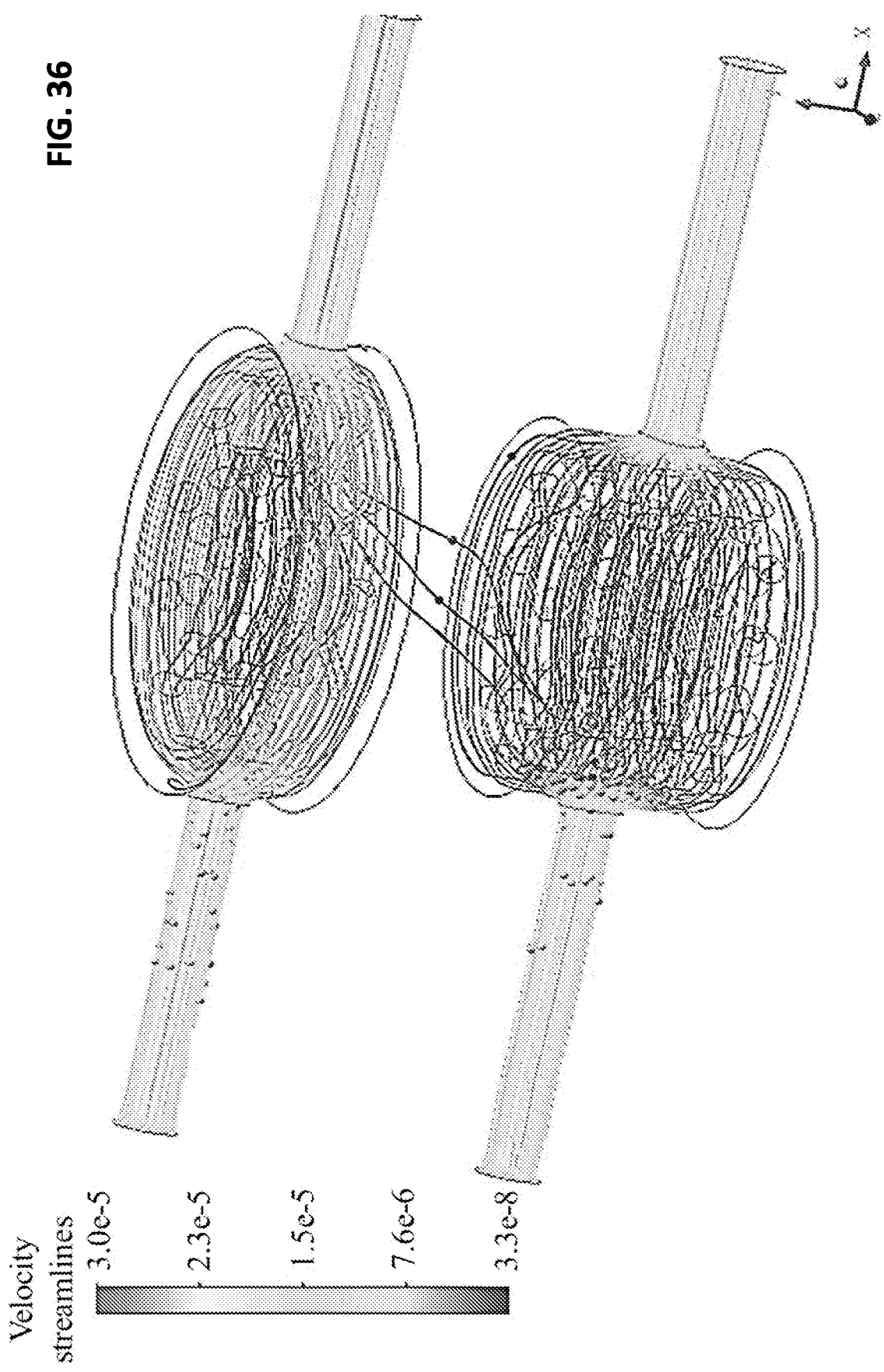
FIG. 36 shows streamlines in the 1-unit model with the GelMA scaffold. For the sake of brevity, the results of the 4-units array are not reported since they are the qualitatively equivalent to the single unit configuration.

We observe that for all the configurations, the fluid is driven by the pressure gradient to move toward the upper chamber (FIG. 36). The flow split obtained by applying the different flow pairs are reported in Tables 10 and 11 below for the GelMA and PLLA case, respectively. The comparison of the outlet flow rates for the two scaffolds highlighted opposite outcomes in terms of flow mixing. Indeed, while not significant flow mixing was found for the GelMA scaffold, a significant mixing occurs in the PLLA case. As expected, the maximum mixing (that is 42.9%) occurs with different input fluid flow rates (1 and 2 ml/day at the upper and lower inlet, respectively).

TABLE 10

Results obtained by simulating different flow split in the one unit model with the GelMA and PLLA scaffold.

| | Inlet | | GelMA | | PLLA | |
|---|---|---|---|---|---|---|
| | $Q_{in,top}$ [Kg/s] | $Q_{in,down}$ [Kg/s] | $Q_{out,top}$ [Kg/s] | $Q_{out,down}$ [Kg/s] | $Q_{out,top}$ [Kg/s] | $Q_{out,down}$ [Kg/s] |
| a) | 1 | 1 | 1 | 1 | 1.032 | 0.968 |
| b) | 1 | 2 | 1 | 2 | 1.429 | 1.571 |
| c) | 10 | 10 | 10 | 10 | 10.32 | 9.68 |

TABLE 11

Percentage of oxygen consumption for the GelMA and PLLA scaffold

| | GelMA | PLLA |
|---|---|---|
| Upper chamber | 0.93% | 4.9% |
| Lower Chamber | 1.8% | 8.14% |

4.2 Numerical Simulation of Transport

Simulations of oxygen transport were performed to compare mass transfer in the GelMA and PLLA scaffolds.

Concentrations equal to 3.15 and 7.2 µg/l were applied at the upper and lower inlet, respectively. As in the previous case, the following flow pairs were simulated: (a) 1 and 1, (b) 1 and 2 and (c) 10 and 10 ml/day at the upper and lower inlet. Two configurations of the bioreactor were considered, namely 1-unit and a 4-unit array. The results of 1-unit model are reported in FIGS. 37A-37C and FIGS. 38A-38C for the GelMA and PLLA scaffold, respectively. The analysis of the mass transport simulations obtained for the GelMA and the PLLA scaffolds allows us to draw general considerations, which are valid for both single and 4-unit arrays.

Figures 37A, 37B, 37C:
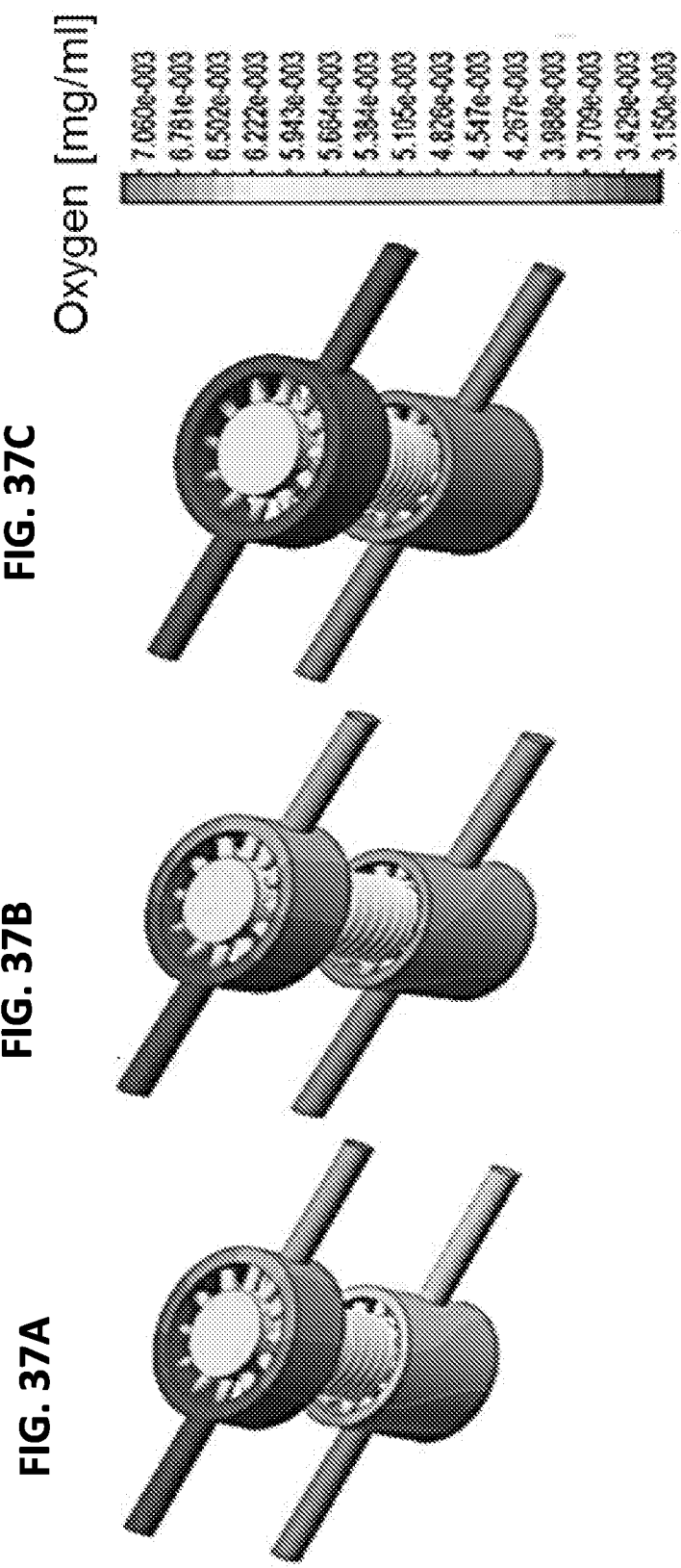
FIGS. 37A-37C show oxygen concentration with GelMA scaffold. From left to right, flow pair of 1-1 [ml/day], 1-2 [ml/day], 10-10 [ml/day].
Figure 38A:
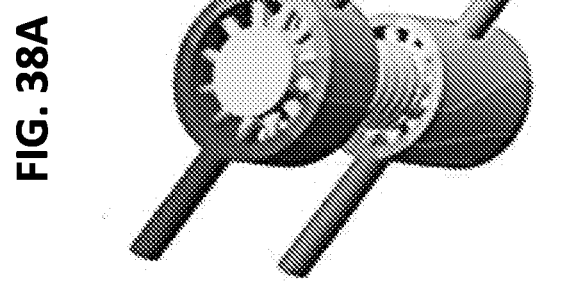
FIGS. 38A-38C show oxygen concentration with PLLA scaffold. From left to right, flow pair\of 1 [ml/day], 1-2 [ml/day], 10-10 [ml/day].
Figure 38B:
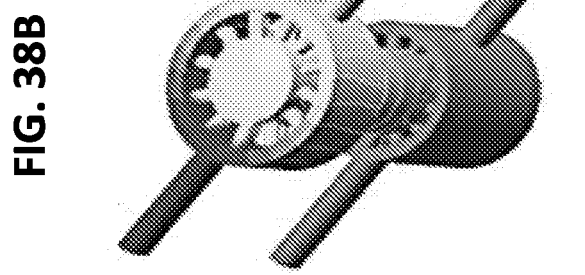
Figure 38C:
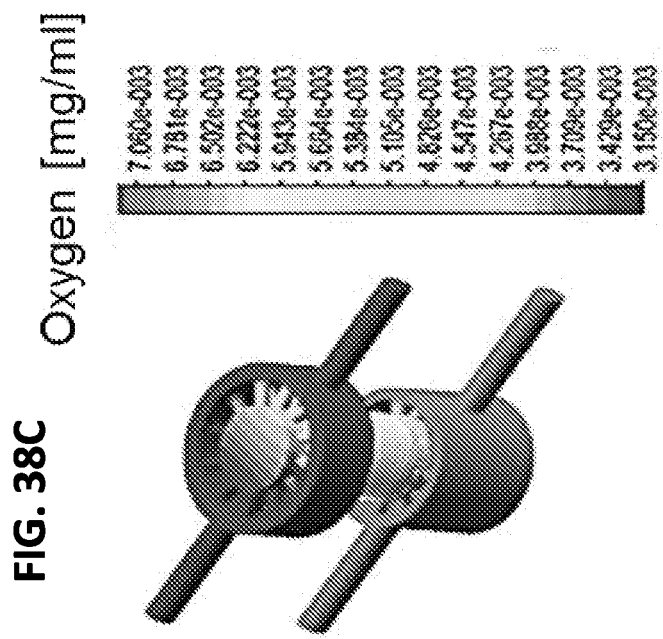

Firstly, as explained in section 2.3.2, we see that axial advection is dominant with respect to the cross-wind diffusion. Therefore, the higher the flow rates and fluid velocity, the more the inlet and outlet oxygen concentrations look similar due to a reduced oxygen drop (FIG. 37B and FIG. 38B). However, the diffusion of oxygen from the lower chamber to the upper one is not negligible, because different inlet concentrations promote the formation of concentration gradients that trigger transport.

For both the GelMA and PLLA cases, the oxygen concentration in the top region of the scaffold is higher in the case of low flow rate, (a, inlet flow equal to 1 ml/day) than in the case of high flow rate (c, inlet flow equal to 10 ml/day). Concerning case (b), the mix of the two chambers' flow is greater and a contribution of convective transport is added to the diffusive flux from the bottom towards the top of the bioreactor chamber. For this reason, the oxygen concentration in the top region of the scaffold is greater in case (b) than in cases (a) and (c).

Finally, the simulations suggest that the scaffold porosity and permeability play a relevant role on mass transport. Indeed, while the GelMA is permeable to oxygen, the PLLA is not. This implies that the aforementioned phenomena are more evident with a polymeric scaffold impervious to mass transport through the solid phase, such as PLLA.

4.3 Oxygen Consumption

The simulations of oxygen consumption were performed for the two different scaffolds (GelMA and PLLA) for an array of 4-units, in order to study the depletion of nutrients in the culture medium. The flow split is the one of case (a) (1 and 1 ml/day) and the inlets concentrations are equal to 3.15 and 7.2 µg/l at the upper and lower inlet, which correspond to the normoxic levels of the different types of tissue grown in the upper and lower chambers.

Figure 39:
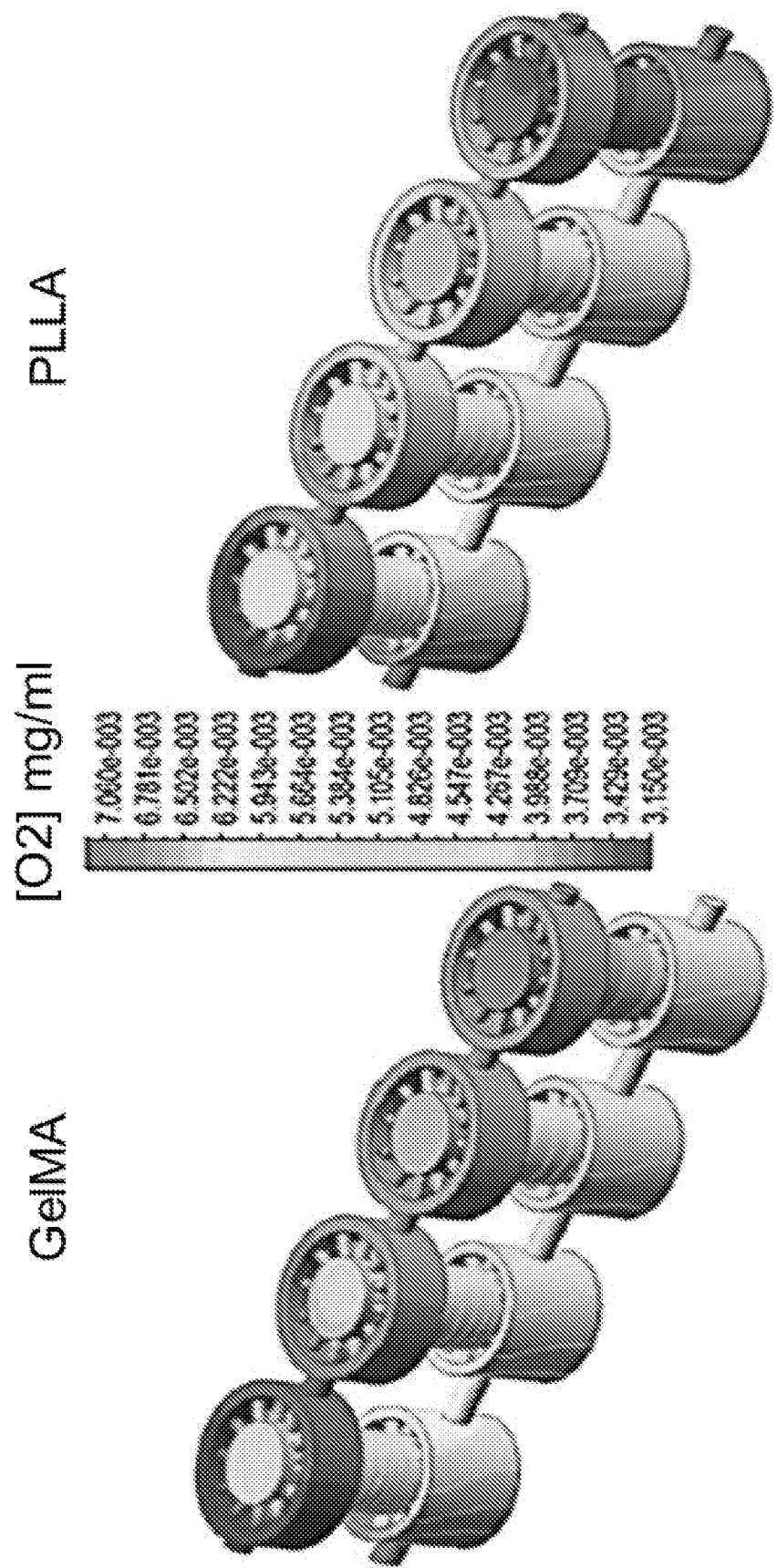
FIG. 39 shows oxygen concentration in the 4 cells array. GelMA (left) and PLLA (right) scaffolds are used when with active consumption rate.

Since we consider a 4-unit array, we observe that diffusion develops more easily along the bioreactor axis (longer fluid path with respect to the 1-unit case) and as a consequence, the oxygen concentration tends to become more uniform. More precisely, enhanced diffusion combined with different inlet concentrations causes a decrease of the oxygen level in the lower chamber and an increase in the top one. This trend is heightened by cellular oxygen consumption, which further leads to a diminishing of the oxygen concentration in the lower chamber (FIG. 39).

The two types of scaffold show the same trend of oxygen consumption, but the computations highlighted different percentage of consumed oxygen (Tables 2 and 3). Indeed, a higher percentage of oxygen consumption was found for the PLLA scaffolds with respect to GelMA. This effect is likely a result of the different cell density used for the two cases. In fact, cell density is assumed to be equal to $1 \times 10^6$ cells/ml for GelMA and to $2.12304019 \times 10^6$ cells/ml in the case of PLLA.

4.4 Comparison of Distributed and Lumped Parameter Models

In this section, the results of the lumped and the distributed parameter models are presented and compared in terms of fluid dynamics and mass transport. The fluid dynamics results for 1-unit and 4-units array are first presented, then, the mass transport results of both configurations are studied. For the sake of brevity, we present only the results obtained by simulating the GelMA scaffold.

4.4.1 Fluid Dynamics

Two computational fluid dynamics simulations were performed for the single unit configuration to determine the lumped parameter model (LPM). In particular, two inlet flow pairs are applied as reported in Table 12. The resulting LPM matrix M is:

$$M = \begin{bmatrix} 1 & 6.820e-8 \\ 6.188e-8 & 0.9999 \end{bmatrix} \quad (34)$$

Then, the results of the 1-unit and 4-unit LPMs are compared to those of the distributed parameter model, see Tables 13 and 14, and in two test cases the error was lower than 1%.

TABLE 12

Simulation settings to identify the fluid dynamics characteristics of one-unit bioreactor.

| | $Q_{in,\,top}$ [Kg/s] | $Q_{in,\,down}$ [Kg/s] | $Q_{out,\,top}$ [Kg/s] | $Q_{out,\,down}$ [Kg/s] |
|---|---|---|---|---|
| #1 | 1e−08 | 0 | 1e−08 | 6.19e−16 |
| #2 | 0 | 1e−08 | 6.82e−16 | 9.99e−9 |

TABLE 13

Comparison of the 1-unit fluid dynamics results provided by the distributed (distr) and the lumped (lump) parameter models.

| | $Q_{in,top}$ [Kg/s] | $Q_{in,down}$ [Kg/s] | $Q_{out,top,\ distr}$ [Kg/s] | $Q_{out,down,\ distr}$ [Kg/s] | $Q_{out,top,\ lump}$ [Kg/s] | $Q_{out,down,\ lump}$ [Kg/s] |
|---|---|---|---|---|---|---|
| #1 | 1.157e−08 | 1.157e−08 | 1.157e−08 | 1.157e−08 | 1.157e−08 | 1.569e−08 |
| #2 | 1.157e−08 | 2.314e−08 | 1.157e−08 | 2.314e−08 | 1.157e−08 | 2.313e−08 |

TABLE 14

Comparison of the 4-unit array fluid dynamics results provided by the distributed (distr) and the lumped (lump) parameter models.

| | $Q_{in,top}$ [Kg/s] | $Q_{in,down}$ [Kg/s] | $Q_{out,top,\ distr}$ [Kg/s] | $Q_{out,down,\ distr}$ [Kg/s] | $Q_{out,top,\ lump}$ [Kg/s] | $Q_{out,down,\ lump}$ [Kg/s] |
|---|---|---|---|---|---|---|
| #1 | 1.157e−08 | 1.157e−08 | 1.157e−08 | 1.157e−08 | 1.157e−08 | 1.569e−08 |
| #2 | 1.157e−08 | 2.314e−08 | 1.157e−08 | 2.314e−08 | 1.157e−08 | 2.313e−08 |

4.4.2 Mass Transport

For the LPM model of mass transport we have adopted the parameters of Table 9 and inlet concentrations summarized in Table 15.

TABLE 15

Simulation settings to identify the mass transport input-output characteristics of one-unit bioreactor.

| | $[O_2]_{in,\ top}$ [mg/ml] | $[O_2]_{in,\ down}$ [mg/ml] | $[O_2]_{out,\ top}$ [mg/ml] | $[O_2]_{out,\ down}$ [mg/ml] |
|---|---|---|---|---|
| #1 | 1e−03 | 0 | 8.514e−04 | 1.486e−04 |
| #2 | 0 | 1e−03 | 1.486e−04 | 8.514e−04 |

To start with, we analyze the mass transport model without cell metabolism, that is the case $S(C_s)=0$ in equation 12. The LPM model for the corresponding mass transport simulations is the following matrix:

$$D = \begin{bmatrix} 0.8481 & 0.1519 \\ 0.1519 & 0.8481 \end{bmatrix} \quad (35)$$

The results of the 1-unit LPM are compared with those of the distributed parameter model in two simulations with different inlets concentrations, reported in Table 16, whose values are set according to ongoing experimental tests. The results from the LPM model differ from those of the distributed parameters model by less than the 1%.

TABLE 16

Comparison of the one-unit oxygen concentration results provided by the distributed (distr) and the lumped (lump) parameter models.

| | $[O_2]_{in,top}$ [mg/ml] | $[O_2]_{in,down}$ [mg/ml] | $[O_2]_{out,top,\ distr}$ [mg/ml] | $[O_2]_{out,down,\ distr}$ [mg/ml] | $[O_2]_{out,top,\ lump}$ [mg/ml] | $[O_2]_{out,down,\ lump}$ [mg/ml] |
|---|---|---|---|---|---|---|
| #1 | 3.15e−03 | 7.2e−03 | 3.765e−03 | 6.585e−03 | 3.765e−03 | 6.585e−03 |
| #2 | 2e−03 | 4e−03 | 2.304e−03 | 3.696e−03 | 2.304e−03 | 3.696e−03 |

We also calculate the LPM model for mass transport with active cell metabolism. For the linear model, $S(C_s)=rC_s$, the LPM matrix for 1-unit is the following $$D_l = \begin{bmatrix} 0.6550 & 0.137 \\ 0.137 & 0.605 \end{bmatrix} \quad (36)$$

while for the Michaelis-Menten case, namely equations (18,19), the LPM model becomes $$D_{mm} = \begin{bmatrix} 0.8377 & 0.1347 \\ 0.1327 & 0.8147 \end{bmatrix} \quad (37)$$

The inspection of the matrices $D,D_l,D_{mm}$ informs about the characteristics of the different consumption models compared here. We observe that the diagonal entries of $D_l$ are the smallest, confirming that the linear model is the one with the highest oxygen consumption rate. The extra-diagonal coefficients correspond to the oxygen exchange between the upper and lower chambers. Their magnitude is similar in all cases, because they depend on the diffusion parameters solely. For the linear case, the theory at the basis of the LPM derivation is satisfied, while it does not rigorously hold true for the Michaelis-Menten model, because the mass transport equation becomes nonlinear. Once again, numerical simulations based on the full model applied to the 8-unit array confirm that the LPM model with linear consumption rate, namely $D_l$, predicts outlet concentrations with less than 1% error. The corresponding results are reported in Table 17 and visualized in FIG. 40. In Table 18 we report the error of the LPM based on the Michaelis-Menten nonlinear consumption rate. Despite the nonlinear nature of the problem, in conflict with the principles at the basis of the LPM derivation, the LPM model is fairly accurate in predicting the concentration split and decay at the outlet also with a Michaelis-Menten consumption rate, with a maximum error of about 10% for an array of 4-units, located on the bottom outlet of the bioreactor.

TABLE 17

Comparison of the 8-unit array oxygen concentration results provided by the distributed (distr) and the lumped (lump) parameter models with linear consumption rate.

|    | $[O_2]_{in,top}$ [mg/ml] | $[O_2]_{in,down}$ [mg/ml] | $[O_2]_{out,top, distr}$ [mg/ml] | $[O_2]_{out,down, distr}$ [mg/ml] | $[O_2]_{out,top, lump}$ [mg/ml] | $[O_2]_{out,down, lump}$ [mg/ml] |
|----|---------|---------|-----------|-----------|-----------|-----------|
| #1 | 3.15e−03 | 7.2e−03 | 6.555 e−4 | 5.628 e−4 | 6.545 e−4 | 5.613 e−4 |
| #2 | 2e−03   | 4e−03   | 3.826 e−4 | 3.274 e−4 | 3.821 e−4 | 3.265 e−4 |

TABLE 18

Comparison of the 4-unit array oxygen concentration results provided by the distributed (distr) and the lumped (lump) parameter models with Michaelis-Menten consumption rate.

|    | $[O_2]_{in,top}$ [mg/ml] | $[O_2]_{in,down}$ [mg/ml] | $[O_2]_{out,top, distr}$ [mg/ml] | $[O_2]_{out,down, distr}$ [mg/ml] | $[O_2]_{out,top, lump}$ [mg/ml] | $[O_2]_{out,down, lump}$ [mg/ml] |
|----|---------|---------|-----------|-----------|-----------|-----------|
| #1 | 3.15e−03 | 7.2e−03 | 3.754e−03 | 4.295e−03 | 3.971e−03 | 4.678e−03 |
| #2 | 2e−03   | 4e−03   | 2.202e−03 | 2.43e−03  | 2.3482e−03 | 2.677e−03 |

The LPM model for mass transport is particularly interesting because it allows us to estimate the decay of nutrient concentrations due to cell metabolism along an arbitrarily long array of units, using the formula $\underline{C}_{out}(n) = D^n \cdot \underline{C}_{in}$. Considering for example the inlet concentrations of Table 16, test case #2 for $\underline{C}_{in}$, we estimate the outlet concentration decay for the transport model without oxygen consumption. The same calculation is then repeated for the linear and the Michaelis-Menten models for cell metabolism and the results are compared in FIG. 40, where also the outlet concentrations determined using the fully 3D simulations are shown for a qualitative visualization of the LPM error.

5 Discussion

From the engineering standpoint, our study shed lights on important aspects of the bioreactor behavior. We observe that the flow is dominated by viscous effects and by pressure gradients, while inertial effects are negligible. Differences in inlet velocities between upper and lower chamber generate a vertical pressure gradient inside the bioreactor chambers, which promotes mixing of nutrient fluid flowing through the osteochondral construct. Furthermore, we have observed that the magnitude of vertical pressure gradients depends highly on the permeability of the scaffold. Between the two materials tested here, it appears that the most permeable one favors the mixing of fluid among the upper and lower chambers.

Concerning mass transfer, our simulations suggest that it is dominated by convection. Diffusion effects are however non-negligible, but their (relative) intensity varies according to the inlet flow rate and the scaffold properties. More precisely, FIGS. 37A-37C and FIGS. 38A-38C show that high flow rates decrease the transport of biochemical species between the two chambers. From the analysis of these plots we also observe that the concentration in the bioreactor top chamber is greater than the one at the upper outlet. This means that the exchange between the chamber and the supplying channels is not sufficient to remove all the chemical species that accumulate in this region, because of combined diffusion and convection. This effect is observable for both types of scaffold, but is more evident for GelMA, suggesting that this type of material hinders flow and mass transport more than PLLA does. When nutrient (or oxygen) consumption is switched on in the simulation, concentration gradients are quickly smoothed out when traveling along multiple bioreactor units. At the same time, concentration levels significantly decrease. The computational model thus serves as a valuable tool to estimate whether the final units of the row receive enough nutrients, as illustrated in the examples presented above.

Figure 40:
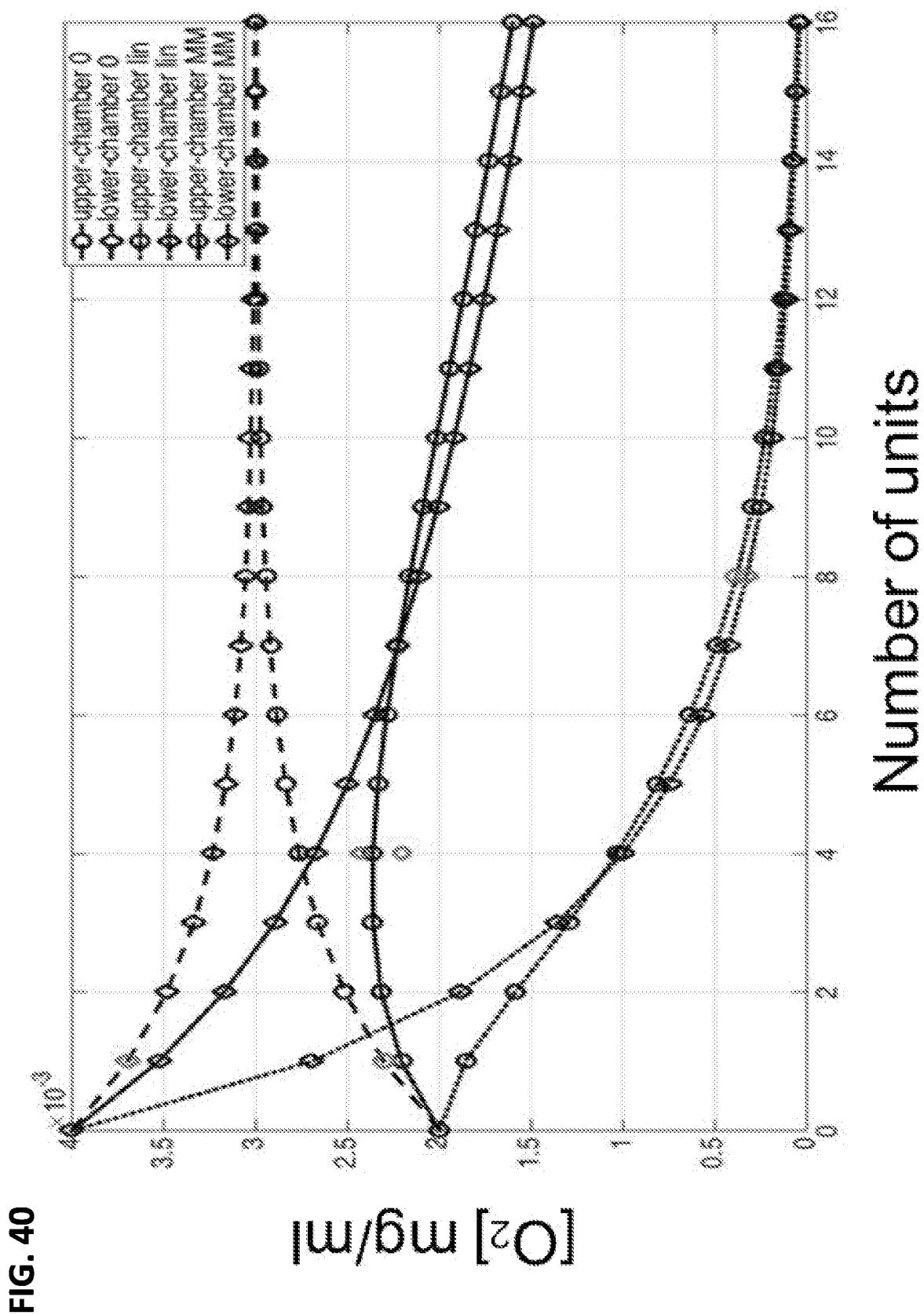
FIG. 40 shows variation of the outlet concentration of oxygen with respect to the number of units (unit #0 denotes the inlet value) for the mass transport model without cell metabolism (dashed line), with linear consumption rate (dotted line) and with Michaelis-Menten consumption model (solid line). Data calculated using the full 3D model are reported in red.

Finally, we have developed a surrogate, inexpensive approach to characterize the output of the bioreactor without the burden of running many computer simulations. It consists of a lumped parameter model, derived exploiting the linearity of the full model. The LPM has proven to be very accurate in capturing the effect of sequentially combining multiple units. A natural application of this model is studying the concentration decay along a sequence of bioreactor units. For example, FIG. 40 shows the concentration decay at the bioreactor outlets when the number of units is varied from 1 to 16. Three sets of curves outline the behavior of different cell metabolism models. When cell metabolism is switched off (dashed lines), the upper and lower concentrations equilibrate very quickly, confirming that diffusion effects of oxygen between the two chambers are non-negligible. We recall that large oxygen diffusion and transport between the upper and lower chambers is not necessarily desirable, when different types of tissue are grown. Indeed, in our case, cartilage natural environment should be hypoxic, while bone better develops in normoxic conditions. For constant consumption rate, the concentration decay is the largest. As a consequence after 16 bioreactor units, almost all the nutrient concentration has been consumed. The Michaelis-Menten metabolic model is the most realistic of the three options, because it accounts for a saturation effect that limits the consumption rate. According to our preliminary data on cell viability in the bioreactor, obtained by Live/Dead assays (data not shown), the oxygenation computed after 16-units appears to be still at a sufficient level.

The computational approach proposed here is subject to some limitations. One is the approximation of the fluid dynamic and mass transport through steady model. A key challenge in the engineering of three-dimensional tissue is maintenance of cell viability when the volumetric cell density increases. In this study, we assumed a constant cell density equal to the initial culture conditions that occur after distributing cells homogenously throughout the volume of the scaffolds. However, variations in cell density with time could be easily incorporated in both our models, to predict oxygen drops in long-term culture. Secondly, as literature data are lacking, we assumed the GelMA properties (i.e., porosity and permeability) equal to those of native cartilage. Experimental test will be performed in future work to assess these properties. Finally, we have not accounted for transport along capillaries. This could be acceptable for many engineered constructs that are approximation of native tissues, frequently obtained from single cell types, e.g., mesenchymal stem cells, within a hydrogel or a porous scaffold. If the HTB were to be used with native tissues, we expect our approach to hold true with the necessary adjustments to account for the different tissues types. The avascular components of cartilage would be modelled adjusting the parameters we currently used for GelMA, whereas the for the vascularized bone, the more porous structure we described for the PLLA scaffold could offer a good starting model to approximate the cavities and capillaries present in subchondral bone.

Another improvement of our study would be to validate the oxygen concentration drops predicted by our models with actual measurements performed when the bioreactor is operated with cell-seeded constructs. This validation would be technically challenging, only feasible using oxygen sensors incorporated in the perfusion circuit, at the inlet and outlets of each bioreactor unit or even inserted directly in the chambers, in direct contact with the living cells. Detecting larger molecules, even at low concentrations provides a more simple and reliable quantification. On this basis, extensive validation of the ability of our models to predict the flow-dynamics and mass transport in the bioreactor will be the subject of future work.

6 Conclusions and Perspectives

From the methodological standpoint, we have overcome the challenge of developing a complex multi-physics model of the bioreactor. We have also succeeded in implementing the model into a commercial computational platform, showing the significant potential of computational tools on biomedical research, including analytical cases integrating quantitative biology and translational medicine. Future developments of this study consist of experimental validation of the models and their application to explore different bioreactor configurations. Such findings allow optimization of the model by incorporating the multi-faceted factors that affect its behavior and functionality.

General Considerations

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Integers, characteristics, materials, and other features described in conjunction with a particular aspect, embodiment, or example of the disclosed technology are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

As used herein, the terms "a", "an", and "at least one" encompass one or more of the specified element. That is, if two of a particular element are present, one of these elements is also present and thus "an" element is present. The terms "a plurality of" and "plural" mean two or more of the specified element. As used herein, the term "and/or" used between the last two of a list of elements means any one or more of the listed elements. For example, the phrase "A, B, and/or C" means "A", "B,", "C", "A and B", "A and C", "B and C", or "A, B, and C." As used herein, the term "coupled" generally means physically or fluidly coupled or linked and does not exclude the presence of intermediate elements between the coupled items absent specific contrary language.

In view of the many possible embodiments to which the principles of the disclosed technology may be applied, it should be recognized that the illustrated embodiments are only examples and should not be taken as limiting the scope of the disclosure. Rather, the scope of the disclosure is at least as broad as the following claims. We therefore claim all that comes within the scope of these claims.

The invention claimed is:

1. A bioreactor system comprising:
a main body, a base, and a cover, with a well being formed within the main body between the base and the cover when the base and the cover are secured to the main body, the well configured to contain a cellular biological material;
the main body comprising fluidic passageways including a fluid inlet coupled to the well and a fluid outlet coupled to the well, the fluidic passageways configured to conduct a fluid flow through the bioreactor such that the fluid flow interacts with the cellular biological material in the well;
the cover comprising a viewing aperture that provides external optical access to the cellular biological material in the well when the base and the cover are secured to the main body;

the base comprising a projection that extends up into the main body and defines a bottom surface of the well that is above a bottom surface of the main body; and the base and cover being detachable from the main body such that the cellular biological material is accessible from above and below the well.

2. The system of claim 1, wherein the fluidic passageways are configured to provide diffusion of a fluid through the cellular biological material in the well.

3. The system of claim 1, wherein the fluidic passageways are configured to provide perfusion of a fluid through the cellular biological material in the well.

4. The system of claim 1, wherein the fluidic passageways comprise at least two inlets for conducting two fluid streams to interact with the cellular biological material in the well.

5. The system of claim 1, wherein the fluidic passageways comprise at least two outlets for conducting two fluid streams out of the system.

6. The system of claim 1, wherein the fluidic passageways comprise one fluid stream for diffusion through the cellular biological material and one fluid stream for perfusion through the biological material.

7. The system of claim 1, wherein the fluidic passageways comprise a first fluid stream coupled to a first portion of the well and a second fluid stream coupled to a second portion of the well.

8. The system of claim 7, wherein the first fluid stream is for diffusion through a first cellular biological material in the first portion of the well, and the second fluid stream is for diffusion through a second cellular biological material in the second portion of the well, the first and second biological materials being biologically different from each other.

9. The system of claim 1, wherein the outlet is coupled to an inlet of another bioreactor.

10. The system of claim 1, wherein the inlet is fluidly coupled to two or more different wells arranged in parallel.

11. The system of claim 1, wherein the inlet is fluidly coupled to two or more different wells arranged in series.

12. The system of claim 1, wherein the outlet is fluidly coupled to two or more different wells arranged in parallel.

13. The system of claim 1, wherein the outlet is fluidly coupled to two or more different wells arranged in series.

14. The system of claim 1, wherein the bioreactor system comprises a plurality of wells each configured to contain a cellular biological material, and each having its own fluid inlet and its own fluid outlet, and each having its own viewing aperture.

15. The system of claim 14, wherein the system comprises a single base that comprises a plurality of projections, one for each of the plurality of wells, wherein each projection defines a bottom surface of a respective well.

16. The system of claim 15, wherein the single base is detachable to provide access each of the wells simultaneously.

17. The system of claim 1, wherein the viewing aperture includes an optically transparent layer of material that forms an upper surface of the well and also provides optical access to the cellular biological material in the well.

18. The system of claim 1, wherein the well is rectangular.

19. The system of claim 1, wherein the well has a volume of 10 μL or less.

20. The system of claim 1, wherein the system is operable to develop two different biological tissues in contact with each other inside the well, with each tissue being fed a different fluid during development.

21. The system of claim 1, wherein reporter genes of the cellular biological material in the well, can be optically monitored from outside the well through the viewing aperture in the cover.

22. The system of claim 1, wherein the cover comprises a non-optically transparent plate having an aperture, and an optically transparent component positioned in, below, or over the aperture in the plate.

23. The system of claim 1, wherein the cover comprises an adhesive film that adhesively secures to the main body around an upper end of the well.

24. The system of claim 1, wherein the base comprises a mechanical locking feature that enables the base to be secured to the main body, without screws, bolts, or other additional fasteners.

25. A method comprising:
using a bioreactor system to grow or test cellular biological material in a well with optical access to the biological material through a cover;
wherein the bioreactor system comprises a main body, a base, and the cover, with the well being formed within the main body between the base and the cover when the base and the cover are secured to the main body;
wherein the main body comprises fluidic passageways including a fluid inlet coupled to the well and a fluid outlet coupled to the well, wherein the fluidic passageways conduct a fluid flow through the bioreactor such that the fluid flow interacts with a biological material in the well;
wherein the cover provides comprises a viewing aperture that provides external optical access to the biological material in the well when the base and the cover are secured to the main body; and
wherein the base comprises a projection that extends up into the main body and defines a bottom surface of the well that is above a bottom surface of the main body;
detaching the base and the cover from the main body; and
with the base and the cover detached, pushing the biological material out of the well from below the main body.

26. The method of claim 25, wherein the method comprises developing two different biological tissues in contact with each other inside the well, with each tissue being fed a different fluid during development.

27. The method of claim 25, wherein the method comprises optically monitoring reporter genes or fluorescent materials from outside the well through the viewing aperture provided by the cover.

28. The method of claim 25, wherein the method comprises using the system for drug screening or toxicological screening.

29. The method of claim 25, wherein the method comprises securing the base to the main body by engaging mating engagement portions on the base and the main body, without using other additional fasteners to secure the base to the main body.

30. The method of claim 25, wherein the method comprises securing the base to the main body, then placing a biological material in the well above the projection, and then securing the cover over the top of the well to seal the biological material in the well.

* * * * *